(12) United States Patent
He

(10) Patent No.: US 10,596,183 B2
(45) Date of Patent: *Mar. 24, 2020

(54) PHARMACEUTICAL COMPOSITIONS AND THEIR USE FOR TREATMENT OF CANCER AND AUTOIMMUNE DISEASES

(71) Applicant: ZHEJIANG DTRM BIOPHARMA CO. LTD., Hangzhou, Zhejiang Province (CN)

(72) Inventor: Wei He, Audubon, PA (US)

(73) Assignee: ZHEJIANG DTRM BIOPHARMA CO. LTD., Hangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/123,203

(22) Filed: Sep. 6, 2018

(65) Prior Publication Data

US 2019/0192541 A1    Jun. 27, 2019

Related U.S. Application Data

(60) Division of application No. 15/628,143, filed on Jun. 20, 2017, now Pat. No. 10,098,900, which is a division of application No. 15/183,340, filed on Jun. 15, 2016, now Pat. No. 9,717,745, which is a continuation-in-part of application No. PCT/CN2016/000149, filed on Mar. 18, 2016.

(30) Foreign Application Priority Data

Mar. 19, 2015 (CN) .......................... 2015 1 0119944

(51) Int. Cl.

| | | |
|---|---|---|
| *A61K 31/519* | (2006.01) | |
| *A61K 31/436* | (2006.01) | |
| *A61K 31/453* | (2006.01) | |
| *A61K 31/635* | (2006.01) | |
| *A61K 45/06* | (2006.01) | |
| *C07D 487/04* | (2006.01) | |
| *A61P 35/00* | (2006.01) | |
| *A61K 31/52* | (2006.01) | |
| *A61K 31/454* | (2006.01) | |
| *A61K 31/4162* | (2006.01) | |

(52) U.S. Cl.
CPC .......... *A61K 31/635* (2013.01); *A61K 31/436* (2013.01); *A61K 31/454* (2013.01); *A61K 31/519* (2013.01); *A61K 31/52* (2013.01); *A61K 45/06* (2013.01); *A61P 35/00* (2018.01); *C07D 487/04* (2013.01); *A61K 31/4162* (2013.01); *A61K 2300/00* (2013.01)

(58) Field of Classification Search
CPC ... A61K 31/519; A61K 31/436; A61K 31/453
See application file for complete search history.

(56) References Cited

U.S. PATENT DOCUMENTS

| | | |
|---|---|---|
| 8,673,925 B1 | 3/2014 | Goldstein |
| 8,940,744 B2 | 1/2015 | Owens et al. |
| 9,532,990 B2 | 1/2017 | He |
| 9,861,636 B2 | 1/2018 | He |
| 2012/0108612 A1 | 5/2012 | Lee et al. |
| 2017/0027941 A1 | 2/2017 | James et al. |
| 2018/0207161 A1 | 7/2018 | He |

FOREIGN PATENT DOCUMENTS

| | | |
|---|---|---|
| CA | 2947338 | 11/2015 |
| WO | WO 2008/039218 | 4/2008 |
| WO | WO 2008/058944 | 5/2008 |
| WO | 2008/121742 A2 | 10/2008 |
| WO | WO 2010/009342 | 1/2010 |
| WO | WO 2011/046964 | 4/2011 |
| WO | WO 2012/158764 | 11/2012 |
| WO | WO 2013/010136 | 1/2013 |
| WO | WO 2013/191965 | 12/2013 |
| WO | 2014/022390 A1 | 2/2014 |
| WO | WO 2014/022569 | 2/2014 |
| WO | WO 2014/039899 | 3/2014 |
| WO | WO 2014/143807 | 9/2014 |
| WO | 2014/172429 A1 | 10/2014 |
| WO | WO 2014/166820 | 10/2014 |
| WO | WO 2014/168975 | 10/2014 |
| WO | WO 2015/165279 | 11/2015 |

OTHER PUBLICATIONS

ClinicalTrials.gov "NCT02077166 on Dec. 9, 2015" (2015).
Ezell et al., "Synergistic induction of apoptosis by combination of BTK and dual mTORC1/2 inhibitors in diffuse large B cell lymphoma," Oncotarget 5(13):4990-5001 (2014).
Griner et al., "High-throughput combinatorial screening identifies drugs that cooperate with ibrutinib to kill activated B-cell-like diffuse large B-cell lymphoma cells," Proc Natl Acad Sci U S A. 111(6):2349-54 (2014).
Jin et al., "Low dose of lenalidmide and PI3K/mTOR inhibitor trigger synergistic cytotoxicity in activated B cell-like subtype of diffuse large B cell lymphoma," J Exp Clin Cancer Res 35:52 (2016).
Levy et al., "Dications of fluorenylidenes. The effect of substituent electronegativity and position on the antiaromaticity of substituted tetrabenzo[5.5]fulvalene dications," J Org Chem 68(10):3990-3998 (2003).
Marostica et al., "Population pharmacokinetic model of ibrutinib, a Bruton tyrosine kinase inhibitor, in patients with B cell malignancies," Cancer Chemother Pharmacol 75:111-121 (2015).

(Continued)

*Primary Examiner* — Samira J Jean-Louis
(74) *Attorney, Agent, or Firm* — Steptoe & Johnson LLP; Z. Ying Li

(57) ABSTRACT

Described herein are combination therapies for cancer (such as lymphoid malignancies) and immune diseases (such as autoimmune diseases and inflammatory diseases). The therapies comprise the combined use of inhibitors of BTK, mTOR kinase, and Bcl-2 or their signaling pathways, and immunomodulatory drugs. Also described are pharmaceutical compositions and kits comprising these inhibitors.

3 Claims, 17 Drawing Sheets

(56) References Cited

OTHER PUBLICATIONS

Roschewski et al., "Diffuse large B-cell lymphoma-treatment approaches in the molecular era," Nat Rev Clin Oncol 11(1):12-23 (2014).
Shi et al, "Purine derivatives as potent Bruton's tyrosine kinase (BTK) inhibitors for autoimmune diseases," Bioorg Med Chem Lett 24(9):2206-2211 (2014).
Tabe et al., "Selective inhibitor of nuclear export selinexor (KPT-330) and BCL2 inhibitor ABT-199 enhance the anti-lymphoma effect of BTK inhibitor ibrutinib in mantle cell lymphoma," Blood 124:2254 (2014).
Vargas et al, "Inhibitors of BTK and ITK: state of the new drugs for cancer, autoimmunity and inflammatory diseases," Scand J Immunol 78(2):130-139 (2013).
Wanner et al., "Mammalian target of rapamycin inhibition induces cell cycle arrest in diffuse large B cell lymphoma (DLBCL) cells and sensitises DLBCL cells to rituximab," Br J Haematol 134(5):475-84 (2006).
Souers et al., "ABT-199, a potent and selective BCL-2 inhibitor, achieves antitumor activity while sparing platelets," Nat Med 19(2):202-8 (2013).
CN Priority Application No. 201510119944.5 with English translation and Certificate, 117 pages.

Note: p.o., BID. *14 days;

Note: 1. ▲ Tumor disappeared after 9 days of treatment. Drug delivery was stopped.
2. ▲ No tumor reboundance was observed after stoping drug delivery 12 days.
3. ■ 21 days of continuous treatment.

———, Vehicle; ———, Compound 3 at 5 mg/kg+ Compound 15 at 5 mg/kg +Compound 14 at 0.5 mg/kg, po BID *14d; ———, Compound 3 at 10 mg/kg+ Compound 15 at 1 mg/kg +Compound 14 at 0.5 mg/kg, po BID *14d; ———, Compound 3 at 20 mg/kg+ Compound 15 at 1 mg/kg +Compound 14 at 0.5 mg/kg, po BID *14d ———, Vehicle; —■—, Compound 3 at 5 mg/kg+ Compound 15 at 5 mg/kg +Compound 14 at 0.5 mg/kg, po BID *14d; —◆—, Compound 9 at 5 mg/kg+ Compound 15 at 5 mg/kg +Compound 14 at 0.5 mg/kg, po BID *14d

Figure 12

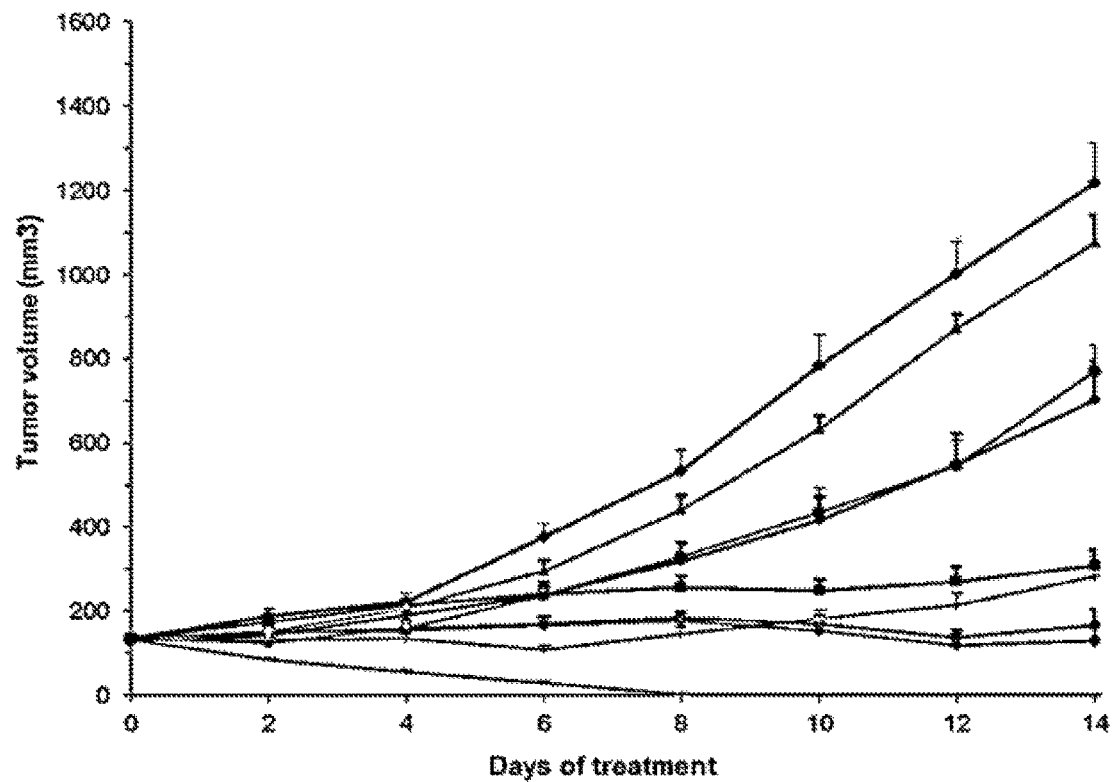

━━━ Vehicle; ━▪━, Compound 3 at 5 mg/kg, po BID * 14d; ━▪━, Compound 12 at 5 mg/kg, po. BID * 14d; ━▪━, Compound 8 at 10 mg/kg, po BID *14d; ━▪━, Compound 3 at 5 mg/kg +Compound 12 at 5 mg/kg, po BID *14d; ━▪━, Compound 8 at 10 mg/kg +Compound 12 at 5 mg/kg, po BID *14d; ━━━, Compound 14 at 0.5 mg/kg +Compound 12 at 5mg/kg, po BID *14d; ━━━, Compound 3 at 5 mg/kg +Compound 12 at 5mg/kg +Compound 14 at 0.5 mg/kg, po BID *14d; ━▪━, Compound 3 at 5 mg/kg + Compound 12 at 5mg/kg + Compound 8 at 10mg/kg, po BID *14d

PHARMACEUTICAL COMPOSITIONS AND THEIR USE FOR TREATMENT OF CANCER AND AUTOIMMUNE DISEASES

CROSS-REFERENCE TO RELATED APPLICATIONS

This application is a division of U.S. application Ser. No. 15/628,143, filed Jun. 20, 2017, which is a division of U.S. application Ser. No. 15/183,340, filed Jun. 15, 2016 and claiming the benefit of International Application PCT/CN2016/000149, filed Mar. 18, 2016 and claiming priority from Chinese Patent Application No. 201510119944.5, filed Mar. 19, 2015. The contents of the aforementioned priority applications are incorporated herein by reference in their entirety.

BACKGROUND OF THE INVENTION

Cancer treatment has evolved over time to become more targeted and less toxic to the patient. Traditional chemotherapy often has a high level of systemic toxicity. Targeted therapy uses small molecules or biologics (e.g., therapeutic antibodies) to inhibit the activity of a selected cellular protein involved in cancer development, and causes much less side effect than traditional chemotherapy. Immunotherapies such as those targeting immune checkpoints (e.g., PD-1 and PD-L1) and those involving chimeric antigen receptor T (CAR-T) cells aim to bolster the patient's own anti-cancer immune defense, and have emerged as a promising new treatment paradigm.

One of the cellular proteins that have been targeted in cancer therapy is Bruton tyrosine kinase (BTK). BTK is a member of the Tec family of protein tyrosine kinases. BTK has domains with pleckstrin homology (PH), Tec homology (TH), Src homology 3 (SH3), Src homology 2 (SH2), and tyrosine kinase or Src homology 1 (TK or SH1) (Akinleye et al., "Ibrutinib and novel BTK inhibitors in clinical development," Journal of Hematology & Oncology, 2013, 6:59). Proper expression of the BTK gene in different lymphoid regions plays a key role in normal B-cell development. BTK is also involved in signal transduction pathways for B cell activation and survival (Kurosaki, "Molecular mechanisms in B cell antigen receptor signaling," Curr OP Imm, 1997, 9(3):309-18).

BTK functions downstream of multiple receptors, including B-Cell Receptor (BCR), receptors for growth factors and chemokines, and innate immune receptors. BTK initiates a broad range of cellular processes, such as cell proliferation, survival, differentiation, motility, adhesion, angiogenesis, cytokine production, and antigen presentation, and plays an important role in hematological malignancies and immune disorders. In a mouse model for chronic lymphocytic leukemia (CLL), BTK expression levels were shown to set the threshold for malignant transformation; BTK overexpression accelerated leukemia and increased mortality (Kil et al., "Bruton's tyrosine kinase mediated signaling enhances leukemogenesis in a mouse model for chronic lymphocytic leukemia," Am J Blood Res, 2013, 3(1):71-83).

Ibrutinib (also known commercially as IMBRUVICA®) was the first BTK inhibitor approved by the United States Food and Drug Administration for treating mantle cell lymphoma (MCL), chronic lymphocytic leukemia (CLL), and Waldenstrom's macroglobulinemia (WM). In general, however, the selectivity of known BTK inhibitors is not ideal—they inhibit not only BTK, but also various other kinases (such as ETK, EGF, BLK, FGR, HCK, YES, BRK and JAK3, etc.). Known BTK inhibitors also produce a variety of derivatives. These characteristics of known BTK inhibitors lead to a decrease in therapeutic efficacy and an increase in side effects. The pharmacokinetics of known BTK inhibitors also needs to be improved. Indeed, significant variations in bioavailability of ibrutinib have been observed clinically among patients (Marostica et al., "Population pharmacokinetic model of ibrutinib, a Bruton tyrosine kinase inhibitor, in patients with B cell malignancies," Cancer Chemother Pharmacol, 2015, 75:111-121).

SUMMARY OF THE INVENTION

The invention relates to methods of inhibiting cancer cells and treating cancer, and to methods of inhibiting lymphocytes (e.g., B cells) and treating immune disorders. In these methods, a BTK inhibitor such as a multi-fluoro-substituted pyrazolopyrimidine compound described herein and an inhibitor of mammalian target of rapamycin (mTOR) are used. In certain embodiments, a third drug, such as an inhibitor of B-cell lymphoma 2 (Bcl-2) or PI3 kinase, or an immunomodulatory drug (IMiD), is also used. Applicant has discovered that the particular combinations of drugs described herein are unexpectedly high synergistic effects and can effectively overcome drug resistance and disease recurrence. Combination therapies described herein are much safer than monotherapy due to the lower doses used and can shorten treatment cycle because of better therapeutic effects.

One aspect of the invention described herein relates to a method for treating a cancer, such as a lymphoid malignancy (e.g., chronic lymphocytic leukemia, Waldenström Macroglobulinemia, mantle cell lymphoma), comprising administering to a subject in need thereof a therapeutically effective amount of (i) a BTK inhibitor, (ii) an mTOR kinase inhibitor, and (iii) a Bcl-2 inhibitor or an IMiD. In some embodiments, the lymphoid malignancy is multiple myoloma, which is currently treated with IMiD or its existing combinations with other drugs, but there is still significant unmet medical needs for this disease.

Another aspect of the invention relates to method for treating an immune disorder, such as an autoimmune disease (e.g., rheumatoid arthritis and systemic lupus erythematosus), comprising administering to a subject in need thereof a therapeutically effective amount of (a) a Bruton tyrosine kinase (BTK) inhibitor, and (b) a mammalian target of rapamycin (mTOR) kinase inhibitor.

In some embodiments, the BTK inhibitor is selected from the group consisting of a compound represented by Formula I, II, Ia, Ib, IIa, or IIb, ibrutinib, acalabrutinib, BGB-3111, spebrutinib, ONO-4059, HM71224, RN486, CNX-774, CGI-11746, and other BTK inhibitors, and enantiomers, diastereomers, and pharmaceutically acceptable salts thereof, wherein the aforementioned Formulae are:

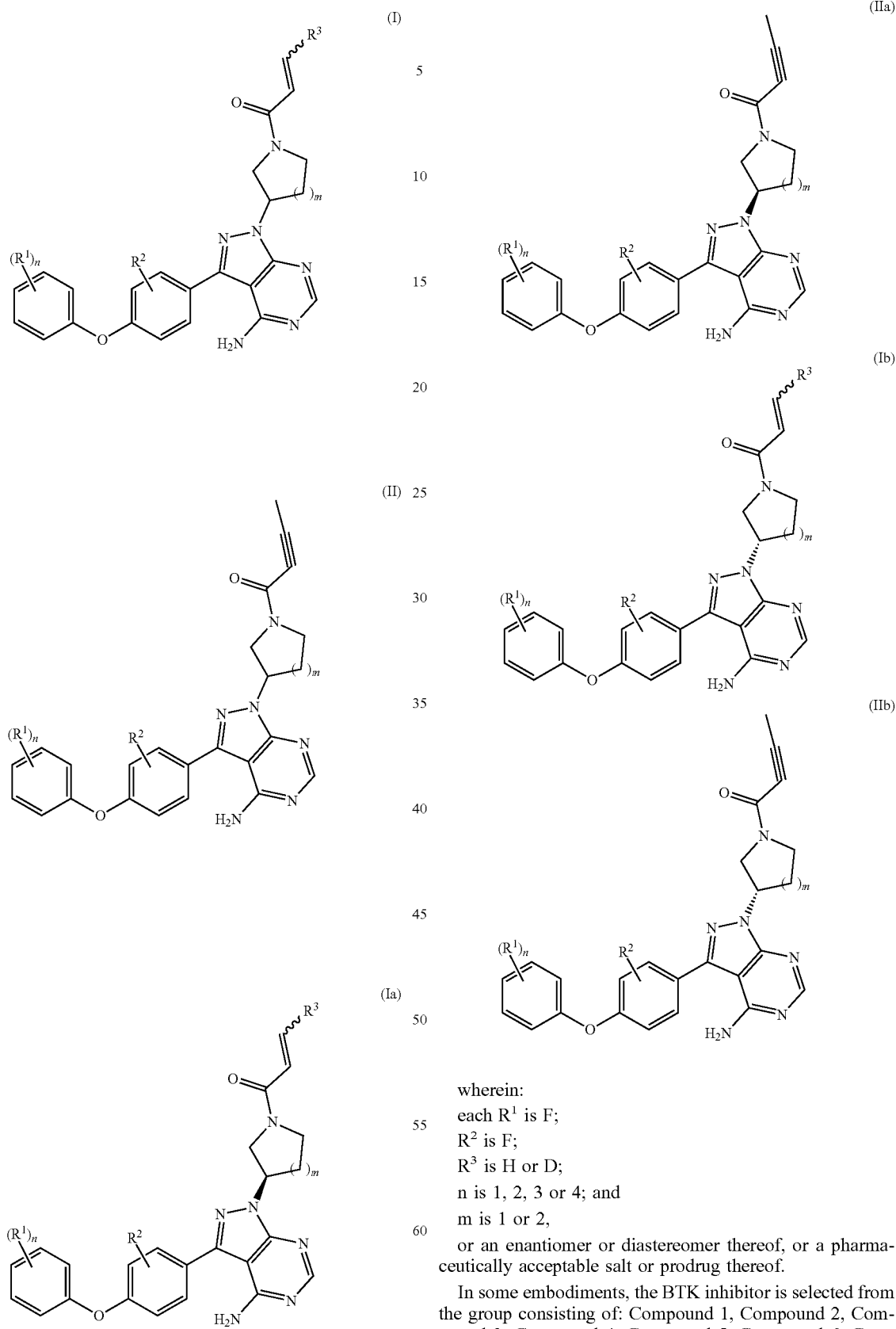

wherein:

each $R^1$ is F;

$R^2$ is F;

$R^3$ is H or D;

n is 1, 2, 3 or 4; and m is 1 or 2, or an enantiomer or diastereomer thereof, or a pharmaceutically acceptable salt or prodrug thereof.

In some embodiments, the BTK inhibitor is selected from the group consisting of: Compound 1, Compound 2, Compound 3, Compound 4, Compound 5, Compound 6, Compound 7, Compound 20, and enantiomers, diastereomers, and pharmaceutically acceptable salts thereof.

In some embodiments, the BTK inhibitor is Compound 3 or an enantiomer, diastereomer, or pharmaceutically acceptable salt thereof.

In some embodiments, the BTK inhibitor is Compound 5 or an enantiomer, diastereomer, or pharmaceutically acceptable salt thereof.

In some embodiments, the BTK inhibitor is ibrutinib or a pharmaceutically acceptable salt thereof.

In some embodiments, the mTOR kinase inhibitor is selected from the group consisting of everolimus, rapamycin, temsirolimus, ridaforolimus, XL388, GDC-0349, AZD2014, AZD8055, GSK105965, MLN0128, PI-103, NVP-BEZ235, WJD008, XL765, SF-1126, Torin1, PP242, PP30, Ku-0063794, WYE-354, WYE-687, WAY-600, INK128, OSI-027, other known mTOR kinase inhibitors, and pharmaceutically acceptable salts thereof.

In some embodiments, the mTOR kinase inhibitor is everolimus or a pharmaceutically acceptable salt thereof.

In some embodiments, the mTOR kinase inhibitor is rapamycin or a pharmaceutically acceptable salt thereof.

In some embodiments, the IMiD is lenalidomide, pomalidomide, thalidomide, CC-112, or CC-220, or a pharmaceutically acceptable salt thereof.

In some embodiments, the Bcl-2 inhibitor is selected from the group consisting of venetoclax (ABT-199), navitoclax, ABT-737, TW-37, sabutoclax, obatoclax, other known Bcl-2 inhibitors, and pharmaceutically acceptable salts thereof.

In some embodiments, the Bcl-2 inhibitor is venetoclax or a pharmaceutically acceptable salt thereof.

In some embodiments, the method comprises administering to a cancer patient a therapeutically effective amount of (a) ibrutinib or a pharmaceutically acceptable salt thereof, (b) everolimus or a pharmaceutically acceptable salt thereof, and (c) venetoclax or a pharmaceutically acceptable salt thereof.

In some embodiments, the method comprises administering to a cancer patient a therapeutically effective amount of (a) ibrutinib or a pharmaceutically acceptable salt thereof, (b) rapamycin or a pharmaceutically acceptable salt thereof, and (c) venetoclax or a pharmaceutically acceptable salt thereof.

In some embodiments, the method comprises administering to a cancer patient a therapeutically effective amount of (a) Compound 3 or an enantiomer, diastereomer, or pharmaceutically acceptable salt thereof, (b) everolimus or a pharmaceutically acceptable salt thereof, and (c) venetoclax or a pharmaceutically acceptable salt thereof.

In some embodiments, the method comprises administering to a cancer patient a therapeutically effective amount of (a) Compound 3 or an enantiomer, diastereomer, or pharmaceutically acceptable salt thereof, (b) rapamycin or a pharmaceutically acceptable salt thereof, and (c) venetoclax or a pharmaceutically acceptable salt thereof.

In some embodiments, the method comprises administering to a cancer patient a therapeutically effective amount of (a) Compound 5 or an enantiomer, diastereomer, or pharmaceutically acceptable salt thereof, (b) everolimus or a pharmaceutically acceptable salt thereof, and (c) venetoclax or a pharmaceutically acceptable salt thereof.

In some embodiments, the method comprises administering to a cancer patient a therapeutically effective amount of (a) Compound 5 or an enantiomer, diastereomer, or pharmaceutically acceptable salt thereof, (b) rapamycin or a pharmaceutically acceptable salt thereof, and (c) venetoclax or a pharmaceutically acceptable salt thereof.

In some of the above embodiments, the Bcl-2 inhibitor such as venetoclax may be replaced with an IMiD such as pomalidomide, thalidomide, or lenalidomide.

In some embodiments, the method comprises administering to a patient with an immune disorder a therapeutically effective amount of (a) ibrutinib, Compound 3, or Compound 5 and (b) everolimus or rapamycin.

In some embodiments, each of the BTK inhibitor, the mTOR kinase inhibitor, and the Bcl-2 inhibitor or IMiD are administered sequentially, in any order.

In some embodiments, each of the BTK inhibitor, the mTOR kinase inhibitor, and the Bcl-2 inhibitor or IMiD are administered together, e.g., administered in three pharmaceutical compositions concurrently, or as in the same, co-formulated pharmaceutical composition.

In some embodiments, each of the BTK inhibitor, the mTOR kinase inhibitor, and the Bcl-2 inhibitor or IMiD are orally administered to the subject one or more times daily.

In some embodiments, the daily dose of the BTK inhibitor is between 5 mg and 1000 mg. In some embodiments, the daily dose of the mTOR kinase inhibitor is between 0.1 mg and 10 mg. In some embodiments, the daily dose of the IMiD is between 1 mg and 30 mg. In some embodiments, the total daily dose of the BTK inhibitor, the mTOR kinase inhibitor, and the IMiD is 300 mg or less.

In some embodiments, the daily dose of the BTK inhibitor is between 5 mg and 1000 mg. In some embodiments, the daily dose of the mTOR kinase inhibitor is between 0.1 mg and 10 mg. In some embodiments, the daily dose of the Bcl-2 inhibitor is between 10 mg and 1000 mg. In some embodiments, the total daily dose of the BTK inhibitor, the mTOR kinase inhibitor, and the Bcl-2 inhibitor is 500 mg or less.

In some embodiments, the cancer is a B-cell malignancy selected from the group consisting of small lymphocytic lymphoma (SLL), chronic lymphocytic leukemia (CLL), diffuse large B-cell lymphoma (DLBCL), Waldenström Macroglobulinemia (WM), follicular lymphoma (FL), mantle cell lymphoma (MCL), marginal zone lymphoma (MZL), and multiple myeloma (MM).

In some embodiments, the cancer is selected from the group consisting of brain tumors, bladder cancer, stomach cancer, ovarian cancer, pancreatic cancer, breast cancer, head and neck cancer, cervical cancer, endometrial cancer, colorectal cancer, kidney cancer, esophageal cancer, adenocarcinoma, thyroid cancer, bone cancer, skin cancer, colon cancer, female reproductive tract tumors, lymphomas, and testicular cancer.

In some embodiments, the method is effective to reduce average tumor volume of TMD-8 lymphoma xenograft in SCID mice by at least 80%, after 14 days of treatment with at a total daily dose of the BTK inhibitor, the mTOR kinase inhibitor, and the Bcl-2 inhibitor of 20 mg/kg or less.

Another aspect of the invention described herein relates to a pharmaceutical composition comprising a BTK inhibitor, an mTOR kinase inhibitor, a Bcl-2 inhibitor, and a pharmaceutically acceptable carrier.

A further aspect of the invention described herein relates to a pharmaceutical kit comprising a first oral dosage of a BTK inhibitor, a second oral dosage of an mTOR kinase inhibitor, and a third oral dosage form of a Bcl-2 inhibitor or an IMiD. In some embodiments, the pharmaceutical kit further comprises instructions for administering said dosage forms to treat cancer in a subject in need thereof.

A further aspect of the invention described herein relates to a method for treating a cancer or an autoimmune disease, comprising administering to a subject in need thereof a therapeutically effective amount of (a) a Bruton's tyrosine kinase (BTK) inhibitor and (b) a mammalian target of rapamycin (mTOR) kinase inhibitor.

In some embodiments, the method comprises administering to the subject a therapeutically effective amount of (a) ibrutinib or a pharmaceutically acceptable salt thereof and (b) everolimus or a pharmaceutically acceptable salt thereof. In some embodiments, the method comprises administering to the subject a therapeutically effective amount of (a) Compound 3 or a pharmaceutically acceptable salt thereof and (b) everolimus or a pharmaceutically acceptable salt thereof. In some embodiments, the method comprises administering to the subject a therapeutically effective amount of (a) Compound 5 or a pharmaceutically acceptable salt thereof and (b) everolimus or a pharmaceutically acceptable salt thereof.

These and other features, together with the organization and manner of operation thereof, will become apparent from the following detailed description.

BRIEF DESCRIPTION OF THE DRAWINGS

FIG. 12 is a graph showing the antitumor effect of single, double, and triple combination of Compound 3, Compound 12, and Compound 14 or Compound 8 at different dose combinations in the TMD-8 mouse model.

DETAILED DESCRIPTION OF THE INVENTION

Figure 1A:
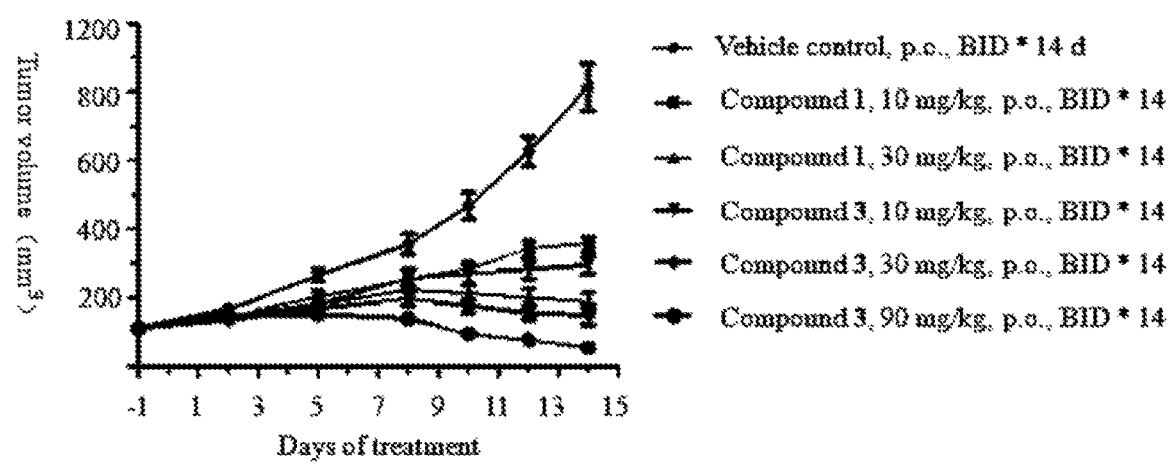
FIG. 1A is a graph showing the antitumor effect of multiple doses of Compounds 1 and 3 on tumor volume in a TMD-8 lymphoma xenograft SCID mouse model. "p.o., BID * 14": by mouth twice a day, for 14 days.

Signaling transduction pathways controlling cell growth, proliferation, survival, and apoptosis are complex and interrelated. Applicant has discovered that concurrent blockade of (i) the BTK-mediated signaling pathway, (ii) the mTOR kinase-mediated signaling pathway, and (iii) the Bcl-2-mediated signaling pathway or a signal transduction pathway targeted by an immunomodulatory drug (IMiD) provides surprisingly superior efficacy in treating cancer, such as hematological malignancies, involving BTK, as compared to monotherapy targeting only one of these pathways.

Applicant has also discovered that concurrent blockade of (i) the BTK-mediated signaling pathway and (ii) the mTOR kinase-mediated signaling pathway provides surprisingly superior efficacy in treating immune disorders, such as autoimmune diseases, inflammation, and hypersensitivity, involving BTK, as compared to monotherapy targeting only either pathway.

In one aspect of the invention, applicant has discovered the unexpected strong synergistic effects in the combined use of BTK, mTOR, and Bcl-2 inhibitors to target the signal transduction mediated by these three cellular proteins. The relationships between signaling pathways are highly complicated. See, e.g., Roschewski et al., "Diffuse large B-cell lymphoma—treatment approaches in the molecular era," Nat Rev Clin Oncol, 2014, 11(1): 12-23, the content of which is herein incorporated by reference in its entirety. The super synergistic effects shown by the present combinations are surprising because not all combinations of anti-cancer drugs have synergistic effects, much less synergistic effects of the magnitude seen with the present combinations. For example, applicant has found that ALK inhibitor ceritinib and BTK inhibitor ibrutinib have no synergistic effect; applicant has also found that JAK1/2 inhibitor ruxolitinib and a BTK inhibitor, or an mTOR inhibitor, or an immunomodulatory drug have no synergistic effect.

However, the "two in one" and "three in one" combination therapies of this invention have been found to be synergistic and superior to monotherapy. The "two in one" pharmaceutical combinations each comprise the use of:

(i) a BTK inhibitor and (ii) an mTOR kinase inhibitor;
(i) a BTK inhibitor and (ii) an IMiD;
(i) a BTK inhibitor and (ii) a TOPK inhibitor;
(i) a BTK inhibitor and (ii) a PI3K inhibitor; or
(i) a TOPK inhibitor and (ii) a PI3K inhibitors.

The "three in one" pharmaceutical combinations each comprise the use of:

(i) a BTK inhibitor, (ii) an mTOR kinase inhibitor, and (iii) an immunomodulatory drug (IMiD);
(i) a BTK inhibitor, (ii) an mTOR kinase inhibitor, and (iii) a Bcl-2 inhibitor; or
(3) a BTK inhibitor, (ii) a PI3K inhibitor, and (iii) a Bcl-2 inhibitor.

Each of these inhibitors is further described below.

Single targeted therapy (monotherapy) requires longer term treatment and often results in drug resistance and disease recurrence over time due to gene mutations in the target (e.g., cancerous) cells. Indeed, resistance to BTK inhibitor ibrutinib has been observed in patients. The combination therapies of this invention circumvent drug resistance because they inhibit potential compensatory pathways in the target cells. The present invention thus brings new hopes to patients with refractory diseases such as drug-resistant cancer. These therapies also have better safety profiles and broader therapeutic windows than single targeted drugs, because the synergistic effects of the drugs in these combination therapies enable a healthcare provider to use the individual drugs at much lower doses, thus reducing side effects of these drugs.

Applicant's studies have showed that the combination therapies of this invention achieved therapeutic efficacy that is as much as 100 times higher than monotherapy, yet at lower individual drug dosages. In various xenograft mouse models, oral gavage administration of a combination of 1/18 Compound 3 (BTK inhibitor)+1/6 everolimus (mTOR inhibitor)+1/6 pomalidomide (IMiD) achieved far better therapeutic effects than each of the three drugs at full doses. A "two in one" combination led to complete tumor regression in the 15-day treatment cycle, and a "three in one" combination led to complete tumor regression in an even shorter treatment cycle (9 days) in the mouse models. Importantly, the tumor did not rebound within 12 days after termination of the treatment, unlike in single targeted therapy.

Applicant has found that the "three in one" pharmaceutical compositions can inhibit up to 95% of tumor cell viability at a BTK inhibitor concentration as low as 10 nM after an incubation time of only 48 hours, and that percentage increases with a longer incubation time (e.g., 72-96 hours). Applicant has also shown that the inhibition of cell viability in vitro by the compositions correlates with the inhibition of tumor growth in vivo by them. It is thus expected that the present compositions can lead to cancer remissions or complete disappearance at an individual drug concentration as low as 10 nM. At present, single targeted therapy or two-pathway combination therapy is effective in inhibiting the growth of tumor cells at the drug concentration of 1,000 nM. For example, venetoclax, a Bcl-2 inhibitor, inhibited TMD-8 tumor cell viability at 1,000 nM, 100 nM and 10 nM, by 37.6%, 18.8% and 11.1%, respectively. A "two in one" pharmaceutical composition of this invention comprised of venetoclax at the same concentrations and Compound 3 (a BTK inhibitor; infra) at 1,000 nM, 100 nM, and 10 nM inhibited TMD-8 cell viability by 85.97%, 79.99% and 65.36%, respectively. A "three in one" pharmaceutical composition comprised of venetoclax at 100 nM, Compound 3 at 1,000 nM, 100 nM, and 10 nM, and PI3K inhibitor at 100 nM inhibited TMD-8 cell viability by 95.56%, 95.30% and 94.62%, respectively. A "three in one" pharmaceutical composition comprised of venetoclax at 100 nM, Compound 3 1,000 nM, 100 nM and 10 nM and mTOR inhibitor everolimus at 100 nM inhibited TMD-8 cell viability by 93.44%, 94.73% and 94.65%, respectively. The significant synergistic effects of the compositions of this invention cannot be inferred from the existing knowledge.

The present combination therapies have been shown not only highly effective in the sensitive TMD-8 tumor model, but also highly effective in the insensitive DoHH2 tumor model and the resistant and refractory WSU-DLCL tumor model. For example, compound EZ-6438 (histone methyltransferase EZH2 inhibitor) inhibited tumor growth in the WSU-DLCL tumor model by oral gavage to mice at the high dose of 480 mg/kg/day according to previous reports (Knutson et al., "Selective inhibition of EZH2 by EPZ-6438 leads to potent antitumor activity in EZH2-mutant non-Hodgkin lymphoma," Mol. Can. Ther, 2014, 13(4):842-54), but the "three in one" combination of this invention is effective at only 21 mg/kg/day for all three drugs combined.

In certain preferred embodiments, the pharmaceutical combinations of the invention comprise (i) a BTK inhibitor, (ii) an mTOR kinase inhibitor, and (iii) an IMiD or a Bcl-2 inhibitor. In in vivo animal models, where the drugs were administered by oral gavage (a route of administration that can avoid uncertainties in pharmacokinetics and more accurately evaluate druggability of an oral pharmaceutical composition than, for example, intraperitoneal injection or intravenous injection), such "three in one" combinations resulted in the complete disappearance of tumor grafts, and no tumor rebound was observed 12 days after treatment ended. Other combinations only inhibited tumor growth, and had to be administered continuously to keep tumor growth at bay. Everolimus monotherapy could result in the complete disappearance of tumor grafts at high doses (3 mg/kg), but tumors quickly rebounded after treatment ended. Thus, the "three in one" pharmaceutical combinations of the present invention not only cause total tumor regression, but it also prevents tumor recurrence.

The individual drugs useful in the present combination therapies are described in further detail below.

BTK Inhibitors

BTK inhibitors useful in the present invention can be those known in the art, including but not limited to
ibrutinib,
acalabrutinib,
BGB-3111 (BeiGene),
spebrutinib,
ONO-4059 (Ono Pharmaceutical),
HM71224 (Hanmi Pharmaceutical),
RN486 (Roche),
4-(4-((4-((3-acrylamidophenyl)amino)-5-fluoropyrimidin-2-yl)amino)phenoxy)-N-methylpicolinamide (CNX-774), and
N-[3-[4,5-dihydro-4-methyl-6-[[4-(4-morpholinylcarbonyl)phenyl]amino]-5-oxopyrazinyl]-2-methylphenyl]-4-(1,1-dimethylethyl)-benzamide (CGI-1746).

They also can be the polyfluorinated compounds described in PCT Publication WO 2015/165279 and U.S. application Ser. No. 15/075,033, filed Mar. 18, 2016, the disclosure of which are incorporated by reference herein in their entireties. Besides small molecules, other chemical entities, such as antisense RNAs, siRNAs, peptidyl inhibitors and antibody inhibitors of BTK can also be used. In some embodiments, the inhibitors bind irreversibly to BTK. In some embodiments, the inhibitors can bind to mutated BTK, such as BTK with a mutation at C481, e.g., a C481S mutation. In some embodiments, inhibitors of other members of the BTK-mediated signaling pathway may be used in lieu of or in addition to BTK inhibitors. For example, inhibitors of Protein Kinase C (PKC) β such as enzastaurin and sotrastaurin can be used as surrogates for a BTK inhibitor.

In certain embodiments, useful BTK inhibitors include those having a structure of one of the following formulae (Formulae I, II, Ia, Ib, IIa, and IIb) or their pharmaceutically acceptable salts thereof, and their individual enantiomers or diastereomers or salts thereof.

Nitrogen atom can form three bonds with other atoms. Any atom other than hydrogen has to be drawn. Hydrogen may or may not be clearly drawn as a typical practice by chemists. For example, R—N means R—$NH_2$, R—NC(=O)—W means R—NH(C=O)—W.

(I)

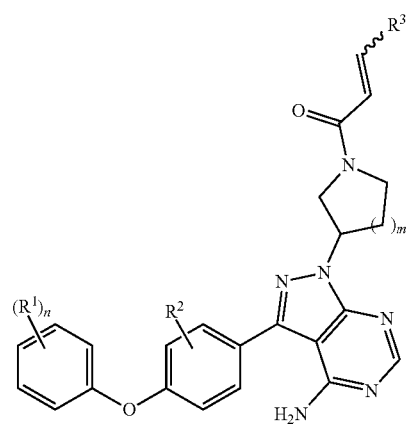

(II)

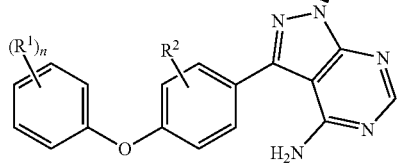

(Ia)

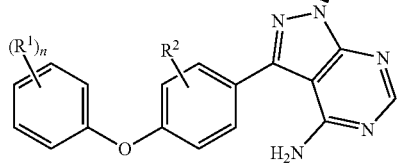

(IIa)

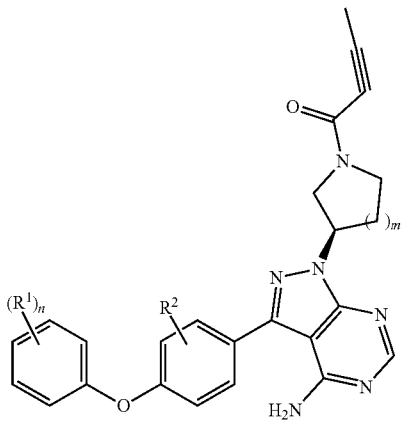

(Ib)

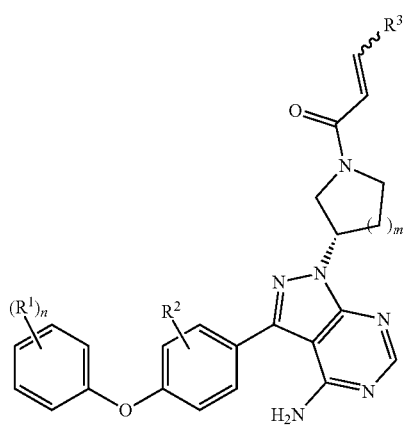

(IIb)

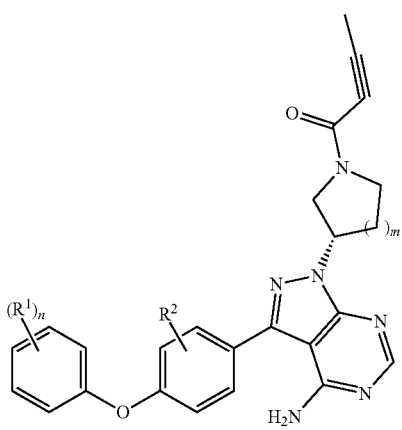

wherein:
each $R^1$ is F;
$R^2$ is F;
$R^3$ is H or D;
n is 1, 2, 3 or 4; and
m is 1 or 2, or an enantiomer or diastereomer thereof, or a pharmaceutically acceptable salt or prodrug thereof.

A compound of the above Formulae may comprise one or more stable isotopes or radio isotopes, including but not limited to, $^2H$, $^3H$, $^{13}C$, $^{14}C$, $^{15}N$, and $^{18}O$. For example, $^1H$, which is at the end of the double bond of the vinyl group in the compound of Formula (I), maybe replaced with $^2H$ to reduce the drug inactivation caused by the oxidation/reduction of double bond.

As used herein, a "prodrug" is a biologically inactive compound that can be metabolized in the body to produce a drug. For example, a prodrug of a BTK inhibitor can be a prodrug at the amino group, for example, an amide, carbamate, or a polyethylene glycol.

As used herein, the term "pharmaceutically acceptable salts" refers to salts formed with acid or base, including, but not limited to, (a) acid addition salts: inorganic acid (e.g., hydrochloric acid, hydrobromic acid, sulfuric acid, phosphoric acid, nitric acid and other organic acids), and organic acid (e.g., acetic acid, oxalic acid, tartaric acid, succinic acid, malic acid, and ascorbic acid); and (b) base addition salts, the formation of metal cations, such as zinc, calcium, sodium, and potassium.

Synthesis Schemes for BTK Inhibitors

A novel method for the synthesis of pyrazolopyrimidine compounds was successfully designed. Representative synthesis schemes are shown below. Unless otherwise specified, in the following reaction schemes and discussion, $R^1$, $R^2$, $R^3$, m, and n have the same meaning as defined above.

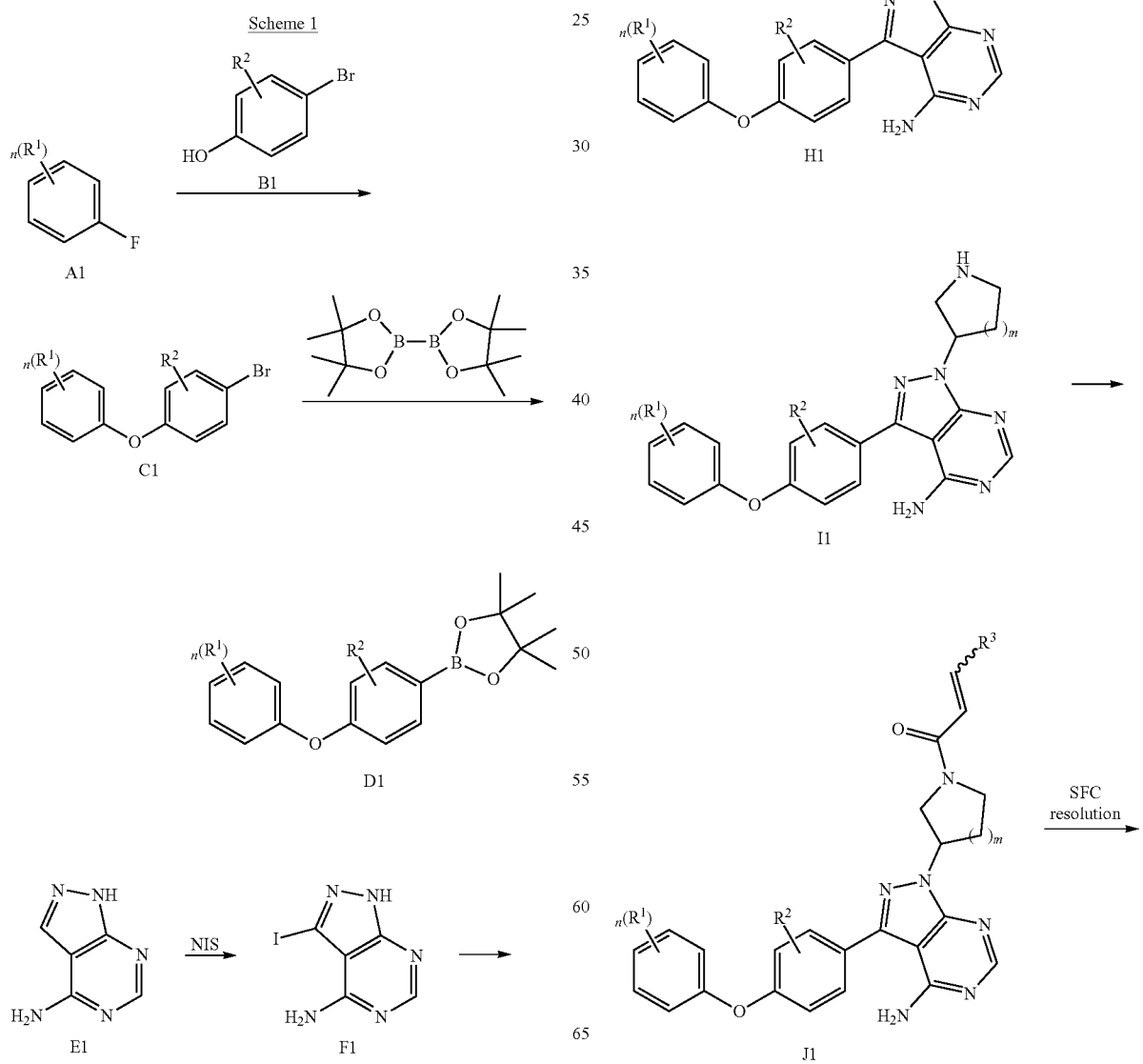

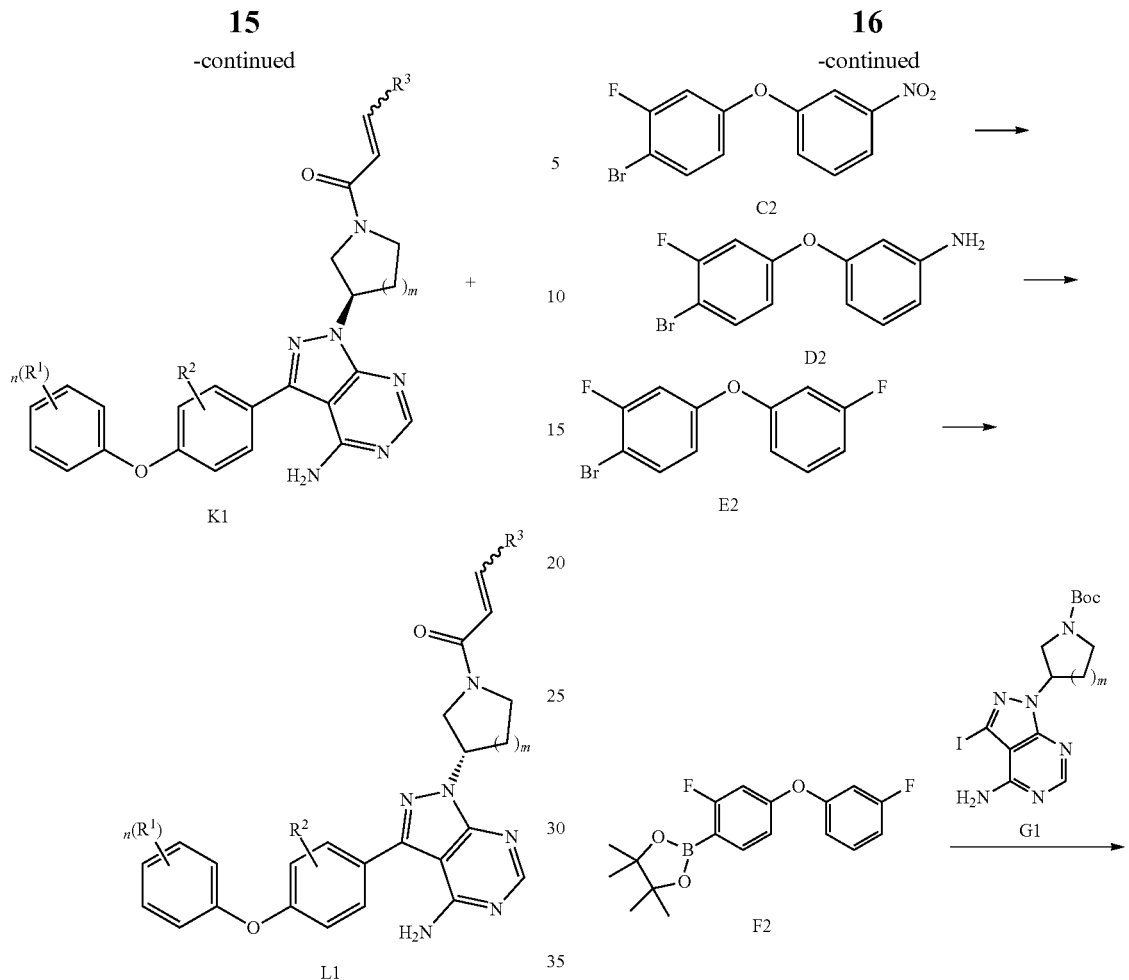

Fluoro-substituted starting material A1 is treated with substituted phenol B1 to generate intermediate C1 under basic condition (e.g., potassium carbonate) in a suitable solvent (e.g., DMF). Intermediate C1 then reacts with bis(pinacolato)diboron to give intermediate D1 with a suitable catalyst (e.g., [1,1'-bis(diphenylphosphino)ferrocene]dichloropalladium(II)) under basic condition (e.g., potassium acetate) in a suitable solvent (e.g., 1,4-dioxane). Iodination of 1H-pyrazolo[3,4-d]pyrimidin-4-amine with NIS forms intermediate F1, followed by Mitsunobu reaction or displacement reaction to furnish intermediate G1. Intermediate G1 is treated with compound D1 above obtained to give intermediate H1 with a suitable catalyst (e.g., Pd-118) under basic condition (e.g., potassium phosphate) in a suitable solvent (e.g., 1,4-dioxane). De-Boc protection of intermediate H1 gives amine I1 under acidic condition. Intermediate I1 is reacted with an electrophilic reagent to form amide J1. If J1 is racemic, optically active compounds K1 and L1 can be obtained by SFC chiral resolution.

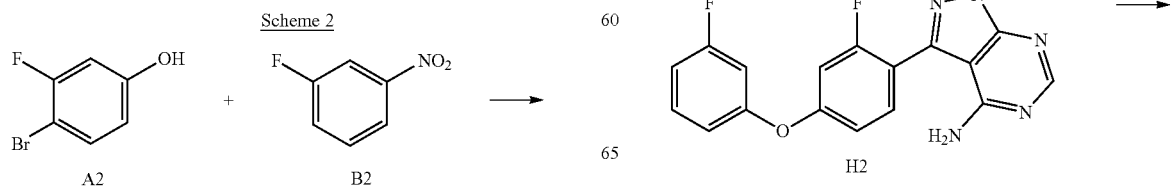

-continued

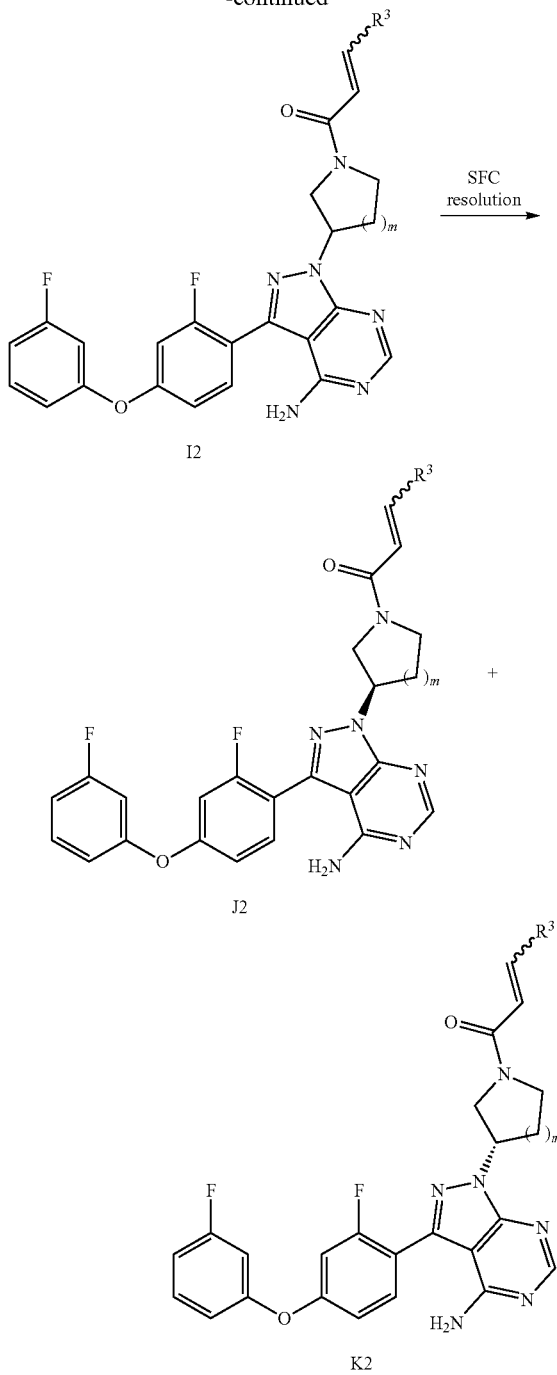

treated with compound F2 above obtained to give intermediate G2 with a suitable catalyst (e.g., Pd-118) under basic condition (e.g., potassium phosphate) in a suitable solvent (e.g., 1,4-dioxane). De-Boc protection of intermediate G2 gives amine H2 under acidic condition. Intermediate H2 is reacted with an electrophilic reagent to form amide I2. If I2 is racemic, optically active compounds J2 and K2 can be obtained by SFC chiral resolution.

Scheme 3

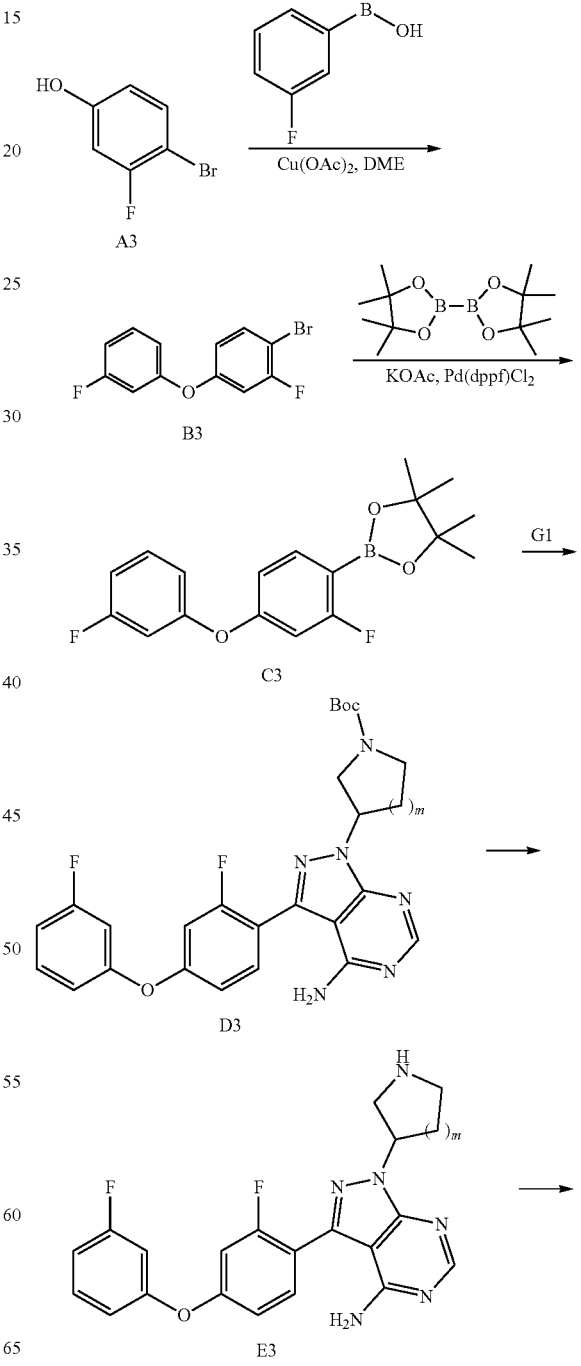

3-fluoro-4-bromophenol reacts with 1-fluoro-3-nitrobenzene to generate intermediate C2 with a base (e.g., potassium carbonate) in a suitable solvent (e.g., DMF). The obtained nitro compound C2 is reduced to the amine D2 with appropriate reducing reagents (e.g., iron powder and ammonium chloride) in appropriate solvents (e.g., ethanol and water), followed by treatment with sodium nitrite and hydrogen fluoride pyridine to generate fluoro-substituted intermediate E2. Intermediate E2 then reacts with bis(pinacolato)diboron to give intermediate F2 with a suitable catalyst (e.g., [1,1'-bis(diphenylphosphino)ferrocene]dichloropalladium (II)) under basic condition (e.g., potassium acetate) in a suitable solvent (e.g., 1,4-dioxane). Intermediate G1 is -continued

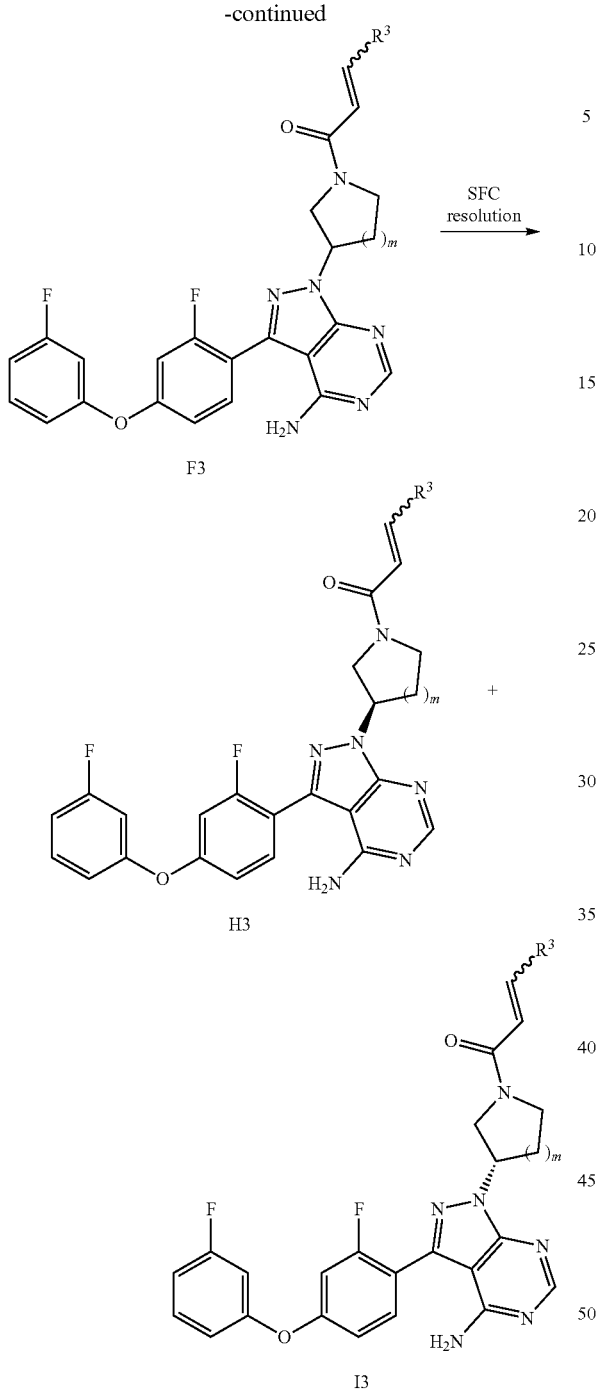

3-fluoro-4-bromophenol reacts with 3-fluorophenylboronic acid to generate intermediate B3 with an appropriate catalyst (e.g., copper acetate). Intermediate B3 then reacts with bis(pinacolato)diboron to give intermediate C3 with a suitable catalyst (e.g., [1,1'-bis(diphenylphosphino)ferrocene]dichloropalladium(II)). Intermediate G1 is treated with compound C3 above obtained to give intermediate D3 with an appropriate catalyst (e.g., [1, 1'-bis(diphenylphosphino) ferrocene]dichloropalladium(II)) under basic condition (e.g., potassium acetate) in a suitable solvent (e.g., 1,4-dioxane). De-Boc protection of intermediate D3 gives amine E3 under acidic condition. Intermediate E3 is reacted with an electrophilic reagent to form amide F3. If F3 is racemic, optically active compounds H3 and I3 can be obtained by SFC chiral resolution.

Scheme 4

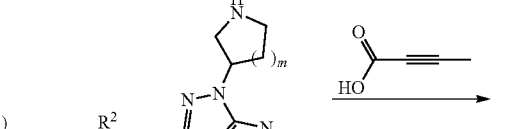

I1

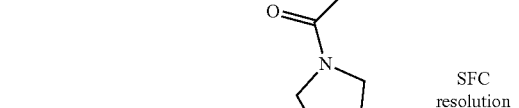

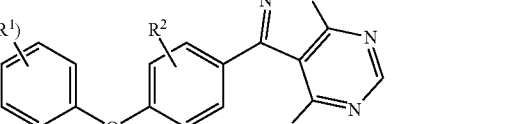

II

IIa

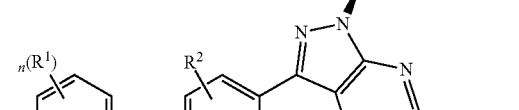

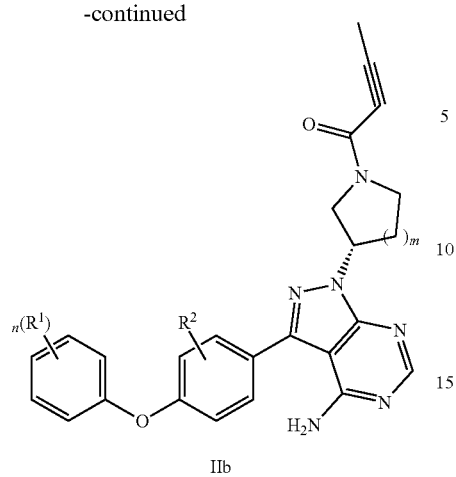
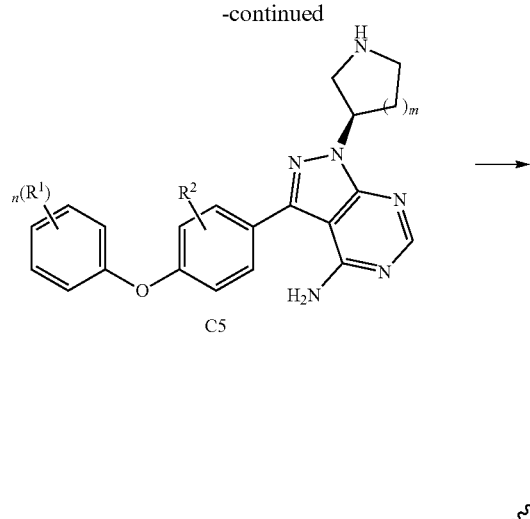

Amine I1 was reacted with but-2-ynoic acid to form amide II. If II is racemic, optically active compounds H3 and I3 could be obtained by SFC chiral resolution.

Scheme 5

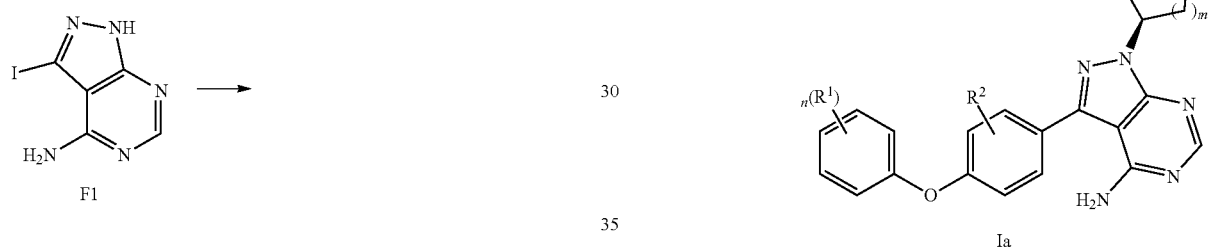

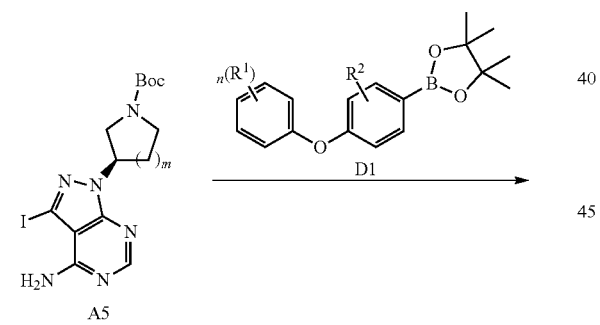

Intermediate A5 was formed via Mitsunobu reaction or displacement reaction from compound F1. A5 was treated with compound D1 above obtained to give intermediate B5 with a suitable catalyst (e.g., Pd-118) under basic condition (e.g., potassium phosphate) in a suitable solvent (e.g., 1,4-dioxane). De-Boc protection of intermediate B5 gave amine C5 under acidic condition. Intermediate C5 was reacted with an electrophilic reagent to form amide Ia.

Scheme 6

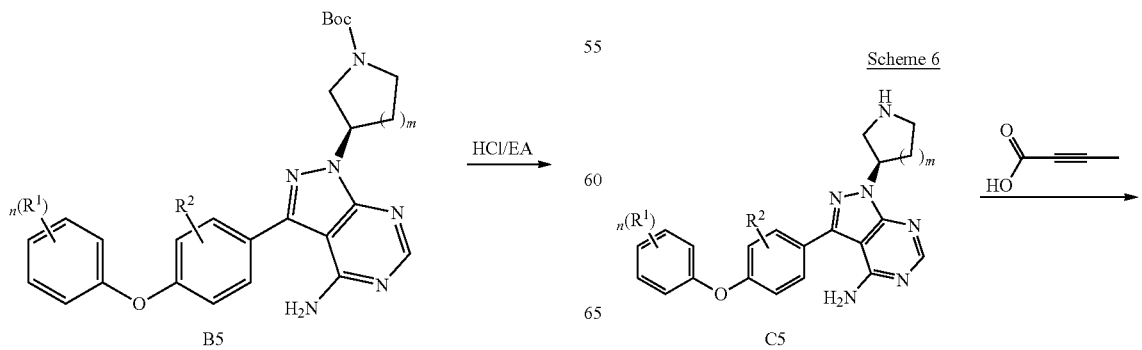

-continued

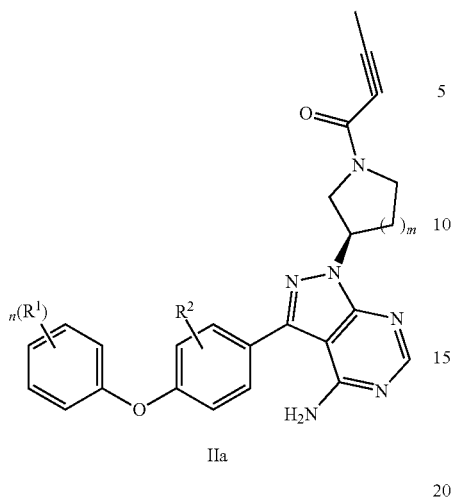
IIa

Amine I1 was reacted with but-2-ynoic acid to form amide IIa.

Table 1 shows the structures and names of these compounds and Compounds 7 and 20.

TABLE 1

| Compound No. | Structure | Name | M + 1 |
|---|---|---|---|
| 1 | 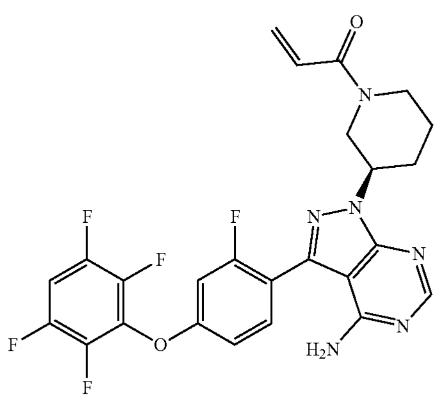 [SMILES: C=CC(=O)N1CCC[C@@H](n2nc(-c3ccc(Oc4c(F)c(F)cc(F)c4F)cc3F)c3c(N)ncnc32)C1] | 1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one | 531 |
| 2 | 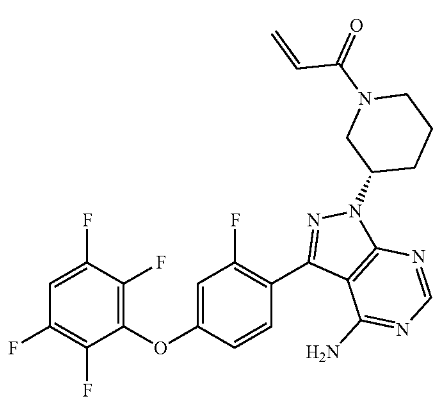 | 1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one | 531 |

TABLE 1-continued

Representative Compounds

| Compound No. | Structure | Name | M + 1 |
|---|---|---|---|
| 3 | 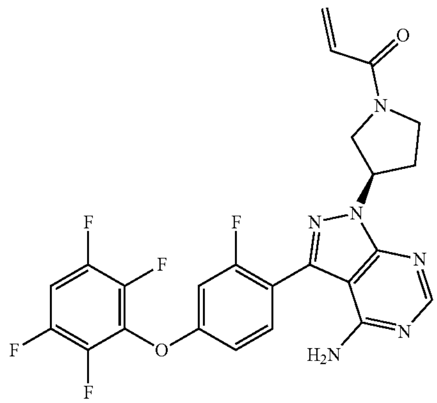 [SMILES: C=CC(=O)N1CC[C@@H](n2nc(-c3ccc(Oc4c(F)c(F)cc(F)c4F)cc3F)c3c(N)ncnc32)C1] | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one | 517 |
| 4 | 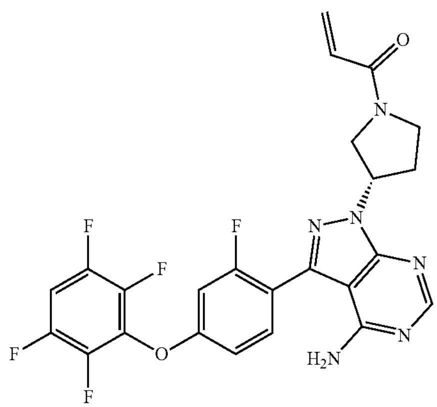 [SMILES: C=CC(=O)N1CC[C@H](n2nc(-c3ccc(Oc4c(F)c(F)cc(F)c4F)cc3F)c3c(N)ncnc32)C1] | 1-((S)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one | 517 |
| 5 | 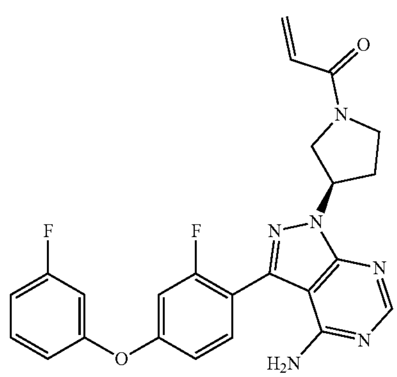 [SMILES: C=CC(=O)N1CC[C@@H](n2nc(-c3ccc(Oc4cccc(F)c4)cc3F)c3c(N)ncnc32)C1] | 1-((R)-3-(4-amino-3-(2-fluoro-4-(3-fluorophenoxy)phenyl)-1H-pyrazolo[3,4-d]pyrimidin-1-yl)pyrrolidin-1-yl)prop-2-en-1-one | 463 |

TABLE 1-continued

Representative Compounds

| Compound No. | Structure | Name | M + 1 |
|---|---|---|---|
| 6 | 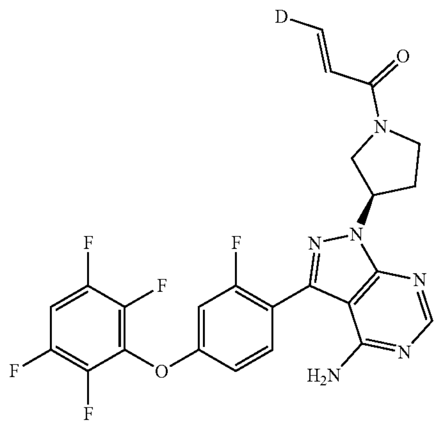 [SMILES: [2H]/C=C/C(=O)N1CC[C@@H](n2nc(-c3ccc(Oc4c(F)c(F)cc(F)c4F)cc3F)c3c(N)ncnc32)C1] | (E)-1-((R)-3-(4-amino-3-(2-fluoro-4-(3-fluorophenoxy)phenyl)-1H-pyrazolo[3,4-d]pyrimidin-1-yl)pyrrolidin-1-yl)-3-deuterium-prop-2-en-1-one | 518 |
| 7 | 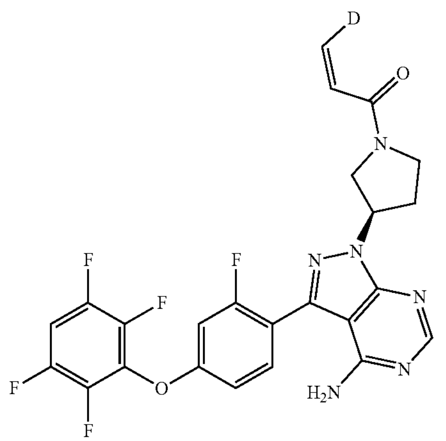 [SMILES: [2H]/C=C\C(=O)N1CC[C@@H](n2nc(-c3ccc(Oc4c(F)c(F)cc(F)c4F)cc3F)c3c(N)ncnc32)C1] | (Z)-1-((R)-3-(4-amino-3-(2-fluoro-4-(3-fluorophenoxy)phenyl)-1H-pyrazolo[3,4-d]pyrimidin-1-yl)pyrrolidin-1-yl)-3-deuterium-prop-2-en-1-one | 518 |
| 20 | 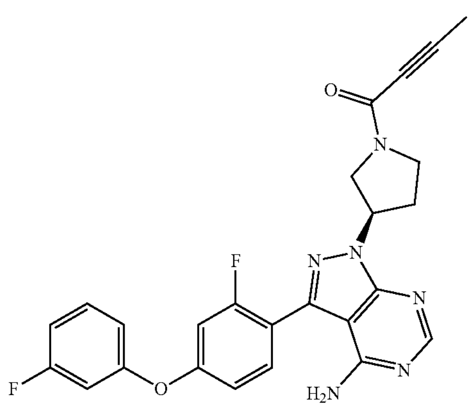 [SMILES: CC#CC(=O)N1CC[C@@H](n2nc(-c3ccc(Oc4cccc(F)c4)cc3F)c3c(N)ncnc32)C1] | 1-((R)-3-(4-amino-3-(2-fluoro-4-(3-fluorophenoxy)phenyl)-1H-pyrazolo[3,4-d]pyrimidin-1-yl)pyrrolidin-1-yl)but-2-yn-1-one | 475 |

Note:
If there are differences between the structure and name, the structure will prevail.

Pharmacokinetic analysis of the Compounds can be performed as descried in Marostica et al., "Population pharmacokinetic model of ibrutinib, a Bruton tyrosine kinase inhibitor, in patients with B cell malignancies," Cancer Chemother Pharmacol, 2015, 75:111-121. The content of this publication is herein incorporated by reference in its entirety.

Toxicity and toxicokinetic (TK) studies of the compounds can be performed by well known methods. Applicant's TK studies showed that the BTK-inhibitory Compounds described herein had better safety profiles than ibrutinib in 28-day rat and dog studies. For example, Compound 3 demonstrated the following advantageous characteristics:

(i) higher no-observed-adverse-effect-level (NOAEL) than ibrutinib;

(ii) 5- to 14-fold higher exposure than ibrutinib at the same dose of 40 mg/kg in rats on day 1;

(iii) when administered to rats at 40 mg/kg, AUC (area under the curve) 13,700 h*ng/mL (male) and 17,300 h*ng/ mL (female), as compared to 1,000 h*ng/mL (male) and 3300 h*ng/mL (female) for ibrutinib at 40 mg/kg (according to U.S. FDA NDA Application No. 205552Orig1s000_pharmacological review);

(iv) when administered to dogs at 15 mg/kg, AUC 3,550 (male) and 2,930 (female) h*ng/mL, as compared to AUC 1,780 (male) and 1,850 (female) h*ng/mL for ibrutinib at 24 mg/kg ((according to U.S. FDA NDA Application No. 205552Orig1s000_pharmacological review);

(v) no significant difference in drug exposure between Day 1 and Day 28; and (vi) no significant difference in drug exposure between male and female.

These characteristics show that Compound 3 has low toxicity, excellent pharmacokinetics, and superior bioavailability when compared to ibrutinib.

mTOR Kinase Inhibitors

The mammalian target of rapamycin (mTOR) is a protein kinase that serves as a key regulator of cell growth, proliferation, metabolism and apoptosis. Inhibitors of mTOR kinase useful in the combination therapy of this invention include but are not limited to everolimus,
rapamycin,
[7-(6-Amino-3-pyridinyl)-2,3-dihydro-1,4-benzoxazepin-4 (5H)-yl][3-fluoro-2-methyl-4-(methylsulfonyl)phenyl]-methanone (XL388),
N-ethyl-N'-[4-[5,6,7,8-tetrahydro-4-[(3 S)-3-methyl-4-morpholinyl]-7-(3-oxetanyl)pyrido[3,4-d]pyrimidin-2-yl]phenyl]-Urea (GDC-0349),
3-(2,4-bis((S)-3-methylmorpholino)pyrido[2,3-d]pyrimidin-7-yl)-N-methylbenzamide (AZD2014),
(5-(2,4-bis((S)-3-methylmorpholino)pyrido[2,3-d]pyrimidin-7-yl)-2-methoxyphenyl)methanol (AZD8055),
GSK105965,
3-(2-aminobenzo[d]oxazol-5-yl)-1-isopropyl-1H-pyrazolo [3,4-d]pyrimidin-4-amine (MLN0128),
temsirolimus,
ridaforolimus,
PI-103,
NVP-BEZ235,
WJD008,
XL765,
SF-1126,
Torin1,
PP242,
PP30,
Ku-0063794,
WYE-354,
WYE-687,
WAY-600,
INK128,
OSI-027, and
pharmaceutically acceptable salts thereof.

In some embodiments, everolimus may be preferred. Everolimus has been approved by the United States Food and Drug Administration for the treatment of breast cancer, pancreatic cancer, renal cell carcinoma, renal angiomyolipoma, and tuberous sclerosis. In addition, everolimus has been used to treat organ transplant rejection at low doses, as organ transplant also activates mTOR. Applicant contemplates that the combination therapy of this invention also can be used in these contexts.

Besides small molecules, other chemical entities, such as antisense RNAs, siRNAs, peptidyl inhibitors and antibody inhibitors of mTOR can also be used. Further, inhibitors of other members of the mTOR-mediated signaling pathway may be used in lieu of or in addition to mTOR inhibitors. For example, inhibitors of phosphoinositide 3-kinase (PI3K) such as BTG226, gedatolisib, apitolisib, omipalisib, dactolisib, duvelisib, and idelalisib can be used in lieu of or in addition to mTOR inhibitors. Inhibitors of Akt (Protein Kinase B) such as 8-[4-(1-aminocyclobutyl)phenyl]-9-phenyl-2H-[1,2,4]triazolo[3,4-f][1,6]naphthyridin-3-one; dihydrochloride (MK-2206) also can be used in lieu of or in addition to mTOR inhibitors.

Immunomodulatory Drugs

Immunomodulatory drugs (IMiDs) are a class of drugs that include thalidomide and its structural and functional analogues. IMiDs possess anti-angiogenic, anti-proliferative and pro-apoptotic properties for cancer cells. IMiDs stimulate T lymphocytes to induce proliferation, cytokine production, and cytotoxicity, thus increasing T cells' anti-cancer activities. IMiDs are useful in treating a variety of inflammatory and autoimmune diseases. IMiDs also are useful in treating neoplastic diseases such as hematologic neoplasms, e.g., multiple myeloma and myelodysplastic syndromes, as well as certain solid tumors. IMiDs such as lenalidomide, pomalidomide, CC-112 (Celgene), and CC-220 (Celgene) have improved potency and reduced side effects compared to thalidomide.

Bcl-2 Inhibitors

B-cell lymphoma 2 protein (Bcl-2) is an important regulator of programmed cell death (apoptosis). Bcl-2 inhibitors useful in this invention include, but are not limited to:

venetoclax,
sabutoclax,
navitoclax,
obatoclax,
4-[4-[[2-(4-Chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide (ABT-737),
N-[4-(2-tert-butylphenyl)sulfonylphenyl]-2,3,4-trihydroxy-5-[(2-propan-2-ylphenyl)methyl]benzamide (TW-37), and
pharmaceutically acceptable salts thereof.

Besides small molecules, other chemical entities, such as antisense RNAs, siRNAs, peptidyl inhibitors and antibody inhibitors of Bcl-2 can also be used. Further, inhibitors of other members of the Bcl-2-mediated signaling pathway may be used in lieu of or in addition to Bcl-2 inhibitors.

Additional Combinations

The combination therapy of this invention may be further combined with other therapeutic agents, such as a TOPK inhibitor (e.g., OTS964 ((R)-9-(4-(1-(dimethylamino)propan-2-yl)phenyl)-8-hydroxy-6-methylthieno[2,3-c] quinolin-4(5H)-one) (Oncotherapy Science)), another tyrosine kinase inhibitor (e.g., axitinib, dasatinib, icotinib), a topoisomerase inhibitor (e.g., topotecan), a sphingosine-1-phosphate receptor agonist (e.g., fingolimod, KRP-203), anti-T cell immunoglobulin (e.g., AtGam), anti-IL-2 receptor antibody (e.g., daclizumab), amides (CTX), ifosfamide (IFO), adriamycin (ADM), daunorubicin (DNR), vincristine (VCR), vinblastine (VBL), etoposide (VP16), vermeer (Vumon), carboplatin (CBP) and methotrexate (MTX) cyclosporin A, tacrolimus, sirolimus, everolimus, azathioprine, brequinar, leflunomide, LEA-29Y, anti-CD3 antibody (e.g., OKT3), aspirin, B7-CD28 blocking molecules (e.g., belatacept, abatacept), CD40-CD154 blocking molecules (anti-CD40 antibodies), acetaminophen, ibuprofen, naproxen, piroxicam, and anti-inflammatory steroids (e.g., prednisolone or dexamethasone).

Diseases

The combination therapies of this invention can treat a variety of conditions in which BTK inhibition is beneficial. These conditions include, without limitation (1) autoimmune diseases, such as chronic lymphocytic thyroiditis, hyperthyroidism, insulin-dependent diabetes mellitus, myasthenia gravis, chronic ulcerative colitis, ulcerative colitis, Crohn's disease, inflammatory bowel disease, pernicious anemia associated with chronic atrophic gastritis, Goodpasture's syndrome, pemphigus vulgaris, pemphigoid, primary biliary cirrhosis, multiple cerebrospinal sclerosis, acute idiopathic neuritis, systemic lupus erythematosus, rheumatoid arthritis, psoriasis, systemic vasculitis, scleroderma, pemphigus, mixed connective tissue disease, multiple sclerosis, autoimmune hemolytic anemia, and autoimmune thyroid disease; (2) hypersensitivity diseases, such as serum sickness, asthma, allergic rhinitis, drug allergy; and (3) inflammatory diseases, such as keratitis, rhinitis, stomatitis, mumps, pharyngitis, tonsillitis, tracheitis, bronchitis, pneumonia, myocarditis, gastritis, gastroenteritis, cholecystitis, and appendicitis. The therapies may also be used in treating rejection in transplantation.

The combination therapies of this invention can also be used to treat a variety of cancer, including hematological malignancies such as B-cell malignancies, e.g., small lymphocytic lymphoma (SLL), prolymphocytic leukemia (PLL), acute lymphocytic leukemia (ALL), chronic lymphocytic leukemia (CLL), Richter's syndrome, diffuse large B-cell lymphoma (DLBCL), Waldenström Macroglobulinemia (WM), follicular lymphoma (FL), multiple myeloma, mantle cell lymphoma (MCL)), marginal zone lymphoma, Hodgkin lymphoma, and non-Hodgkin lymphoma.

In some embodiments, the combination therapies of this invention is used as a first line therapy, to treat patients who have not been treated by another drug for the same condition. In other embodiments, the combination therapy of this invention is used as a second, third, or fourth line therapy, where the patients have been treated for the same condition unsuccessfully (e.g., refractory or relapsed) by another drug, for example, rituximab (which targets CD20 on B cells), CHOP (the cyclophosphamide-hydroxydaunorubicin-oncovin-prednisone therapy), or rituximab plus CHOP (R-CHOP).

Pharmaceutical Compositions and Administration

The individual drugs in the combination therapies of the present invention can be administered separately to the patient, in any order as deemed appropriate for the patient by the healthcare provider. They can also be administered simultaneously; or in a hybrid manner, that is, for example, two of the individual drugs are administered simultaneously, separately from a third drug.

The individual drugs in the combination therapies can also be co-formulated or provided in a pharmaceutical kit. In some embodiments, the co-formulated pharmaceutical composition or the pharmaceutical kit comprises a BTK inhibitor, an mTOR inhibitor, and an IMiD as active ingredients. In other embodiments, the co-formulated pharmaceutical composition or the pharmaceutical kit comprises a BTK inhibitor, an mTOR inhibitor, and a Bcl-2 inhibitor as active ingredients. In other embodiments, the co-formulated pharmaceutical composition or the pharmaceutical kit comprises a BTK inhibitor, a PI3K inhibitor, and a Bcl-2 inhibitor as active ingredients. In other embodiments, the co-formulated pharmaceutical composition or the pharmaceutical kit comprises a BTK inhibitor, a PI3K inhibitor, and an IMiD as active ingredients. In some embodiments, the co-formulated pharmaceutical composition or the pharmaceutical kit comprises two or three compounds selected from BTK inhibitors, mTOR kinase inhibitors, IMiDs, Bcl-2 inhibitors, and PI3K inhibitors as active ingredients.

Also included in the invention are the aforementioned combinations of active ingredients for use in treating diseases where BTK inhibition are beneficial, including, without limitation cancer such as lymphoid malignancies (e.g., B-cell malignancies recited above), and immune disorders such as autoimmune diseases and inflammation. Further included in the invention is the use of the aforementioned combinations of active ingredients in the manufacture of medicament for the treatment of these diseases.

Carriers, excipients and other additives commonly used for pharmaceutical preparations may be used to prepare pharmaceutical compositions containing the active ingredients of the present invention, or pharmaceutically acceptable salts thereof.

The administration forms may be oral dosage forms, such as tablets, pills, capsules, granules, powders, emulsions, syrups, suspensions, liquid preparations; or non-oral dosage forms, such as forms for intravenous, subcutaneous or intramuscular injection, suppository, transdermal implant, or inhalation. Symptoms, age, gender, weight, and other relevant medical information of the patient should be considered in order to properly determine the dosage of the drugs. Generally speaking, for oral administration, daily doses for adult patients of a drug is about 0.001 mg/kg to 100 mg/kg, given in a single dose daily or divided into 2 to 4 subdoses daily; for intravenous administration, daily doses for adult patients is 0.0001 mg/kg to 10 mg/kg, administered once or more times daily.

In the present invention, solid compositions for oral administration may be tablets, capsules, powders, granules and the like. In such solid compositions, one or more active substances with at least one inert excipient (e.g., lactose, mannitol, glucose, hydroxypropylcellulose, microcrystalline cellulose, starch, poly vinyl pyrrolidone, magnesium aluminum silicate, and the like) can be mixed. The compositions may contain inert additives such as lubricants (e.g., magnesium stearate), disintegrating agents (e.g., sodium carboxymethyl starch) and dissolution aids. If necessary, tablets or pills may be coated with appropriate coatings such as a sugar coating or a gastric or enteric coating agent.

The liquid compositions for oral administration include pharmaceutically acceptable emulsions, solutions, aqueous or oily suspensions, syrups, elixirs, and commonly used inert diluent (e.g., purified water, and ethanol). In addition to the inert diluent, the composition may also contain additives such as solubilizing agents, wetting agents, suspending agents, and sweetener, flavoring agents, flavoring agents and preservatives.

Injections for parenteral administration may include sterile aqueous or non-aqueous liquid preparations, suspensions, and emulsions. Diluent aqueous solutions may include distilled water and physiological saline. Non-aqueous diluent solutions may include propylene glycol, polyethylene glycol, vegetable oils, alcohols (e.g., ethanol), and polysorbate 80. Such compositions may further contain isotonic agents, such as preservatives, wetting agents, emulsifying agents, dispersing agents, stabilizing agents, dissolving aids and the like. The compositions can be sterilized by filtration through a bacteria retaining filter, addition of bactericides, or irradiation. In addition, these compositions may be made as sterile solid compositions and dissolved or suspended in sterile water or a sterile solvent for injection prior to use.

Pharmaceutical compositions used for transmucosal administration such as inhalation and nasal absorption can be solid, liquid, or semi-solid state of use, and can be made in accordance with conventional methods. For example, excipients such as lactose, starch, pH adjusting agents, preservatives, surfactants, lubricants, stabilizing and thickening agents and the like can be added. A suitable inhalation or insufflation device can be used. For example, metered dose inhaler devices may be used. A pressurized aerosol spray can also be used with a suitable propellant (e.g., chlorofluoroalkane, hydrofluoroalkane, or a suitable gas such as carbon dioxide).

The following examples are meant to illustrate the methods and materials of the present invention. Suitable modifications and adaptations of the described conditions and parameters normally encountered in the art which are obvious to those skilled in the art are within the spirit and scope of the present invention.

WORKING EXAMPLES

Example 1—Synthesis of BTK Inhibitors

Compound 1 and Compound 2

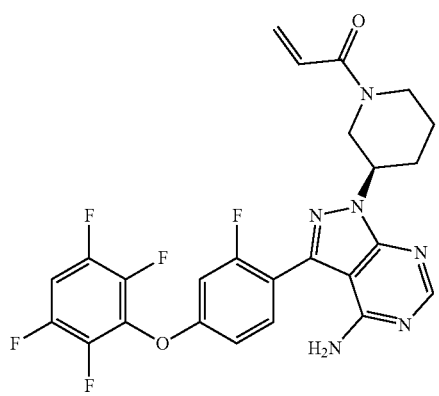 [SMILES: C=CC(=O)N1CCC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one

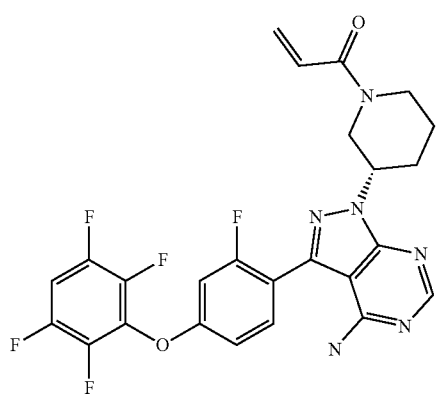 [SMILES: C=CC(=O)N1CCC[C@H](n2nc(-c3ccc(Oc4c(F)c(F)cc(F)c4F)cc3F)c3c(N)ncnc32)C1]

1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one Step A:

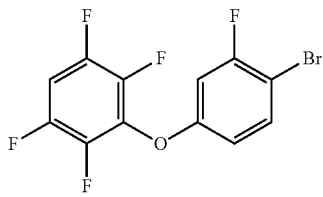

3-(4-bromo-3-fluorophenoxy)-1,2,4,5-tetrafluorobenzene

Potassium carbonate (68.0 g, 492.1 mmol, 2.0 eq.) and the compound 1,2,3,4,5-pentafluorophenyl (49.6 g, 295.3 mmol, 1.2 eq.) was added to a solution of 3-fluoro-4-bromophenol (47.0 g, 246.1 mmol, 1.0 eq.) in DMF (500 mL). The reaction was stirred at 100° C. for 12 hours. Solvent was removed under reduced pressure. The residue was dissolved in ethyl acetate (300 mL), washed with water (100 mL) and brine (100 mL×2). The organic phase was dried over anhydrous sodium sulfate, and concentrated to give the title compound (78 g, yield: 93%).

Step B:

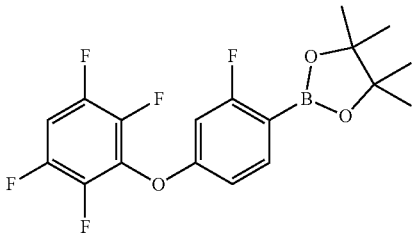 [SMILES: CC1(C)OB(c2ccc(Oc3c(F)c(F)cc(F)c3F)cc2F)OC1(C)C]

2-(2-fluoro-4-(2,3,5,6-tetrafluorophenoxy)phenyl)-4,4,5,5-tetramethyl-1,3,2-dioxaborolane 3-(4-bromo-3-fluorophenoxy)-1,2,4,5-tetrafluorobenzene (73 g, 215.3 mmol, 1.0 eq.), bis pinacolato boronate (65.6 g, 258.4 mmol, 1.2 eq.), potassium acetate (31.6 g, 322.9 mmol, 1.5 eq.) and (dppf)PdCl$_2$ (9.4 g, 12.8 mmol, 0.06 eq.) were added to 1,4-dioxane (1 L). The resulting mixture was stirred at 80° C. for 14 hours under nitrogen. After cooling to room temperature, the reaction mixture was filtered through Celite. The filtrate was concentrated to give the crude product, which was purified by silica gel column chromatography (eluent: petroleum ether) to give the title compound (60 g, yield: 72%).

Step C:

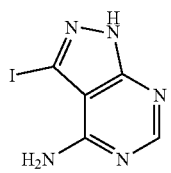

3-iodo-1H-pyrazolo[3,4-d]pyrimidin-4-amine

NIS (250 g, 1.11 mol, 1.5 eq.) was added to a solution of 1H-pyrazolo[3,4-d]pyrimidin-4-amine (100 g, 0.74 mol, 1.0 eq.) in DMF (800 mL). The reaction was stirred at 8085° C. for 16 hours under nitrogen. The reaction mixture was filtered. The filter cake was washed with ethanol (1000 mL×3) to give the title compound (184 g, yield: 95%).

Step D:

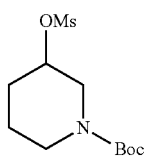

tert-butyl 3-(methylsulfonyloxy)piperidine-1-carboxylate

Triethylamine (15 g, 150 mmol, 3.0 eq.) and methanesulfonyl chloride (6.3 g, 55 mmol, 1.1 eq.) were sequentially added dropwise to a solution of 3-hydroxy-piperidine-1-carboxylate (10.0 g, 50 mmol, 1.0 eq.) in dichloromethane (100 mL) at 0° C. The reaction was stirred at 20° C. for 1 hour, and then quenched with saturated NaHCO$_3$ (100 mL). The resulting mixture was extracted with dichloromethane (200 mL×3). The combined organic phases were dried over anhydrous sodium sulfate, and concentrated under reduced pressure to give the title compound (13 g, yield: 95%).

Step E:

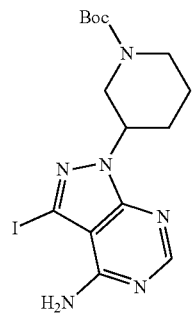 [SMILES: CC(C)(C)OC(=O)N1CCCC(n2nc(I)c3c(N)ncnc32)C1]

tert-butyl 3-(4-amino-3-iodo-1H-pyrazolo[3,4-d]pyrimidin-1-yl)piperidine-1-carboxylate cesium carbonate (20.2 g, 62 mmol, 2.0 eq.) and 3-(methylsulfonyloxy) piperidine-1-carboxylate (13 g, 46.5 mmol, 1.5 eq.) was added to a solution of 3-iodo-1H-pyrazolo[3,4-d]-pyrimidin-4-amine (8.1 g, 31 mmol, 1.0 eq) in DMF (50 mL) at 0° C. The reaction was stirred at 80° C. overnight. After cooling to room temperature, the mixture was filtered through Celite, and concentrated under reduced pressure to give the crude product, which was purified by silica gel column chromatography (eluent: ethyl acetate) to give the title compound (5 g, yield: 25%).

Step F:

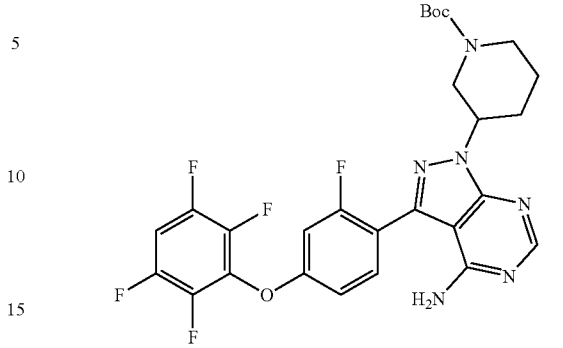

tert-butyl 3-(4-amino-3-(2-fluoro-4-(2,3,5,6-tetrafluorophenoxy)phenyl)-1H-pyrazolo[3,4-d]pyrimidin-1-yl)piperidine-1-carboxylate tert-butyl 3-(4-amino-3-iodo-1H-pyrazolo[3,4-d]pyrimidin-1-yl)piperidine-1-carboxylate (7.6 g, 17.1 mmol, 1.0 eq.), 2-(2-fluoro-4-(2,3,5,6-tetrafluorophenoxy)phenyl)-4,4,5,5-tetramethyl-1,3,2-dioxaborolane (8.6 g, 22.3 mmol, 1.3 eq.), potassium phosphate (7.3 g, 34.2 mmol, 2.0 eq.) and Pd-118 (0.56 g, 0.855 mmol, 0.05 eq.) were added to a mixture of 1,4-dioxane/water (5/1, v/v, 240 mL). The reaction stirred at 60° C. for 12 hours under nitrogen atmosphere. After cooling to room temperature, the reaction mixture was poured into ice water (300 mL) and then extracted with ethyl acetate (100 mL×4). The combined organic phases were dried over anhydrous sodium sulfate, and concentrated to give the crude product, which was purified by silica gel column chromatography separation (eluent: ethyl acetate) to give the title compound (6.8 g, yield: 69%).

Step G:

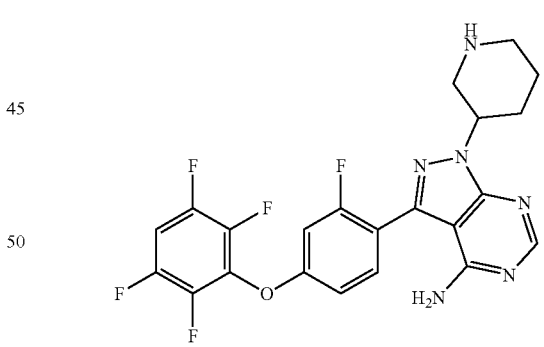

3-(2-fluoro-4-(2,3,5,6-tetrafluorophenoxy)phenyl)-1-(piperidin-3-yl)-1H-pyrazolo[3,4-d]pyrimidin-4-amine HCl/EtOAc (20 mL, 4 mol/L) was added to a solution of tert-butyl 3-(4-amino-3-(2-fluoro-4-(2,3,5,6-tetrafluorophenoxy)phenyl)-1H-pyrazolo[3,4-d]pyrimidin-1-yl)piperidine-1-carboxylate (6.8 g, 11.8 mmol) in ethyl acetate (50 mL) at 0° C. The reaction was stirred at room temperature for 1 hour, and then concentrated to give the title compound hydrochloride (5.2 g, yield: 86%).

Step H:

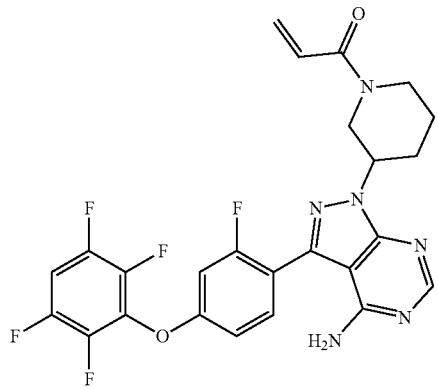 [SMILES: C=CC(=O)N1CCCC(n2nc(-c3ccc(Oc4c(F)c(F)cc(F)c4F)cc3F)c3c(N)ncnc32)C1]

1-(3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one Triethylamine (887 mg, 8.7 mmol, 3.0 eq.) and acryloyl chloride (0.26 g, 2.9 mmol, 1.0 eq.) were sequentially added dropwise to a solution of 3-(2-fluoro-4-(2,3,5,6-tetrafluorophenoxy)phenyl)-1-(piperidin-3-yl)-1H-pyrazolo[3,4-d]pyrimidin-4-amine (1.5 g, 2.9 mmol, 1.0 eq.) in dichloromethane (10 mL) at 0° C. The reaction was stirred at 0° C. for 1 hour, quenched with water (5 mL), diluted with dichloromethane (50 mL), and washed with water (30 mL×2) and saturated brine (30 mL). The organic phase was dried over anhydrous sodium sulfate and concentrated to give the crude product, which was purified by silica gel column chromatography to give the title compound (eluent:petroleum ether:ethyl acetate=1:0~1:1) (0.94 g, yield: 64%).

LC/MS (method: UFLC): RT=3.130 min; m/z=531.1 [M+H]$^+$; Total running time=7.000 min.

$^1$H NMR (400 MHz, DMSO-d$_6$) δ 8.22 (s, 1H), 8.00-7.91 (m, 1H), 7.55-7.46 (m, 1H), 7.27 (dd, J=2.4, 10.8 Hz, 1H), 7.12 (dd, J=2.4, 8.8 Hz, 1H), 6.88-6.65 (m, 1H), 6.13-6.02 (m, 1H), 5.70-5.56 (m, 1H), 4.71-4.65 (m, 1H), 4.54-4.51 (m, 0.5H), 4.20-4.17 (m, 1H), 4.07-4.04 (m, 0.5H), 3.67-3.60 (m, 0.5H), 3.17-3.12 (m, 1H), 2.98-2.94 (m, 0.5H), 2.26-2.21 (m, 1H), 2.11-2.06 (m, 1H), 1.92-1.89 (m, 1H), 1.58-1.54 (m, 1H).

Step I:

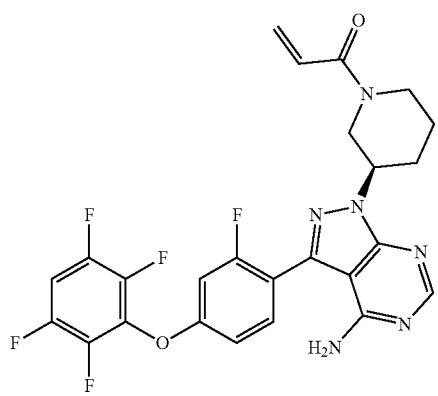 [SMILES: C=CC(=O)N1CCC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one

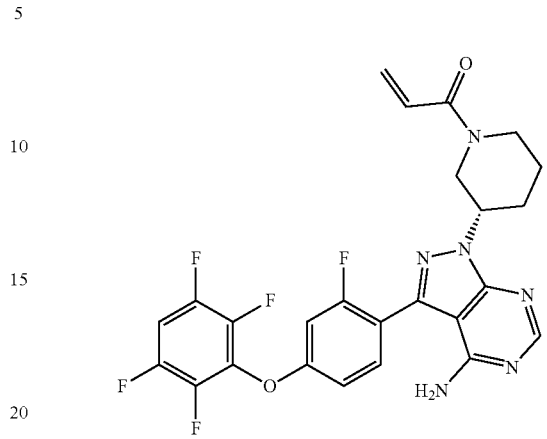

1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one Racemate 1-(3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one (750 mg) was separated by SFC chiral resolution (CO$_2$:C$_2$H$_5$OH (0.2% DEA), v/v, 200 ml/min) to give Compound 1 1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one (280 mg, ee: 100%) and Compound 2 1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one (330 mg, ee: 98%).

Compound 1:

LC/MS (method: UFLC): RT=3.002 min; m/z=531.1 [M+H]$^+$; Total running time=7.000 min.

$^1$H NMR (400 MHz, CDCl$_3$) δ 8.36 (s, 1H), 7.58 (t, J=8.4 Hz, 1H), 7.09-7.04 (m, 1H), 6.94-6.88 (m, 2H), 6.62-6.54 (m, 1H), 6.32-6.25 (m, 1H), 5.73-5.63 (m, 1H), 5.56-5.51 (m, 1H), 4.90-4.85 (m, 1.5H), 4.59-4.56 (m, 0.5H), 4.21-4.17 (m, 0.5H), 4.04-4.01 (m, 0.5H), 3.76-3.71 (m, 0.5H), 3.40-3.35 (m, 0.5H), 3.22-3.15 (m, 0.5H), 2.93-2.87 (m, 0.5H), 2.39-2.27 (m, 2H), 2.04-1.68 (m, 2H).

Compound 2:

LC/MS (method: UFLC): RT=3.006 min; m/z=531.1 [M+H]$^+$; Total running time=7.000 min.

$^1$H NMR (400 MHz, CD$_3$OD) δ 8.24 (s, 1H), 7.62 (t, J=8.4 Hz, 1H), 7.50-7.45 (m, 1H), 7.09-7.01 (m, 2H), 6.85-6.63 (m, 1H), 6.21-6.09 (m, 1H), 5.77-5.61 (m, 1H), 4.63-4.59 (m, 1H), 4.23-4.07 (m, 1.5H), 3.90-3.85 (m, 0.5H), 3.51-3.45 (m, 0.5H), 3.34-3.17 (m, 1.5H), 2.40-2.23 (m, 2H), 2.08-2.05 (m, 1H), 1.75-1.71 (m, 1H).

Compound 3

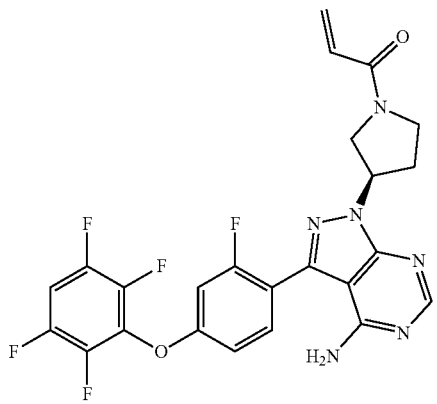

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one Method 1:
Step A:

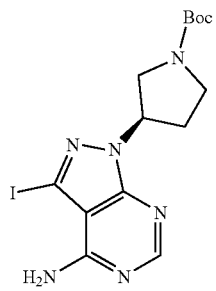 [SMILES: CC(C)(C)OC(=O)N1CC[C@@H](n2nc(I)c3c(N)ncnc32)C1]

(R)-tert-butyl 3-(4-amino-3-iodo-1H-pyrazolo[3,4-d]pyrimidin-1-yl)pyrrolidine-1-carboxylate DIAD (27.6 g, 137.5 mmol, 1.5 eq.) was added dropwise to a mixture of 3-iodo-1H-pyrazolo[3,4-d]pyrimidin-4-amine (24 g, 92 mmol, 1.0 eq.), (S)-tert-butyl 3-hydroxypyrrolidine-1-carboxylate (26 g, 137.5 mmol, 1.5 eq.) and PPh₃ (36 g, 137.5 mmol, 1.5 eq.) in tetrahydrofuran (720 mL) at 0° C. and under nitrogen atmosphere. The reaction was stirred at 0° C. for 1 hour, then stirred overnight at room temperature. After the removal of solvent under reduced pressure, acetonitrile (200 mL) was added to residues. The mixture was stirred at room temperature for 2 hours and filtered. The filter cake was washed with acetonitrile (20 mL) and dried to give the title compound (25 g, yield: 63%).

Step B:

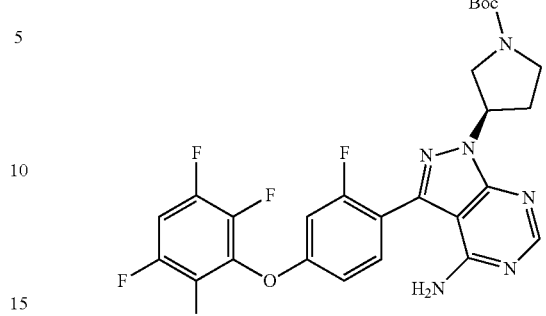

(3R)-tert-butyl 3-(4-amino-3-(2-fluoro-4-(2,3,5,6-tetrafluorophenoxy)phenyl)-1H-pyrazolo[3,4-d]pyrimidin-1-yl)pyrrolidine-1-carboxylate (R)-tert-butyl 3-(4-amino-3-iodo-1H-pyrazolo[3,4-d]pyrimidin-1-yl)pyrrolidine-1-carboxylate (25 g, 58 mmol, 1.0 eq.), 2-(2-fluoro-4-(2,3,5,6-tetrafluorophenoxy)phenyl)-4,4,5,5-tetramethyl-1,3,2-dioxaborolane (30 g, 75.4 mmol, 1.3 eq.), potassium phosphate (25 g, 116 mmol, 2.0 eq.) and Pd-118 (750 mg, 1.16 mmol, 0.02 eq.) were added to a mixture of 1,4-dioxane/water (5/1, v/v, 600 mL). The reaction was stirred at 60° C. overnight under nitrogen atmosphere. After cooling to room temperature, the mixture was filtered through Celite. Filtrate was concentrated under reduced pressure. Water (300 mL) was added to the residue, then extracted with ethyl acetate (300 mL×3). The combined organic phases were dried over anhydrous sodium sulfate, and concentrated to give the title compound (60 g, crude).

Step C:

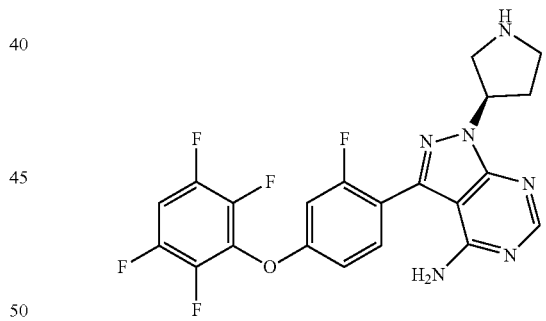

3-(2-fluoro-4-(2,3,5,6-tetrafluorophenoxy)phenyl)-1-((R)-pyrrolidin-3-yl)-1H-pyrazolo[3,4-d]pyrimidin-4-amine HCl/EtOAc (100 mL, 4 mol/L) was added to a solution of (3R)-tert-butyl 3-(4-amino-3-(2-fluoro-4-(2,3,5,6-tetrafluorophenoxy)phenyl)-1H-pyrazolo[3,4-d]pyrimidin-1-yl)pyrrolidine-1-carboxylate (60 g, crude) in ethyl acetate (100 mL) at 0° C. The reaction was stirred at room temperature for 1 hour and concentrated to dryness to give the hydrochloride salt of the title compound. Water (500 mL) was added to the reaction flask, extracted with ethyl acetate (300 mL×3). The aqueous phase was adjusted pH=9, and then extracted with ethyl acetate (300 mL×3). The combined organic phases were dried over anhydrous sodium sulfate, and concentrated under reduced pressure to give the title compound (24 g, two steps yield: 90%).

Step D:

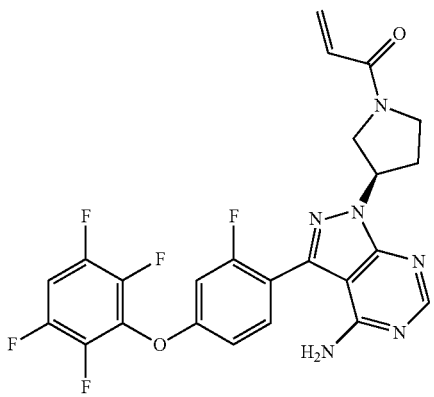 [SMILES: C=CC(=O)N1CC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one NaOH (10%, 94 mL) was added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (. 23.5 g, 50.75 mmol, 1.0 eq) in tetrahydrofuran (470 mL) at −5° C., and then acryloyl chloride (5.97 g, 66 mmol, 1.3 eq.) was added dropwise. The reaction was stirred at −5° C. for 1 hour, quenched with saturated brine (100 mL) and extracted with ethyl acetate (200 mL×3). The combined organic phases were dried over anhydrous sodium sulfate, and concentrated to give the crude product, which was purified by silica gel column chromatography (eluent:petroleum ether:ethyl acetate=1:3~1:1). The product obtained was dissolved in methanol (500 mL) and filtered. Water (1500 mL) was added to the stirred filtrate, stirred for 2 hours and filtered. The filter cake was dried under reduced pressure to give the title compound (16.5 g, yield: 63%).

LC/MS (method: UFLC): RT=3.764 min; m/z=517.0 [M+H]$^+$; Total running time=7.000 min.

$^1$H NMR (400 MHz, CD$_3$OD) δ 8.45 (s, 1H), 7.70 (t, J=8.4 Hz, 1H), 7.55-7.46 (m, 1H), 7.12-7.05 (m, 2H), 6.70-6.55 (m, 1H), 6.33-6.26 (m, 1H), 5.81-5.75 (m, 1H), 4.23-3.83 (m, 5H), 2.68-2.55 (m, 2H).

Method 2:

NaOH (216 mg, 5.40 mmol, 2.5 eq.) was added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (1.0 g, 2.16 mmol, 1.0 eq.) in tetrahydrofuran (50 mL) and water (10 mL) at 0° C., and then a solution of chloropropionyl chloride (288 mg, 2.27 mmol, 1.05 eq.) in tetrahydrofuran (10 mL) was added dropwise. The reaction was stirred at 0° C. for 1 hour, then at 60° C. for 12 hours. After cooling to room temperature, saturated brine (10 mL) was added, and then extracted with ethyl acetate (50 mL×3). The combined organic phases were dried over anhydrous sodium sulfate, and concentrated to give the crude product, which was purified by silica gel column chromatography (eluent:petroleum ether:ethyl acetate=1:3~1:1) to give Compound 3 (0.8 g, yield: 71%).

Method 3:

(R)-1-(3-(4-amino-3-iodo-1H-pyrazolo[3,4-d]pyrimidin-1-yl)pyrrolidin-1-yl)prop-2-en-1-one (100 g, 0.26 mmol, 1.0 eq.), 2-(2-fluoro-4-(2,3,5,6-tetrafluorophenoxy)phenyl)-4,4,5,5-tetramethyl-1,3,2-dioxaborolane (120 mg, 0.31 mmol, 1.2 eq.), sodium carbonate (55 mg, 0.52 mmol, 2.0 eq.) and Pd (PPh$_3$)$_4$ (30 mg, 0.026 mmol, 0.01 eq.) was added to a mixture of 1,4-dioxane/water (5 mL, 1/1, v/v). The reaction was stirred under microwave irradiation at 80° C. for 30 minutes. After cooling to room temperature, reaction mixture was filtered through Celite. The filtrate was concentrated to give the crude product, which was purified by HPLC separation on a (C18 column, mobile phase: acetonitrile/water/0.5% HCl, eluent gradient 10% to 100% (volume ratio)). After the removal of volatile solvent, the desired fraction was lyophilized to give the title compound (38 mg, yield: 28%).

Method 4:

Compound 3 and Compound 4

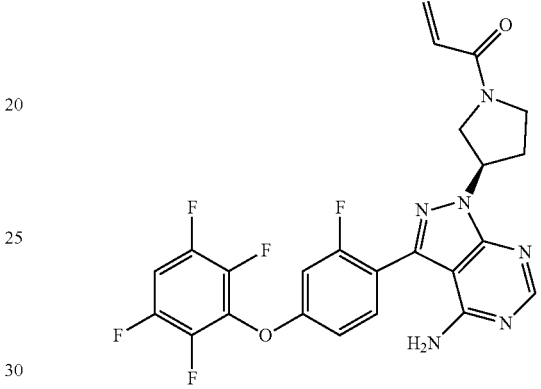

1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one

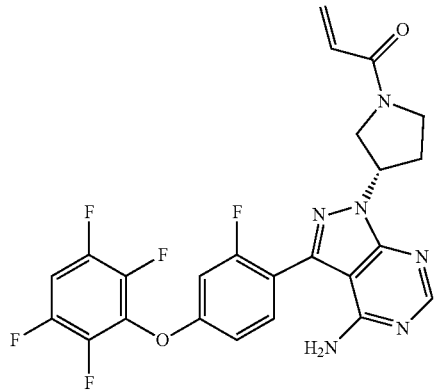 [SMILES: C=CC(=O)N1CC[C@H](n2nc(-c3ccc(Oc4c(F)c(F)cc(F)c4F)cc3F)c3c(N)ncnc32)C1]

1-((S)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one Step A:

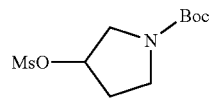

tert-butyl 3-(methylsulfonyloxy)pyrrolidine-1-carboxylate

Triethylamine (35 g, 346 mmol, 2.1 eq.) was added to a solution of 3-hydroxy-pyrrolidine-1-carboxylate (30.0 g, 163 mmol, 1.0 eq.) in dichloromethane (200 mL) at 0° C., and then methyl chloride (36.6 g, 321 mmol, 1.9 eq.) was added dropwise. The reaction was stirred at 0° C. for 3 hours, quenched with water (100 mL), washed with water (20 mL×2) and saturated brine (100 mL). The organic phase was dried over anhydrous sodium sulfate and concentrated to give the title compound (45.6 g, yield: 100%).

Step B:

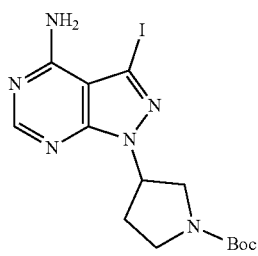 [SMILES: CC(C)(C)OC(=O)N1CCC(n2nc(I)c3c(N)ncnc32)C1]

tert-butyl 3-(4-amino-3-iodo-1H-pyrazolo[3,4-d]pyrimidin-1-yl)pyrrolidine-1-carboxylate Cesium carbonate (37 g, 115 mmol, 3.0 eq.) and the compound 3-iodo-1H-pyrazolo[3,4-d]pyrimidin-4-amine (10 g, 38 mmol, 1.0 eq.) were added to a solution of tert-butyl 3-(methylsulfonyloxy)pyrrolidine-1-carboxylate (35 g, 134 mmol, 3.5 eq.) in DMF (300 mL). The reaction was stirred at 85° C. for 12 h. After cooling to room temperature, the mixture was filtered. The filtrate was concentrated to give the crude product, which was purified by silica gel column chromatography (eluent:petroleum ether:ethyl acetate=1:1) to give the title compound (7.0 g, yield: 44%).

Step C:

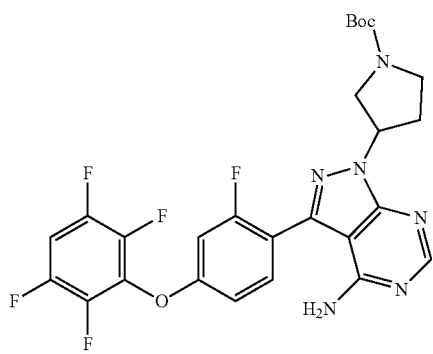 [SMILES: CC(C)(C)OC(=O)N1CCC(n2nc(-c3ccc(Oc4c(F)c(F)cc(F)c4F)cc3F)c3c(N)ncnc32)C1]

tert-butyl 3-(4-amino-3-(2-fluoro-4-(2,3,5,6-tetrafluorophenoxy)phenyl)-1H-pyrazolo[3,4-d]pyrimidin-1-yl)pyrrolidine-1-carboxylate Tert-butyl 3-(4-amino-3-iodo-1H-pyrazolo[3,4-d]pyrimidin-1-yl)pyrrolidine-1-carboxylate (8 g, 18 mmol, 1.0 eq.), 2-(2-fluoro-4-(2,3,5,6-tetrafluorophenoxy)phenyl)-4,4,5,5-tetramethyl-1,3,2-dioxaborolane (10.7 g, 27 mmol, 1.5 eq.), potassium phosphate (7.6 g, 36 mmol, 2.0 eq.) and Pd-118 (1.2 g, 1.8 mmol, 0.1 eq.) were added to a mixture of 1,4-dioxane/water (180 mL, 5/1, v/v). The reaction under nitrogen and stirred at 60° C. for 14 hours. After cooling to room temperature, the reaction mixture was poured into ice water (50 mL) and extracted with ethyl acetate (100 mL×3). The combined organic phases were dried over anhydrous sodium sulfate and concentrated to give the crude product, which was purified by silica gel column chromatography (eluent:ethyl acetate:petroleum ether=1:1) to give the title compound (2.5 g, yield: 25%).

Step D:

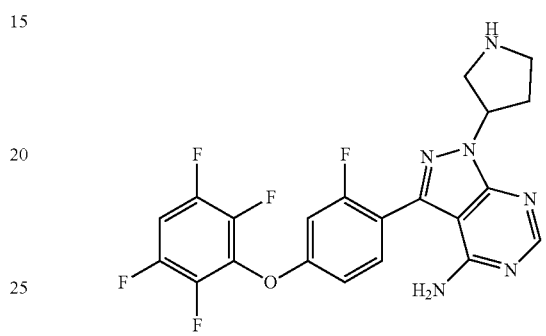

3-(2-fluoro-4-(2,3,5,6-tetrafluorophenoxy)phenyl)-1-(pyrrolidin-3-yl)-1H-pyrazolo[3,4-d]pyrimidin-4-amine HCl/EtOAc (20 mL, 4 mol/L) was added to a solution of tert-butyl 3-(4-amino-3-(2-fluoro-4-(2,3,5,6-tetrafluorophenoxy)phenyl)-1H-pyrazolo[3,4-d]pyrimidin-1-yl)pyrrolidine-1-carboxylate (2.5 g, 4.4 mmol) in dichloromethane (20 mL) at 0° C. The reaction was stirred for 1 hour at room temperature, and then concentrated to under pressure give the title compound hydrochloride (2.2 g, yield: 100%).

Step E:

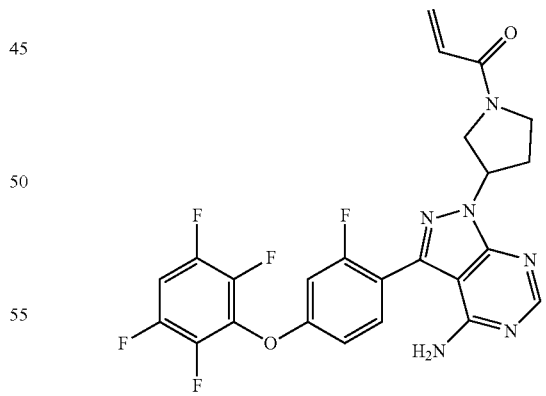

1-(3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one Triethylamine (1.4 g, 12.8 mmol, 3.0 eq.) was added to a solution of 3-(2-fluoro-4-(2,3,5,6-tetrafluorophenoxy)phenyl)-1-(pyrrolidin-3-yl)-1H-pyrazolo[3,4-d]pyrimidin-4- amine (2.2 g, 4.4 mmol, 1.0 eq.) in dichloromethane (50 mL), then acryloyl chloride (0.38 g, 4.2 mmol, 0.95 eq.) was added dropwise at 0° C. The reaction was stirred at 0° C. for 1 hour and quenched with water (30 mL). The aqueous phase was extracted with methylene chloride (30 mL×3). The combined organic phases were dried over anhydrous sodium sulfate and concentrated to give the crude product, which was purified by silica gel column chromatography (eluent: ethyl acetate) to give the title compound (1.0 g, yield: 45%).

LC/MS (method: UFLC): RT=2.810 min; m/z=517.1 [M+H]⁺; Total running time=7.000 min.

Step F:

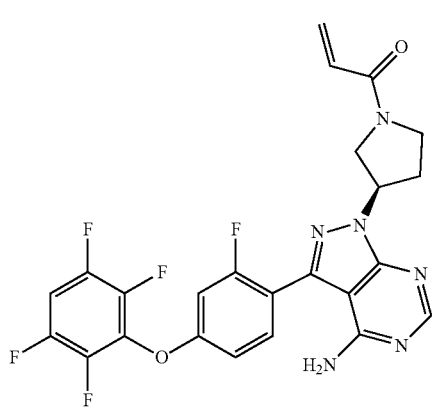 [SMILES: C=CC(=O)N1CC[C@@H](n2nc(-c3ccc(Oc4c(F)c(F)cc(F)c4F)cc3F)c3c(N)ncnc32)C1]

1-((R)-3-(4-amino-3-(2-fluoro-4-(2,3,5,6-tetrafluoro-phenoxy)phenyl)-1H-pyrazolo[3,4-d]pyrimidin-1-yl) pyrrolidin-1-yl)prop-2-en-1-one

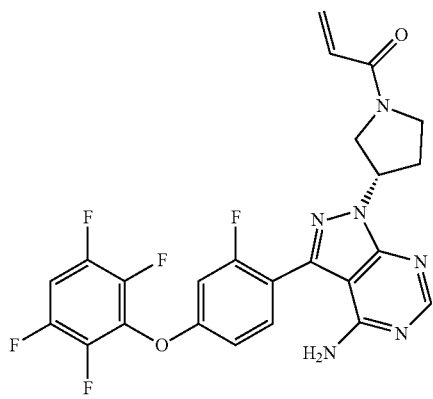 [SMILES: C=CC(=O)N1CC[C@H](n2nc(-c3ccc(Oc4c(F)c(F)cc(F)c4F)cc3F)c3c(N)ncnc32)C1]

1-((S)-3-(4-amino-3-(2-fluoro-4-(2,3,5,6-tetrafluoro-phenoxy)phenyl)-1H-pyrazolo[3,4-d]pyrimidin-1-yl) pyrrolidin-1-yl)prop-2-en-1-one Racemate 1-(3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one was separated by SFC chiral resolution to give Compound 3 (280 mg) and Compound 4 (320 mg).

Compound 4:
LC/MS (method: UFLC): RT=2.808 min; m/z=517.1 [M+H]⁺; Total running time=7.000 min.

Compound 5

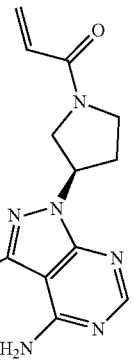

1-((R)-3-(4-amino-3-(2-fluoro-4-(3-fluorophenoxy) phenyl)-1H-pyrazolo[3,4-d]pyrimidin-1-yl)pyrrolidin-1-yl)prop-2-en-1-one Step A:

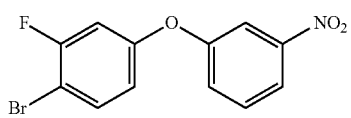 [SMILES: Nc1cccc(Oc2ccc(Br)c(F)c2)c1]

1-bromo-2-fluoro-4-(3-nitrophenoxy)benzene 1-fluoro-3-nitrobenzene (29.6 g, 210 mmol, 1.0 eq.) and potassium carbonate (58 g, 420 mmol, 2.0 eq.) were added to a solution of 3-fluoro-4-bromophenol (40 g, 210 mmol, 1.0 eq.) in DMF (400 mL). The reaction was stirred at 90° C. for 12 hours under nitrogen atmosphere. After the removal of the solvent under reduced pressure, water (300 mL) was added to the residue, and then extracted with ethyl acetate (300 mL×3). The combined organic phases were dried over anhydrous sodium sulfate and concentrated to give the title compound (65 g, yield: 100%).

Step B:

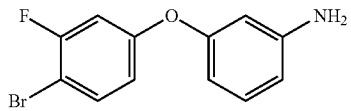

3-(4-bromo-3-fluorophenoxy)benzenamine

Chloride ammonium (28 g, 525 mmol, 2.5 eq.) and iron powder (58.8 g, 1.05 mol, 5.0 eq.) was added to a solution of 1-bromo-2-fluoro-4-(3-nitrophenoxy)benzene (65 g, 210 mmol, 1.0 eq.) in ethanol (300 mL) and water (60 mL). The reaction solution was refluxed for 12 hours under nitrogen. After cooling to room temperature, the mixture was filtered through Celite. The filtrate concentrated to give the crude product, which was purified by HPLC (C18 reverse phase column, mobile phase: acetonitrile/water/0.7% NH₄HCO₃, eluent gradient 10%-100% (volume ratio)). After the removal of volatile solvent, the desired fraction was lyophilized to give the title compound (19 g, yield: 23%).

Step C:

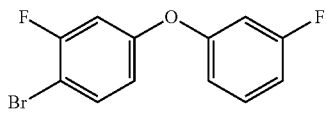 [SMILES: Fc1cccc(Oc2ccc(Br)c(F)c2)c1]

1-bromo-2-fluoro-4-(3-fluorophenoxy)benzene 3-(4-bromo-3-fluorophenoxy)benzenamine (9 g, 32 mmol, 1.0 eq.) was added to pyridine-hydrogen fluoride solution (30 mL) in portions at −10° C. The resulting reaction mixture was stirred at 0° C. for 30 minutes, cooled to −10° C., and then sodium nitrite (2.42 g, 35 mmol, 1.1 eq.) was added portion-wise. The reaction was stirred at 20° C. for 30 minutes, then at 60° C. for 14 hours. After cooling to room temperature, the mixture was poured into ice-ethanol (50 mL), diluted with saturated solution of $NaHCO_3$ (50 mL), and then extracted with ethyl acetate (50 mL×3). The combined organic phases were dried over anhydrous sodium sulfate and concentrated to give the crude product, which was purified by silica gel column chromatography (eluent: petroleum ether) to give the title compound (5.8 g, yield: 64%).

Step D:

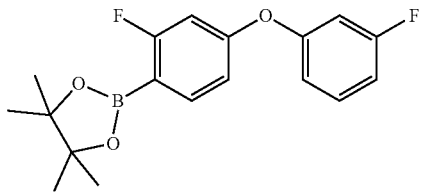 [SMILES: CC1(C)OB(c2ccc(Oc3cccc(F)c3)cc2F)OC1(C)C]

2-(2-fluoro-4-(3-fluorophenoxy)phenyl)-4,4,5,5-tetramethyl-1,3,2-dioxaborolane 1-bromo-2-fluoro-4-(3-fluorophenoxy) benzene (5.8 g, 20 mmol, 1.0 eq.), bis pinacolato boronate (6.1 g, 24 mmol, 1.2 eq.), potassium acetate (3.9 g, 40 mmol, 2.0 eq.) and [1,1'-bis(diphenylphosphino) ferrocene] dichloropalladium (0.89 g, 1.2 mmol, 0.06 eq.) were dissolved in 1,4-dioxane (100 mL). The reaction mixture was stirred at 85° C. for 14 hours under nitrogen atmosphere. After cooling to room temperature, the mixture was filtered through Celite. The filtrate was concentrated to give the crude product, which was purified by silica gel column chromatography (eluent: petroleum ether) to give the title compound (6.5 g, yield: 100%).

Step E:

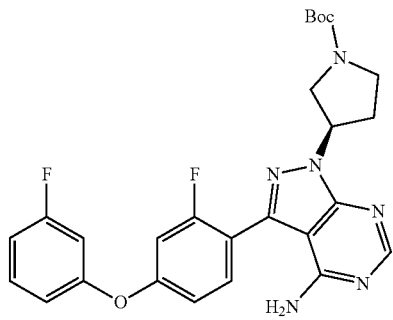 [SMILES: CC(C)(C)OC(=O)N1CC[C@@H](n2nc(-c3ccc(Oc4cccc(F)c4)cc3F)c3c(N)ncnc32)C1]

(3R)-tert-butyl 3-(4-amino-3-(2-fluoro-4-(3-fluorophenoxy)phenyl)-1H-pyrazolo[3,4-d]pyrimidin-1-yl)pyrrolidine-1-carboxylate (R)-tert-butyl 3-(4-amino-3-iodo-1H-pyrazolo[3,4-d]pyrimidin-1-yl)pyrrolidine-1-carboxylate (6.5 g, 15.0 mmol, 1.0 eq.), 2-(2-fluoro-4-(3-fluorophenoxy)phenyl)-4,4,5,5-tetramethyl-1,3,2-dioxaborolane (6.5 g, 19.6 mmol, 1.3 eq.), potassium phosphate (6.4 g, 30.1 mmol, 2.0 eq.) and Pd-118 (0.25 g, 0.39 mmol, 0.01 eq.) were added to a mixture of 1,4-dioxane/water (16 mL, 1/1, v/v). The resulting mixture was stirred at 85° C. for 12 hours under nitrogen atmosphere. After cooling to room temperature, the reaction mixture was diluted with water (50 mL), and then extracted with ethyl acetate (100 mL×3). The combined organic phases were dried over anhydrous sodium sulfate and concentrated to give the crude product, which was purified by silica gel column chromatography (eluent: ethyl acetate) to give the title compound (4.2 g, yield: 55%).

Step F:

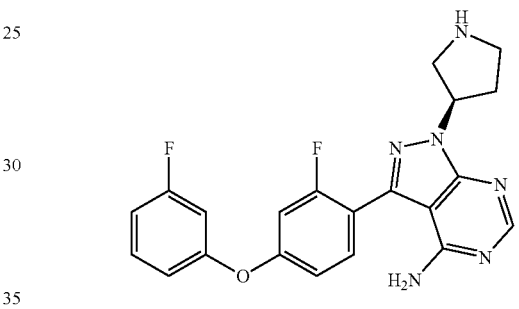

3-(2-fluoro-4-(3-fluorophenoxy)phenyl)-1-((R)-pyrrolidin-3-yl)-1H-pyrazolo[3,4-d]pyrimidin-4-amine HCl/EA (10 mL, 4 mol/L) was added to a solution of (3R)-tert-butyl 3-(4-amino-3-(2-fluoro-4-(3-fluorophenoxy)phenyl)-1H-pyrazolo[3,4-d]pyrimidin-1-yl)pyrrolidine-1-carboxylate (4.2 g, 8.27 mmol) in dichloromethane (15 mL) at 0° C. The reaction was stirred for 1 hour at room temperature, and then concentrated under reduced pressure to give the title compound hydrochloride (3.7 g, yield: 92%).

Step G:

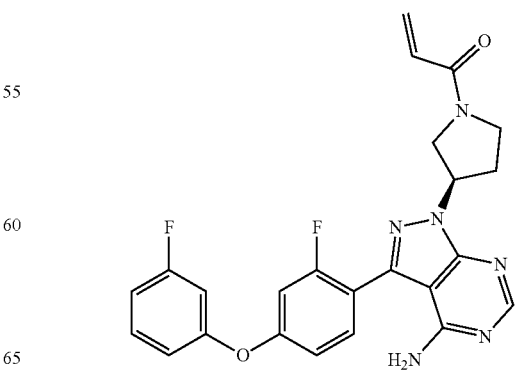

1-((R)-3-(4-amino-3-(2-fluoro-4-(3-fluorophenoxy)phenyl)-1H-pyrazolo[3,4-d]pyrimidin-1-yl)pyrrolidin-1-yl)prop-2-en-1-one Sodium hydroxide (10%, 15.3 mL) and acryloyl chloride (0.67 g, 7.44 mmol, 0.9 eq.) were sequentially added dropwise to a solution of 3-(2-fluoro-4-(3-fluorophenoxy)phenyl)-1-((R)-pyrrolidin-3-yl)-1H-pyrazolo[3,4-d]pyrimidin-4-amine (3.7 g, 8.27 mmol, 1.0 eq.) in tetrahydrofuran (20 mL) at 0° C. The reaction was stirred at room temperature for 10 minutes, quenched with saturated NaHCO₃ (20 mL), and extracted with dichloromethane (30 mL×3). The combined organic phases were dried over anhydrous sodium sulfate and concentrated to give the crude product, which was purified by silica gel column chromatography (eluent: petroleum ether:ethyl acetate=1:0 to 1:1) to give the title compound (2.5 g, yield: 65%).

LC/MS (method: UFLC): RT=3.178 min; m/z=463.0 [M+H]⁺; Total running time=7.000 min.

¹H NMR (400 MHz, CDCl₃) δ 8.36 (s, 1H), 7.53-7.49 (m, 1H), 7.40-7.35 (m, 1H), 6.95-6.81 (m, 4H), 6.41-6.39 (m, 2H), 5.69-5.55 (m, 3H), 4.14-3.98 (m, 3H), 3.78-3.72 (m, 1H), 2.71-2.54 (m, 2H).

Compound 6

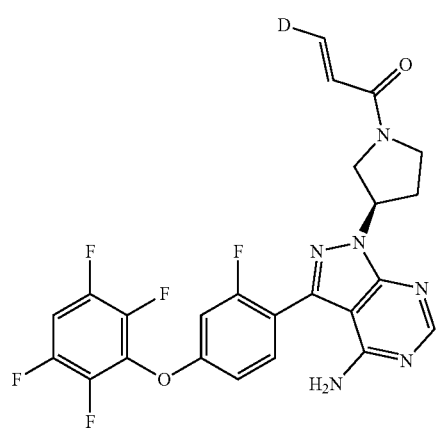 [SMILES: [2H]/C=C/C(=O)N1CC[C@@H](n2nc(-c3ccc(Oc4c(F)c(F)cc(F)c4F)cc3F)c3c(N)ncnc32)C1]

(E)-1-((R)-3-(4-amino-3-(2-fluoro-4-(3-fluorophenoxy)phenyl)-1H-pyrazolo[3,4-d]pyrimidin-1-yl)pyrrolidin-1-yl)-3-deuterium-prop-2-en-1-one Step A:

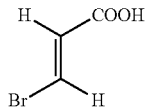

(E)-3-bromoacrylic Acid

A mixture of propiolic acid (1 g, 14.28 mmol, 1.0 eq.) and HBr (40% aqueous solution, 1.7 mL, 0.88 eq.) was stirred overnight at 140° C. Solvent was distilled off under reduced pressure. The obtained crude product was crystallized from water (4 mL×3) to give the title compound (0.76 g, yield: 35%).

¹H NMR (400 MHz, CDCl₃) δ 7.76 (d, J=14 Hz, 1H), 6.55 (d, J=14 Hz, 1H).

Step B:

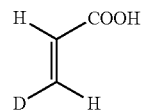

(E)-3-deuteriumacrylic Acid

Na—Hg (6 g, 49.67 mmol, 2.5 eq.) was added to a solution of (E)-3-bromoacrylic acid (3 g, 19.87 mmol, 1.0 eq.) in D₂O (30 mL) at 0–5° C. The reaction was stirred at room temperature for 36 hours. The aqueous phase was adjusted pH=5 with 1M hydrochloric acid, and then extracted with diethyl ether (20 mL×5). The combined organic phases were dried over anhydrous sodium sulfate and concentrated under reduced pressure to give the title compound (0.52 g, yield: 36%).

¹H NMR (400 MHz, CDCl₃) δ 7.76 (d, J=17.2 Hz, 1H), 6.55 (d, J=17.2 Hz, 1H).

Step C:

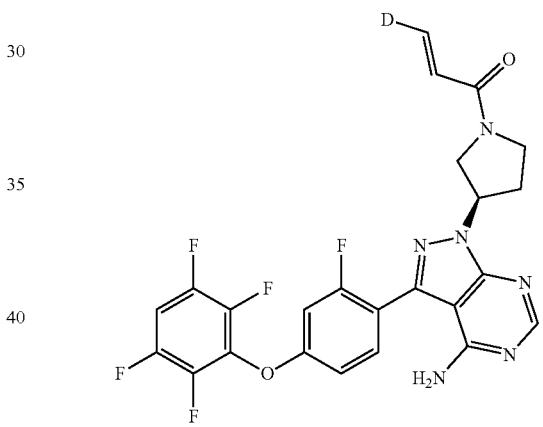

(E)-1-((R)-3-(4-amino-3-(2-fluoro-4-(3-fluorophenoxy)phenyl)-1H-pyrazolo[3,4-d]pyrimidin-1-yl)pyrrolidin-1-yl)-3-deuterium-prop-2-en-1-one (E)-3-deuteriumacrylic acid (76 mg, 1.08 mmol, 1.0 eq.), HATU (530 mg, 1.40 mmol, 1.3 eq.) and N, N-diisopropylethylamine (419 mg, 3.24 mmol, 3.0 eq.) were added to a solution of 3-(2-fluoro-4-(2,3,5,6-tetrafluorophenoxy)phenyl)-1-((R)-pyrrolidin-3-yl)-1H-pyrazolo[3,4-d]pyrimidin-4-amine (500 mg, 1.08 mmol, 1.0 eq.) in dichloromethane (50 mL). The reaction was stirred at room temperature for 12 hours, and concentrated to give the crude product, which was purified by HPLC-separation (instrument: LC 8A & Gilson 215, fraction collector column: Synergi Max-RP 150*30 mm*4 u, mobile phase A: water (0.5% HCl), mobile phase B: acetonitrile, flow rate: 30 mL/min, gradient B: 36%~37%, 0~17 minutes). After the removal of volatile solvent, the desired fraction was lyophilized to give the title compound hydrochloride (76 mg, yield: 13%).

LC/MS (method: UFLC): RT=2.765 min; m/z=518.1 [M+H]⁺; Total running time=7.000 min.

¹H NMR (400 MHz, CD₃OD) δ 8.41 (s, 1H), 7.66 (t, J=8.4 Hz, 1H), 7.51-7.44 (m, 1H), 7.09-7.01 (m, 2H), 6.66-6.56 (m, 1H), 6.28-6.23 (m, 1H), 5.75-5.66 (m, 1H), 4.19-4.16 (m, 1H), 4.06-4.02 (m, 1.5H), 3.89-3.85 (m, 1H), 3.78-3.72 (m, 0.5H), 2.63-2.49 (m, 2H).

Compound 7

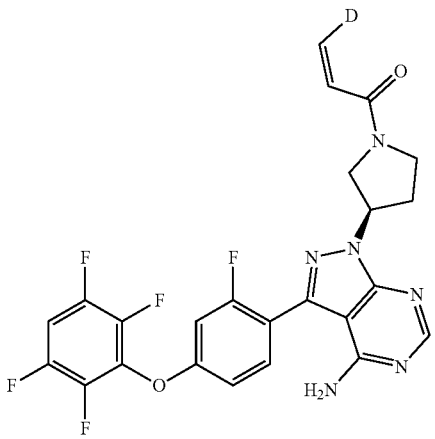 [SMILES: [2H]/C=C\C(=O)N1CC[C@@H](n2nc(-c3ccc(Oc4c(F)c(F)cc(F)c4F)cc3F)c3c(N)ncnc32)C1]

(Z)-1-((R)-3-(4-amino-3-(2-fluoro-4-(3-fluorophe-noxy)phenyl)-1H-pyrazolo[3,4-d]pyrimidin-1-yl)pyrrolidin-1-yl)-3-deuterium-prop-2-en-1-one Step A:

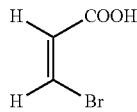

(Z)-3-bromoacrylic Acid

A mixture of propiolic acid (1 g, 14.28 mmol, 1.0 eq.) and HBr (40% aqueous solution, 1.7 mL, 0.88 eq.) was stirred overnight at 55° C. Solvent was distilled off under reduced pressure. The obtained crude product was crystallized from petroleum ether (4 mL×3) to give the title compound (0.3 g, yield: 14%).

¹H NMR (400 MHz, CDCl₃) δ 7.16 (d, J=8.4 Hz, 1H), 6.67 (d, J=8.4 Hz, 1H).

Step B:

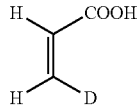

(Z)-3-deuteriumacrylic Acid

Na—Hg (6 g, 49.67 mmol, 2.5 eq.) was added to a solution of (Z)-3-bromoacrylic acid (3 g, 19.87 mmol, 1.0 eq.) in D₂O (30 mL) at 0~5° C. The reaction was stirred at room temperature for 36 hours. The aqueous phase was adjusted pH=5 with 1M hydrochloric acid, and then extracted with diethyl ether (20 mL×5). The combined organic phases were dried over anhydrous sodium sulfate and concentrated under reduced pressure to give the title compound (0.34 g, yield: 23%).

¹H NMR (400 MHz, CDCl₃) δ 6.14 (d, J=10.4 Hz, 1H), 5.96 (d, J=10.4 Hz, 1H).

Step C:

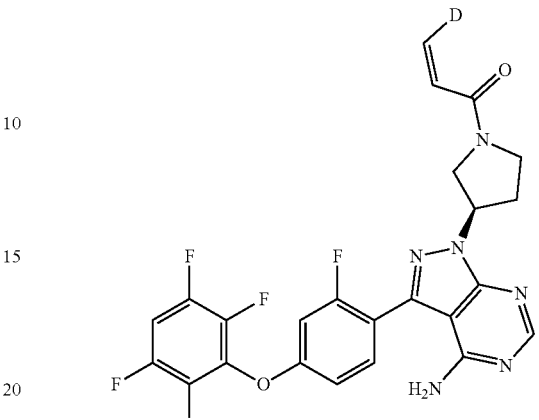

(Z)-1-((R)-3-(4-amino-3-(2-fluoro-4-(3-fluorophe-noxy)phenyl)-1H-pyrazolo[3,4-d]pyrimidin-1-yl)pyrrolidin-1-yl)-3-deuterium-prop-2-en-1-one (Z)-3-deuteriumacrylic acid (151 mg, 2.16 mmol, 1.0 eq.), HATU (1.06 g, 2.80 mmol, 1.3 eq.) and N, N-diisopropyl-ethylamine (838 mg, 6.48 mmol, 3.0 eq.) were added to a solution of 3-(2-fluoro-4-(2,3,5,6-tetrafluorophenoxy)phe-nyl)-1-((R)-pyrrolidin-3-yl)-1H-pyrazolo[3,4-d]pyrimidin-4-amine (1.0 g, 2.16 mmol, 1.0 eq.) in dichloromethane (50 mL). The reaction was stirred at room temperature for 12 hours, and concentrated to give the crude product, which was purified by HPLC-separation (instrument: LC 8A & Gilson 215, fraction collector column: Synergi Max-RP 150*30 mm*4 u, mobile phase A: water (0.5% HCl), mobile phase B: acetonitrile, flow rate: 30 mL/min, gradient B: 36%~37%, 0~17 minutes). After the removal of volatile solvent, the desired fraction was lyophilized to give the title compound hydrochloride (228 mg, yield: 20%).

LC/MS (method: UFLC): RT=2.775 min; m/z=518.1 [M+H]⁺; Total running time=7.000 min.

¹H NMR (400 MHz, CD₃OD) δ 8.45 (s, 1H), 7.70 (t, J=8.4 Hz, 1H), 7.52-7.46 (m, 1H), 7.13-7.05 (m, 2H), 6.71-6.61 (m, 1H), 5.80-5.73 (m, 2H), 4.23-4.20 (m, 1H), 4.09-4.04 (m, 1.5H), 3.93-3.90 (m, 1H), 3.80-3.75 (m, 0.5H), 2.67-2.56 (m, 2H).

Compound 20

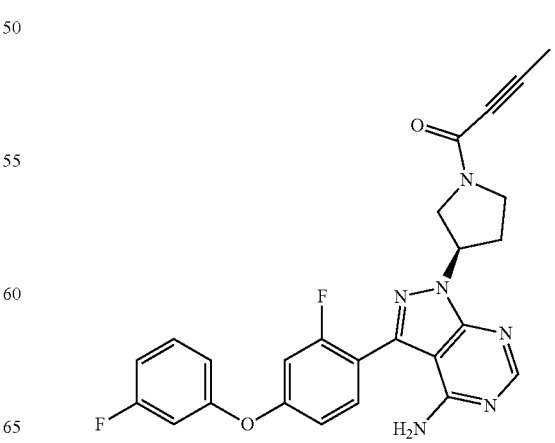

1-((R)-3-(4-amino-3-(2-fluoro-4-(3-fluorophenoxy)phenyl)-1H-pyrazolo[3,4-d]pyrimidin-1-yl)pyrrolidin-1-yl)but-2-yn-1-one A mixture of 3-[2-fluoro-4-(3-fluorophenoxy)phenyl]-1-[(3R)-pyrrolidin-3-yl] pyrazolo[3,4-d]pyrimidin-4-amine (200.00 mg, 489.72 umol, 1.00 eq.), but-2-ynoic acid (41.17 mg, 489.72 umol, 1.00 eq.), HATU (93.10 mg, 244.86 umol, 0.50 eq.) and DIPEA (75.95 mg, 587.66 umol, 102.64 uL, 1.20 eq.) in DCM (5.00 mL) was stirred at 15-18° C. for 2 hrs. TLC showed starting material consumed. The mixture was evaporated to dryness. The residue was purified by prep-HPLC (column: Boston Green ODS 150*30 5 u; mobile phase: acetonitrile/water/0.05% HCl, gradient: 22%-52% (volume ratio), time: 12 min) to give the title compound as hydrochloride salt (82.00 mg, yield: 32.77%).

LC/MS (Method: UFLC): RT=3.057 min; m/z=475.0 [M+H]$^+$; Total running time 7.000 min.

$^1$H NMR (400 MHz, CDCl$_3$) δ 9.92 (s, 1H), 8.34 (d, J=8.8 Hz, 1H), 7.56 (br, 1H), 7.41-7.36 (m, 1H), 7.00-6.86 (m, 5H), 6.58 (br, 1H), 5.62-5.58 (m, 1H), 4.22-3.74 (m, 4H), 2.65-2.50 (m, 2H), 2.02-1.96 (m, 3H).

Example 2—In Vitro Assay

Inhibition Assay of BTK Kinase Activity:

The enzyme reaction mixture of BTK wild type standard HTRF assay contained 1 nM BTK wild type, 1 μM biotin-TK1 peptide, and 30 μM ATP in a buffer. The enzyme reaction were carried out at room temperature for 60 minutes. 5 μl of 0.2 M EDTA were added to quench the reaction and then the inhibitors (5 μl) were added at final concentrations of 2 nM antibody and 62.5 nM XL665. The plates were incubated at room temperature for 60 minutes and then read in the Envision plate reader. The readouts were transformed into inhibition rate % by the equation of (Min Ratio)/(Max-Min)*100%. Hence the IC50 data of test compounds were generated by using four parameters curve fitting.

TABLE 2

Assay data for representative compounds

| Compound No. | BTK IC$_{50}$ (μM) | Compound No. | BTK IC$_{50}$ (μM) | Compound No. | BTK IC$_{50}$ (μM) |
|---|---|---|---|---|---|
| 1 | 0.002 | 2 | 0.023 | 3 | 0.0005 |
| 4 | 0.021 | 5 | 0.001 | | |

Inhibition Assay of Tumor Cell Activity:

Tumor cells (TMD-8, DoHH2 and WSU-DLCL2) were transferred and attached to 96-well plates. After one night, blank buffer and selected concentrations (0.01 nM-100 μM) of the test compound solution were added. After 48 hours incubation, CellTiter-Go was added to lyse the cells. Recording luminescent signal and calculate the percent inhibition of cell viability.

TABLE 3

Inhibition of individual compound on TMD-8 cell line (Inh %)

| Compound | Compound Name (Mechanism) | Inh % | 100 uM | 10 uM | 1 uM | 0.1 uM | 0.01 uM |
|---|---|---|---|---|---|---|---|
| 3 | 3 (BTK) | AVG | 99.69 | 74.93 | 61.66 | 59.59 | 46.07 |
| | | SD | 0.10 | 0.64 | 3.97 | 1.49 | 1.60 |

TABLE 3-continued

Inhibition of individual compound on TMD-8 cell line (Inh %)

| Compound | Compound Name (Mechanism) | Inh % | 100 uM | 10 uM | 1 uM | 0.1 uM | 0.01 uM |
|---|---|---|---|---|---|---|---|
| 3 | 3 (BTK) | AVG | | | 55.05 | 52.40 | 51.66 |
| | | SD | | | 3.47 | 2.17 | 1.21 |
| 6 | 6 (BTK) | AVG | 99.38 | 62.52 | 60.21 | 52.99 | 32.29 |
| | | SD | 0.09 | 1.58 | 3.62 | 3.53 | 5.50 |
| 7 | 7 (BTK) | AVG | 99.32 | 62.89 | 58.57 | 58.68 | 33.85 |
| | | SD | 0.13 | 2.18 | 0.90 | 2.20 | 3.05 |
| 8 | Idelalisib (PI3K) | AVG | 96.79 | 87.69 | 68.92 | 48.83 | 29.44 |
| | | SD | 0.27 | 1.07 | 2.87 | 1.35 | 3.83 |
| 9 | Ibrutinib (BTK) | AVG | 99.93 | 81.41 | 66.11 | 59.14 | 56.16 |
| | | SD | 0.01 | 2.27 | 2.07 | 1.77 | 2.47 |
| 10 | Ruxolitinib (JAK1/2) | AVG | | | 100.78 | −5.53 | 0.05 |
| | | SD | | | 0.05 | 10.51 | 10.00 |
| 11 | Tofactinib (JAK3) | AVG | | | 6.66 | 1.31 | 6.02 |
| | | SD | | | 7.59 | 8.82 | 14.08 |
| 12 | ABT-199 Venetoclax (Bcl-2) | AVG | | | 37.55 | 18.81 | 11.12 |
| | | SD | | | 3.83 | 5.60 | 2.80 |
| 13 | OTS-964 (TOPK) | AVG | | | 101.20 | 49.10 | 8.71 |
| | | SD | | | 0.08 | 4.49 | 10.40 |
| 14 | Everolimus (mTOR) | AVG | | | 68.59 | 67.64 | 65.55 |
| | | SD | | | 1.71 | 2.76 | 2.35 |
| 15 | Pomalidomide (IMID) | AVG | | | 76.84 | 61.69 | 45.12 |
| | | SD | | | 1.03 | 2.34 | 1.26 |
| 16 | Lenalidomide (IMID) | AVG | | | 94.21 | 21.04 | 7.43 |
| | | SD | | | 0.46 | 5.67 | 2.61 |
| 17 | Rapamycin (mTOR) | AVG | | | 64.99 | 59.83 | 58.71 |
| | | SD | | | 2.77 | 1.45 | 2.37 |
| 18 | Methotrexate (antifolate) | AVG | | | 39.55 | 32.04 | −8.45 |
| | | SD | | | 0.71 | 3.05 | 6.02 |
| 19 | Ceritinib (ALK) | AVG | | | | | |
| | | SD | | | | | |

Note:
AVG: Average;
SD: Standard Deviation

Table 4 below demonstrates that double combination has significant inhibition of tumor cell viability. The combination of Compounds 8 and 13; the combination of Compounds 14 and 13; the combination of Compounds 15 and 13; and the combination of Compounds 3 and 13 have shown the highest inhibitory activity against TMD-8 cells.

TABLE 4

Inhibition of "two in one" composition on TMD-8 cell line (Inh %)

| Comp.@Conc. | Inh % | 3 @1 uM | 3 @0.1 uM | 3 @0.01 uM |
|---|---|---|---|---|
| 14 @0.1 uM | AVG | 65.94 | 67.20 | 66.17 |
| | SD | 1.41 | 0.73 | 1.64 |
| 15 @0.1 uM | AVG | 53.25 | 49.26 | 30.27 |
| | SD | 3.19 | 0.67 | 2.67 |
| 8 @0.1 uM | AVG | 68.05 | 64.71 | 63.56 |
| | SD | 2.04 | 2.50 | 5.10 |
| 13 @0.1 uM | AVG | 82.60 | 68.80 | 77.27 |
| | SD | 3.50 | 2.64 | 1.91 |
| 17 @0.1 uM | AVG | 75.73 | 80.41 | 75.12 |
| | SD | 0.53 | 1.29 | 6.22 |
| 12 @0.1 uM | AVG | 85.97 | 79.99 | 65.36 |
| | SD | 1.50 | 1.54 | 0.83 |
| 18 @0.1 uM | AVG | 59.93 | 46.58 | 35.68 |
| | SD | 2.77 | 6.76 | 5.94 |
| Comp.@Conc. | Inh % | 8 @1 uM | 8 @0.1 uM | 8 @0.01 uM |
| 14 @0.1 uM | AVG | 81.20 | 67.95 | 58.69 |
| | SD | 0.33 | 1.59 | 1.08 |

TABLE 4-continued

Inhibition of "two in one" composition on TMD-8 cell line (Inh %)

| | | | | |
|---|---|---|---|---|
| 15 @0.1 uM | AVG | 76.96 | 42.58 | 24.14 |
| | SD | 0.95 | 7.50 | 3.94 |
| 13 @0.1 uM | AVG | 95.76 | 83.60 | 75.38 |
| | SD | 0.31 | 0.53 | 3.51 |
| 3 @0.1 uM | AVG | 86.26 | 80.21 | 73.01 |
| | SD | 2.25 | 2.87 | 2.46 |

| Comp.@Conc. | Inh % | 13 @1 uM | 13 @0.1 uM | 13 @0.01 uM |
|---|---|---|---|---|
| 8 @0.1 uM | AVG | 99.31 | 47.73 | 48.71 |
| | SD | 0.06 | 2.52 | 4.50 |
| 14 @0.1 uM | AVG | 99.46 | 59.47 | 60.30 |
| | SD | 0.11 | 0.73 | 1.44 |
| 15 @0.1 uM | AVG | 99.09 | 8.82 | 12.97 |
| | SD | 0.17 | 3.93 | 4.84 |
| 3 @0.1 uM | AVG | 99.16 | 97.60 | 52.43 |
| | SD | 0.42 | 0.19 | 1.07 |

| Comp.@Conc. | Inh % | 15 @1 uM | 15 @0.1 uM | 15 @0.01 uM |
|---|---|---|---|---|
| 8 @0.1 uM | AVG | 80.19 | 43.34 | 42.81 |
| | SD | 1.25 | 5.76 | 3.81 |
| 14 @0.1 uM | AVG | 61.84 | 57.04 | 58.46 |
| | SD | 1.62 | 1.70 | 0.32 |
| 13 @0.1 uM | AVG | 71.75 | 30.72 | 1.36 |
| | SD | 0.35 | 7.16 | 5.17 |
| 3 @0.1 uM | AVG | 96.92 | 70.04 | 49.93 |
| | SD | 0.19 | 4.46 | 5.42 |

| Comp.@Conc. | Inh % | 18 @1 uM | 18 @0.1 uM | 18 @0.01 uM |
|---|---|---|---|---|
| 14 @0.1 uM | AVG | 54.43 | 52.67 | 56.87 |
| | SD | 0.70 | 2.71 | 2.27 |
| 3 @0.1 uM | AVG | 46.90 | 42.73 | 34.99 |
| | SD | 2.34 | 2.91 | 1.26 |

| Comp.@Conc. | Inh % | 9 @1 uM | 9 @0.1 uM | 9 @0.01 uM |
|---|---|---|---|---|
| 14 @0.1 uM | AVG | 71.04 | 58.89 | 56.54 |
| | SD | 2.52 | 9.71 | 13.33 |
| 19 @0.1 uM | AVG | 52.60 | 43.68 | 33.70 |
| | SD | 3.67 | 4.16 | 1.51 |
| 18 @0.1 uM | AVG | 55.19 | 42.42 | 32.13 |
| | SD | 2.63 | 3.32 | 3.08 |

Table 5 below demonstrates that triple combination has significant inhibition of tumor cell viability. The combination of Compounds 3, 14 and 12; and the combination of Compound 3, 8 and 12 have shown the highest inhibitory activity up to 95% even at the concentration as low as 10 nM for Compound 3.

TABLE 5

Inhibition of "three in one" composition on TMD-8 cell line (Inh %)

| Comp.@Conc. | Inh % | 3 @1 uM | 3 @0.1 uM | 3 @0.01 uM |
|---|---|---|---|---|
| 14 @0.1 uM + | AVG | 76.42 | 80.77 | 83.22 |
| 15 @0.1 uM | SD | 4.50 | 1.38 | 0.37 |
| 17 @0.1 uM + | AVG | 89.89 | 85.62 | 88.57 |
| 15 @0.1 uM | SD | 0.72 | 7.68 | 3.37 |
| 14 @0.1 uM + | AVG | 93.44 | 94.73 | 94.65 |
| 12 @0.1 uM | SD | 0.55 | 0.92 | 1.11 |
| 8 @0.1 uM + | AVG | 95.56 | 95.30 | 94.62 |
| 12 @0.1 uM | SD | 0.40 | 0.10 | 0.06 |
| 18 @0.1 uM + | AVG | 66.44 | 71.70 | 58.27 |
| 14 @0.1 uM | SD | 8.75 | 1.91 | 2.80 |

| Comp.@Conc. | Inh % | 15 @1 uM | 15 @0.1 uM | 15 @0.01 uM |
|---|---|---|---|---|
| 14 @0.1 uM + | AVG | 92.74 | 82.66 | 75.17 |
| 3 @0.1 uM | SD | 0.38 | 1.90 | 2.48 |

TABLE 5-continued

Inhibition of "three in one" composition on TMD-8 cell line (Inh %)

| Comp.@Conc. | Inh % | 8 @1 uM | 8 @0.1 uM | 8 @0.01 uM |
|---|---|---|---|---|
| 14 @0.1 uM + | AVG | 87.17 | 79.06 | 59.45 |
| 15 @0.1 uM | SD | 1.70 | 0.73 | 2.16 |

| Comp.@Conc. | Inh % | 13 @1 uM | 13 @0.1 uM | 13 @0.01 uM |
|---|---|---|---|---|
| 15 @0.1 uM + | AVG | 98.97 | 22.27 | −19.34 |
| 3 @0.1 uM | SD | 0.28 | 34.18 | 11.80 |
| 15 @0.1 uM + | AVG | 99.30 | 29.58 | −3.32 |
| 8 @0.1 uM | SD | 0.15 | 27.38 | 11.27 |
| 15 @0.1 uM + | AVG | 99.33 | 19.51 | −1.30 |
| 14 @0.1 uM | SD | 0.11 | 48.40 | 6.76 |

| Comp.@Conc. | Inh % | 10 @1 uM | 10 @0.1 uM | 10 @0.01 uM |
|---|---|---|---|---|
| 15 @0.1 uM + | AVG | 24.40 | −6.35 | −0.77 |
| 3 @0.1 uM | SD | 5.84 | 5.66 | 18.61 |
| 15 @0.1 uM + | AVG | 16.26 | 2.31 | −6.21 |
| 8 @0.1 uM | SD | 2.14 | 1.28 | 4.86 |
| 15 @0.1 uM Plus | AVG | −0.86 | 0.98 | −2.40 |
| 14 @0.1 uM | SD | 6.50 | 5.87 | 1.06 |

| Comp.@Conc. | Inh % | 9 @1 uM | 9 @0.1 uM | 9 @0.01 uM |
|---|---|---|---|---|
| 18 @0.1 uM + | AVG | 72.55 | 66.59 | 64.76 |
| 14 @0.1 uM | SD | 0.22 | 11.12 | 8.34 |
| 15 @0.1 uM Plus | AVG | 82.81 | 86.91 | 78.60 |
| 14 @0.1 uM | SD | 1.05 | 1.41 | 13.08 |

Table 6 below demonstrates that the triple combination of Compound 3, 14 and 15 is effective against multi-drug resistant WSU-DLCL2 tumor cells, superior to each single agent alone.

TABLE 6

Inhibition of individual compound and "three in one" composition on resistant WSU-DLCL2 cell line (Inh %)

| Comp.@Conc. | Inh % | 1 uM | 0.1 uM | 0.01 uM |
|---|---|---|---|---|
| 3 | AVG | 41.04 | −1.36 | −10.06 |
| | SD | 7.73 | 2.59 | 11.14 |
| 15 | AVG | 46.61 | −8.32 | −14.53 |
| | SD | 1.15 | 4.49 | 13.72 |
| 14 | AVG | 55.35 | 46.71 | 40.81 |
| | SD | 1.67 | 0.53 | 2.67 |

| Comp.@Conc. | Inh % | 3 | 3 | 3 |
|---|---|---|---|---|
| 15 @0.1 uM + | AVG | 83.76 | 63.69 | 56.67 |
| 14 @0.1 uM | SD | 1.33 | 4.19 | 4.36 |

Table 7 below demonstrates that the triple combination of Compounds 3, 14 and 15 is effective against more difficult to treat DoHH-2 tumor cells, superior to each of the single agents alone.

TABLE 7

Inhibition of individual compound and "three in one" composition on DoHH-2 cell line (Inh %)

| Comp.@Conc. | Inh % | 1 uM | 0.1 uM | 0.01 uM |
|---|---|---|---|---|
| 3 | AVG | 49.93 | 34.83 | 15.58 |
| | SD | 2.72 | 0.70 | 5.54 |
| 15 | AVG | 51.32 | 6.75 | −7.95 |
| | SD | 3.86 | 8.77 | 1.57 |
| 14 | AVG | 60.33 | 59.17 | 51.80 |
| | SD | 3.52 | 1.68 | 3.35 |

TABLE 7-continued

Inhibition of individual compound and "three in one" composition on DoHH-2 cell line (Inh %)

| Comp.@Conc. | Inh % | 3 | 3 | 3 |
|---|---|---|---|---|
| 15 @0.1 uM + 14 @0.1 uM | AVG | 78.75 | 81.87 | 71.87 |
| | SD | 0.45 | 1.02 | 6.47 |

Table 8 demonstrates that the triple combination of Compound 3, 14 and 15 at various doses of each single agent are all effective against the sensitive TMD-8 tumor cells.

TABLE 8

Inhibition of compositions with different proportions on TMD-8 cell line (Inh %)

| Molar ratio Comp.@Conc. | Inh % | 1.0 uM | 0.1 uM | 0.01 uM |
|---|---|---|---|---|
| 3 + 14 | AVG | 72.97 | 71.71 | 66.64 |
| (19:1 molar ratio) | SD | 0.93 | 1.49 | 0.83 |
| 3 + 14 + 15 | AVG | 97.08 | 89.29 | 67.75 |
| (19:1:37 molar ratio) | SD | 0.52 | 1.30 | 1.12 |
| 3 + 14 + 15 | AVG | 97.16 | 91.23 | 80.09 |
| (1:1:1 molar ratio) | SD | 0.17 | 0.85 | 0.96 |
| 3 + 14 + 15 | AVG | 78.21 | 72.73 | 63.34 |
| (50:1:1 molar ratio) | SD | 2.26 | 1.21 | 0.97 |
| 3 + 14 + 15 | AVG | 88.09 | 77.18 | 68.76 |
| (10:1:1 molar ratio) | SD | 0.70 | 1.66 | 2.12 |
| | | 3 @1 uM | 3 @0.1 uM | 3 @0.01 uM |
| 14 @0.1 uM + 15 @0.1 uM | AVG | 85.33 | 88.83 | 87.78 |
| | SD | 0.78 | 0.71 | 2.36 |

Example 3—In Vivo Assay

Pharmacokinetic Study in Male SD Rats:

Male SD rats for pharmacokinetic study within 24 hours were divided into two groups: intravenous administration and oral administration. Each group has three animals. For group of intravenous administration, blood samples were collected at pre-dose, 0.0833, 0.167, 0.5, 1, 2, 4, 8, 24 h post-dose; for group of oral administration, blood samples were collected at pre-dose, 0.167, 0.5, 1, 2, 4, 8, 24 h post-dose. After blood collection, HPLC-MS/MS was applied to determine plasma concentrations of the compound. The calculated pharmacokinetic parameters of intravenous group include mean plasma clearance (CLp), mean apparent volume of distribution at stead state (Vdss), 0-24 h area under the curve (AUC), 0-24 h mean residence time (MRT), the half-life (T1/2); The calculated pharmacokinetic parameters of oral group include mean peak concentration (Cmax), 0-24 h area under the curve (AUC), 0-24 h mean residence time (MRT); mean relative bioavailability for the study.

Pharmacokinetic Study in Beagle Dogs:

Beagle dogs for pharmacokinetic study within 24 hours were divided into two groups: intravenous administration (1 mg per kilogram) and oral administration (3 mg per kilogram). Each group has three animals. For group of intravenous administration, blood samples were collected at pre-dose, 0.033, 0.083, 0.25, 0.5, 1, 3, 6, 9, 24 h post-dose; for group of oral administration, blood samples were collected at pre-dose, 0.083, 0.25, 0.5, 1, 3, 6, 9, 24 h post-dose. After blood collection, HPLC-MS/MS was applied to determine plasma concentrations of the compound. The calculated pharmacokinetic parameters of intravenous group include mean plasma clearance (CLp), mean apparent volume of distribution at stead state (Vdss), 0-24 h area under the curve (AUC), 0-24 h mean residence time (MRT), the half-life (T1/2); The calculated pharmacokinetic parameters of oral group include mean peak concentration (Cmax), 0-24 h area under the curve (AUC), 0-24 h mean residence time (MRT); mean relative bioavailability for the study.

TABLE 9

PK Parameters for Compound 3 in rats

| | Group | | | |
|---|---|---|---|---|
| | 1 | | 2 | |
| | Dose Route | | | |
| | IV | | PO | |
| | Dose level | | | |
| | 2 mg/kg | | 10 mg/kg | |
| | Mean | SD | Mean | SD |
| $C_0$ or $C_{max}$ (ng/mL) | 1390 | 247 | 641 | 191 |
| $T_{max}$ (hr) | — | — | 1.33 | 0.753 |
| $T_{1/2}$ (hr) | 0.787 | 0.0895 | 1.71 | 0.489 |
| Vdss (L/kg) | 1.61 | 0.339 | — | — |
| CL (mL/min/kg) | 20.2 | 5.60 | — | — |
| $AUC_{0\text{-}last}$ (hr · ng/mL) | 1740 | 421 | 3230 | 1120 |
| $AUC_{0\text{-}inf}$ (hr · ng/mL) | 1740 | 420 | 3260 | 1140 |
| Bioavailability (%)$^a$ | — | — | 37.1 | — |

TABLE 10

PK Parameters for Compound 3 in dogs

| | Group | | | |
|---|---|---|---|---|
| | 1 | | 2 | |
| | Dose Route | | | |
| | IV | | PO | |
| | Dose level | | | |
| | 2 mg/kg | | 5 mg/kg | |
| | Mean | SD | Mean | SD |
| $C_0$ or $C_{max}$ (ng/mL) | 663 | 79.5 | 189 | 53.3 |
| $T_{max}$ (hr) | — | — | 1.17 | 0.408 |
| $T_{1/2}$ (hr) | 2.27 | 0.873 | 2.92 | 1.22 |
| Vdss (L/kg) | 4.24 | 0.370 | — | — |
| CL (mL/min/kg) | 34.6 | 5.58 | — | — |
| $AUC_{0\text{-}last}$ (hr · ng/mL) | 977 | 181 | 650 | 247 |
| $AUC_{0\text{-}inf}$ (hr · ng/mL) | 987 | 183 | 574 | 123 |
| Bioavailability (%)$^a$ | — | — | 26.2 | — |

Table 11 below shows that the AUC of Compound 3 in rats is significantly higher than that of ibrutinib (U.S. FDA's NDA Application No. 205552Origls000_pharmacological review(s)).

TABLE 11

TK data for Compound 3 in rats

| Dose (mg/kg) | Study Day | Sex | Cmax (ng/mL) | Tmax (h) | $AUC_{0\text{-}24\,h}$ (h*ng/mL) |
|---|---|---|---|---|---|
| 40 | 1 | Male | 2160 | 2.0 | 13700 |
| | | Female | 2660 | 1.0 | 17300 |
| | 28 | Male | 2090 | 2.0 | 15400 |
| | | Female | 2970 | 1.0 | 17300 |

TABLE 11-continued

TK data for Compound 3 in rats

| Dose (mg/kg) | Study Day | Sex | Cmax (ng/mL) | Tmax (h) | AUC$_{0-24\,h}$ (h*ng/mL) |
|---|---|---|---|---|---|
| 100 | 1 | Male | 2740 | 2.0 | 21700 |
|  |  | Female | 3700 | 4.0 | 28900 |
|  | 28 | Male | 3990 | 2.0 | 30300 |
|  |  | Female | 3830 | 1.0 | 29600 |
| 200 | 1 | Male | 4220 | 2.0 | 37600 |
|  |  | Female | 4680 | 4.0 | 65200 |
|  | 28 | Male | 4540 | 2.0 | 45100 |
|  |  | Female | 5490 | 8.0 | 60200 |

Table 12 below shows that the AUC of Compound 3 in dogs is significantly higher than that of ibrutinib (U.S. FDA's NDA Application No. 205552Origls000_pharmacological review(s)).

TABLE 12

TK data for Compound 3 in dogs

| Dose (mg/kg/day) | Study Day | Sex | Cmax (ng/mL) | Tmax (h) | AUC$_{0-24\,h}$ (h*ng/mL) |
|---|---|---|---|---|---|
| 15 | 1 | Male | 746 ± 18.1 | 2.0 (1.0-2.0) | 3550 ± 562 |
|  |  | Female | 685 ± 212 | 1.0 (1.0-2.0) | 2930 ± 980 |
|  | 28 | Male | 576 ± 145 | 2.0 (2.0-2.0) | 3260 ± 732 |
|  |  | Female | 687 ± 123 | 2.0 (1.0-2.0) | 3730 ± 549 |
| 45 | 1 | Male | 1240 ± 381 | 2.0 (1.0-2.0) | 6480 ± 1670 |
|  |  | Female | 1220 ± 431 | 2.0 (2.0-2.0) | 6220 ± 3000 |
|  | 28 | Male | 1470 ± 538 | 2.0 (2.0-4.0) | 9170 ± 3810 |
|  |  | Female | 1060 ± 263 | 2.0 (2.0-4.0) | 8130 ± 1490 |
| 105 | 28 | Male | 2700 ± 769 | 2.0 (2.0-2.0) | 16400 ± 5410 |
|  |  | Female | 2420 ± 670 | 2.0 (2.0-4.0) | 17300 ± 2830 |
| 150 | 1 | Male | 2460 ± 858 | 4.0 (1.0-8.0) | 22900 ± 13900 |
|  |  | Female | 1850 ± 605 | 2.0 (1.0-4.0) | 11200 ± 5990 |

Inhibition Study of Tumor Growth In Vivo:

SCID mice or nude mice (weighing about 18 g at the beginning of the experiment) were randomly divided into groups by the software in order to achieve close average weights between groups and control the bias within the allowable range. The mice were injected BTK cell lines (TMD-8, WSU-DLCL2 and DoHH-2) for tumor formation. Inhibitors were administered orally once or twice a day, a total of 14 days, 21 days or 28 days. Body weights and tumor volume were recorded.

Xenograft Tumor Models Inoculated with TMD-8, or DoHH2, or WSU-DLCL2 Tumor Cell Lines:

TMD-8 is a sensitive human diffuse large B-cell lymphoma cell line, and DoHH2 is a more difficult to treat human follicular lymphoma cell line, while WSU-DLCL2 is a multi-drug resistant (MDR) human non-Hodgkin's lymphoma cell line. Drug combination therapies provide better efficacies in all three tumor models than single targeted agent alone.

Compounds (Compounds 3, 9, 14 and others as shown in the charts) and its combinations were evaluated against tumor growth in xenograft models in female CB-17 SCID mice. The TMD-8, DoHH2, WSU-DLCL2 tumor cells were maintained in vitro as a suspension culture in RPMI-1640 medium supplemented with 10% heat inactivated fetal calf serum at 37° C. in an atmosphere of 5% $CO_2$ in air. The tumor cells were routinely subcultured twice weekly. The cells growing in an exponential growth phase were harvested and counted for tumor inoculation. Each mouse was inoculated subcutaneously at the right flank with the tumor cells ($10 \times 10^6$) in 0.2 ml of PBS with Matrigel (1:1) for tumor development. The treatments were started after the average tumor size reached approximately 100-200 mm$^3$. Each group consisted of 6-10 tumor-bearing mice. The testing article (vehicle, compound or combination) was orally administrated to the mice according to the predetermined doses for 14-days or 21-days. Animal body weight and tumor volume were measured every 2- or 3-days throughout the treatment.

Adjuvant-Induced Arthritis AA Model:

The combination of Compounds 3 and 14 was evaluated in adjuvant-induced arthritis (AA) model in female Lewis rats. All rats except the normal group were immunized with complete Freund's adjuvant (CFA) subcutaneously at the left hind paw to induce arthritis at day 0. At 6 days post immunization, some rats started to display clinical symptoms of arthritis, e.g., erythema and swelling. At day 13, the immunized animals were re-grouped to 7 groups, including vehicle, Compound 3 (5 mg/kg)/Compound 14 (0.5 mg/kg) BID treatment, Compound 3 (15 mg/kg)/Compound 14 (1.5 mg/kg) BID treatment, Compound 3 (30 mg/kg)/Compound 14 (3 mg/kg) QD treatment, Compound 3 (5 mg/kg) BID treatment, Compound 14 (0.5 mg/kg) BID treatment, and a positive control (Compound 11, 3 mg/kg, BID treatment) groups, based on body weight and clinical scores. The treatments were given orally for 3 consecutive weeks. The body weight, paw volume and clinical score were monitored every other day after day 13 throughout the course of the study. At the terminal point, right hind paws were collected for histopathology analysis with H.E. staining.

Collagen-Induced Arthritis (CIA) Model:

The combination of Compounds 3 and 12 was evaluated in collagen induced arthritis (CIA) mouse model in Male DBA/1 mice. The animals were divided into 8 groups, including a normal, a vehicle, five treatment groups: All animals (except the normal group) were immunized with 200 μg of bovine collagen (type II) on day 0 and day 21. Seven days (day 28) after boosting immunization, animals started to show symptoms of disease with an average clinical score around 1. On the same day, immunized mice were randomly divided into 7 groups: Compound 3 (1.5 mg/kg) and Compound 14 (0.15 mg/kg) combination treatment BID group, Compound 3 (4.5 mg/kg) and Compound 14 (0.45 mg/kg) combination treatment BID group, Compound 3 (1.5 mg/kg) and Compound 14 (0.15 mg/kg) combination treatment QD group, Compound 3 (1.5 mg/kg) single treatment QD group, Compound 14 (0.15 mg/kg) single treatment QD group, and a positive control group (0.2 mg/kg of dexamethasone), and start to dosing and treatment. The treatments were given orally for 2 consecutive weeks. Body weight and clinical score were monitored through the study (recorded three times a week started after second immunization). At the end of the study, animals were euthanized and both hind paws were collected for histopathology analysis.

Figure 2:
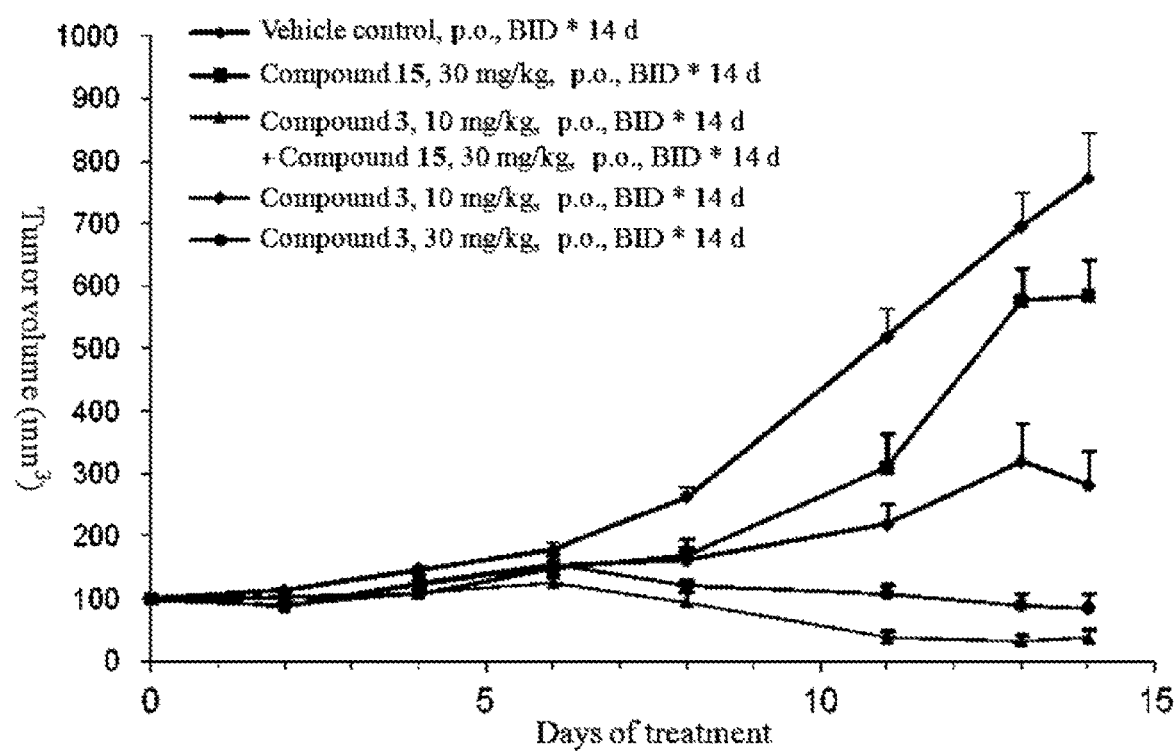
FIG. 2 is a graph showing the antitumor effect of Compound 3, Compound 15, and their combination in the TMD-8 lymphoma xenograft SCID mouse model.
Figure 3:
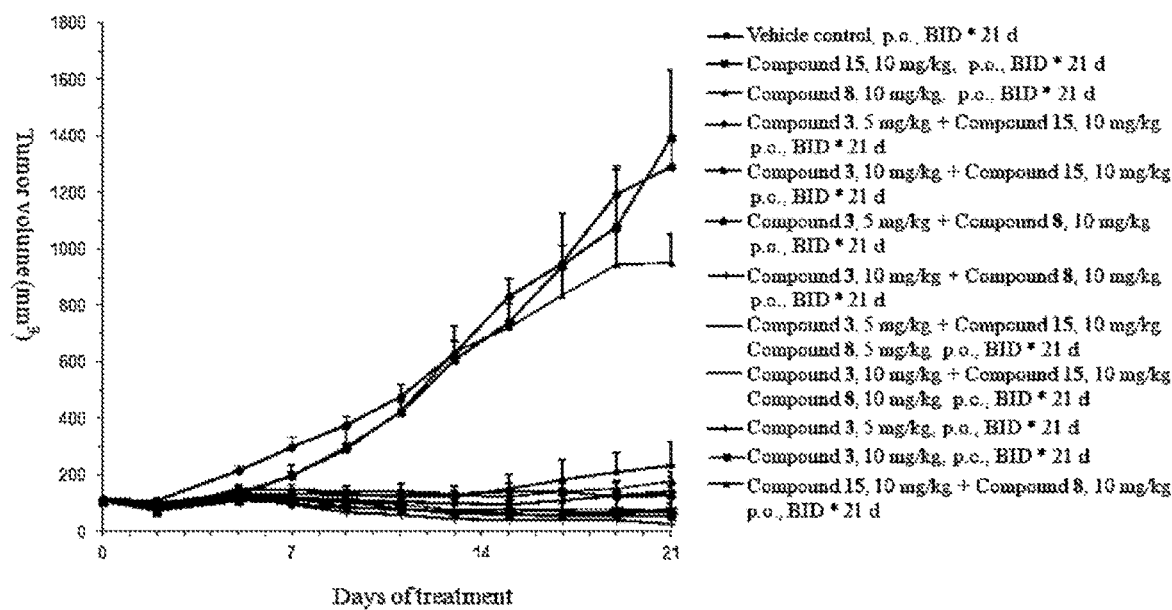
FIG. 3 is a graph showing the antitumor effect of Compounds 3, 8, and 15, and their combinations in the TMD-8 lymphoma xenograft SCID mouse model.
Figure 4:
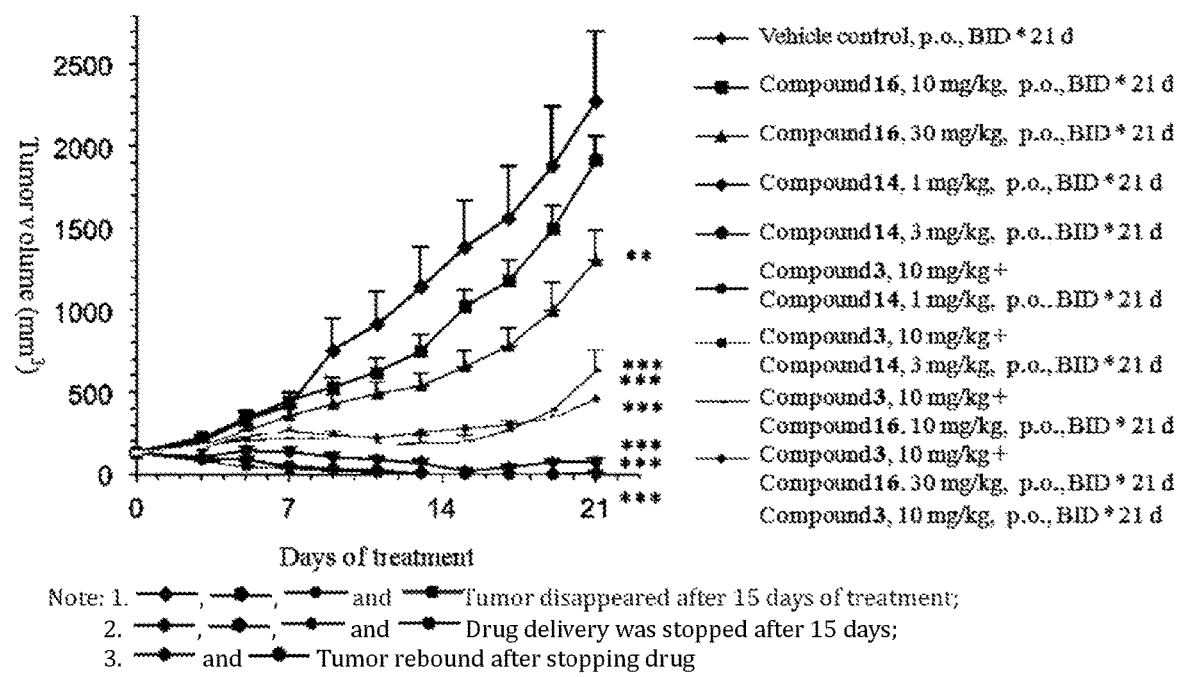
FIG. 4 is a graph showing the antitumor effect of Compounds 3, 14, and 16, and their combinations in the TMD-8 lymphoma xenograft SCID mouse model.

As shown in FIG. 4, although the administration of an mTOR kinase inhibitor (e.g., Compound 14) led to tumor disappearance in TMD-8 diffuse large B-cell lymphoma (DLBCL) mice model after 15 days of treatment, the tumor rebounded after treatment was stopped after day 15. Surprisingly, no tumor rebound was observed when the mTOR kinase inhibitor was administered in combination with a BTK inhibitor (e.g., Compound 3). In comparison, as shown in FIGS. 2-4, the DLBCL tumor did not disappear when the combination of the BTK inhibitor and an IMiD (e.g., Compounds 15 and 16) was administered, when the combination of the BTK inhibitor and a PI3K kinase inhibitor (e.g., Compound 8) was administered, when the combination of the IMiD and the PI3K kinase inhibitor was administered, or when the combination of the BTK inhibitor, the IMiD and the PI3K kinase inhibitor was administered.

Figure 5:
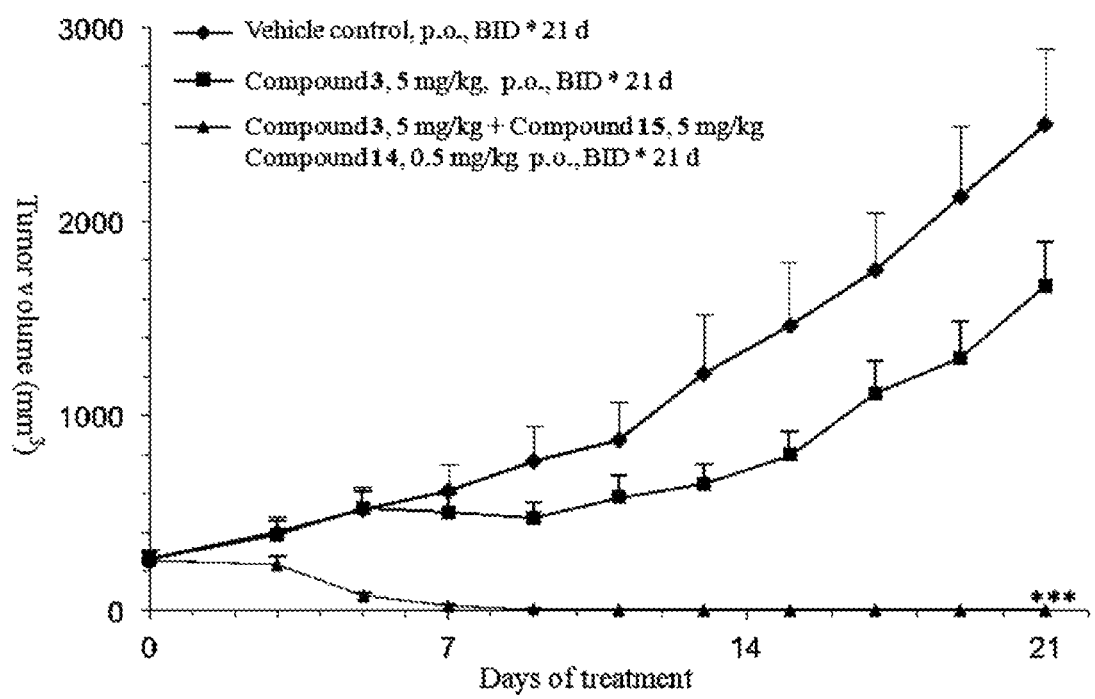
FIG. 5 is a graph showing the antitumor effect of Compounds 3, 14, and 15, and their combination in the TMD-8 lymphoma xenograft SCID mouse model.

As shown in FIG. 5, the triple combination of a BTK inhibitor (e.g., Compound 3), an mTOR kinase inhibitor (e.g., Compound 14), and an IMiD (e.g., Compound 15) led to tumor disappearance in TMD-8 mice model after 9 days of treatment and, unexpectedly, the tumor did not rebound after treatment was stopped after day 12 and completed regression was observed throughout the rest of the 21-day period.

As shown in FIG. 12, the triple combination of a BTK inhibitor (e.g., Compound 3), an mTOR kinase inhibitor (e.g., Compound 14), and a Bcl-2 inhibitor (e.g., Compound 12) led to tumor disappearance in TMD-8 mice model after 8 days of treatment and, unexpectedly, the tumor did not rebound after treatment was stopped and completed regression was observed throughout the rest of the 14-day period. In comparison, the DLBCL tumor did not disappear when only the mTOR kinase inhibitor and the Bcl-2 inhibitor were administered in combination, when only the BTK inhibitor and the Bcl-2 inhibitor were administered in combination, or when the BTK inhibitor and the Bcl-2 inhibitor were administered in combination with a PI3K kinase inhibitor (e.g., Compound 8).

Figure 6:
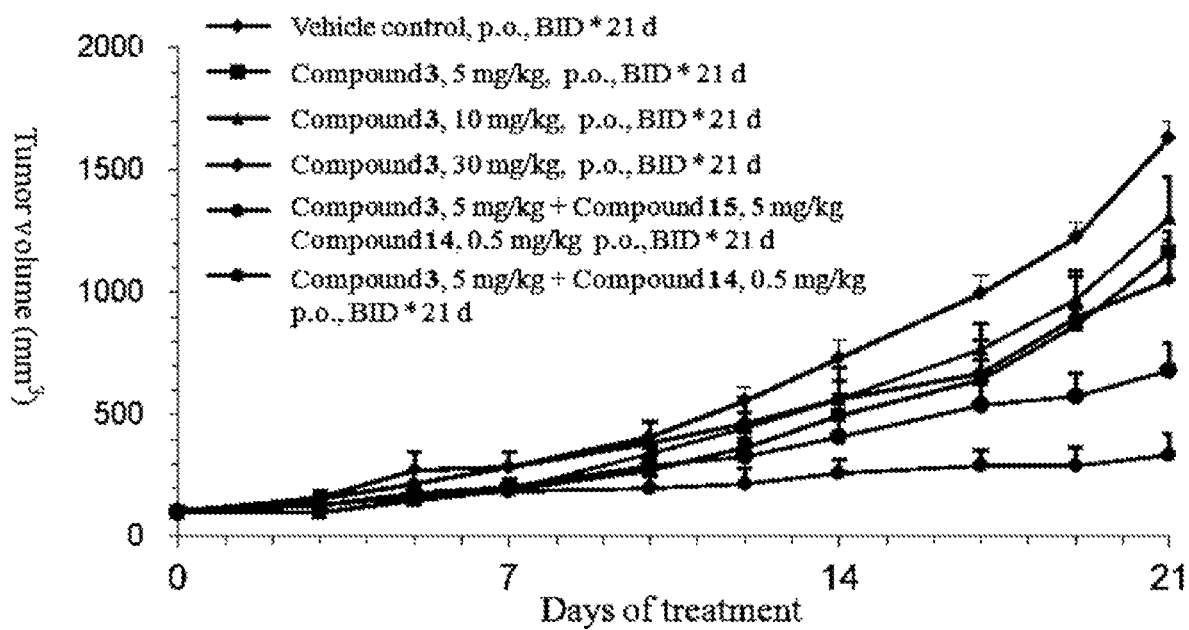
FIG. 6 is a graph showing the antitumor effect of Compounds 3, 14, and 15, and their combinations in a DoHH-2 lymphoma xenograft SCID mouse model.
Figure 7:
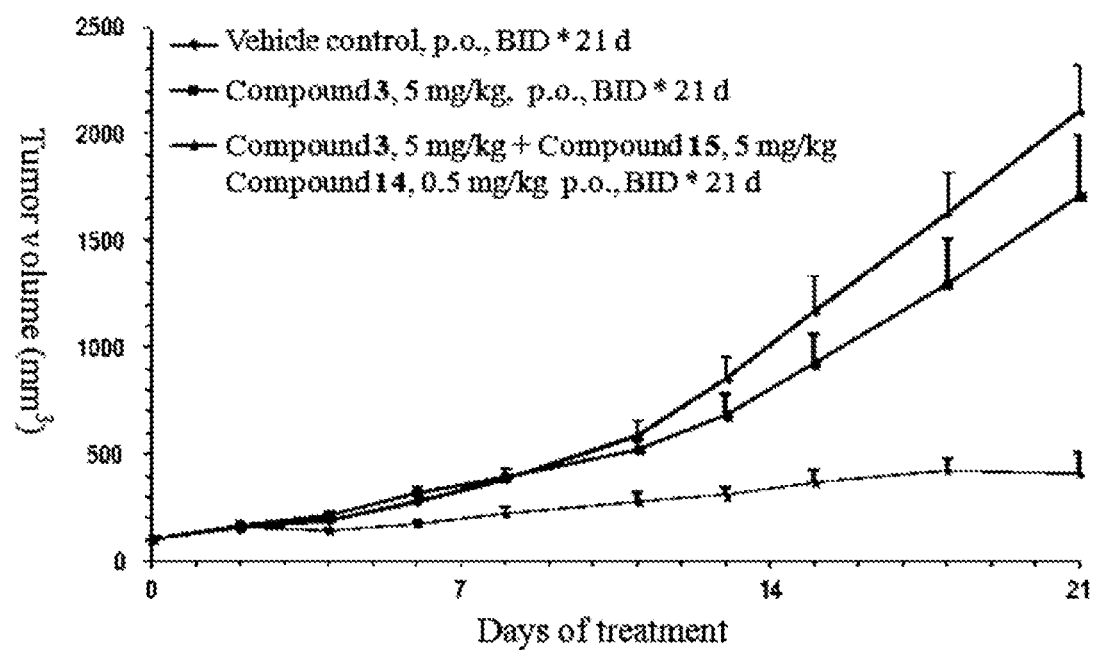
FIG. 7 is a graph showing the antitumor effect of Compound 3, 14, and 15, and their combination in the DoHH-2 lymphoma xenograft SCID mouse model.

As shown in FIGS. 6 and 7, the administration of a BTK inhibitor (e.g., Compound 3) and an mTOR kinase inhibitor (e.g., Compound 14) performed better than the administration of the BTK inhibitor alone in terms of controlling tumor growth in DoHH2 follicular lymphoma (FL) mice model. Surprisingly, when the BTK inhibitor and the mTOR kinase inhibitor were administered in combination with an IMiD (e.g., Compound 15), tumor growth in DoHH2 mice model was reduced to a minimal level. Such synergistic effects were reproduced in two separate experiments (FIGS. 6 and 7).

Figure 8:
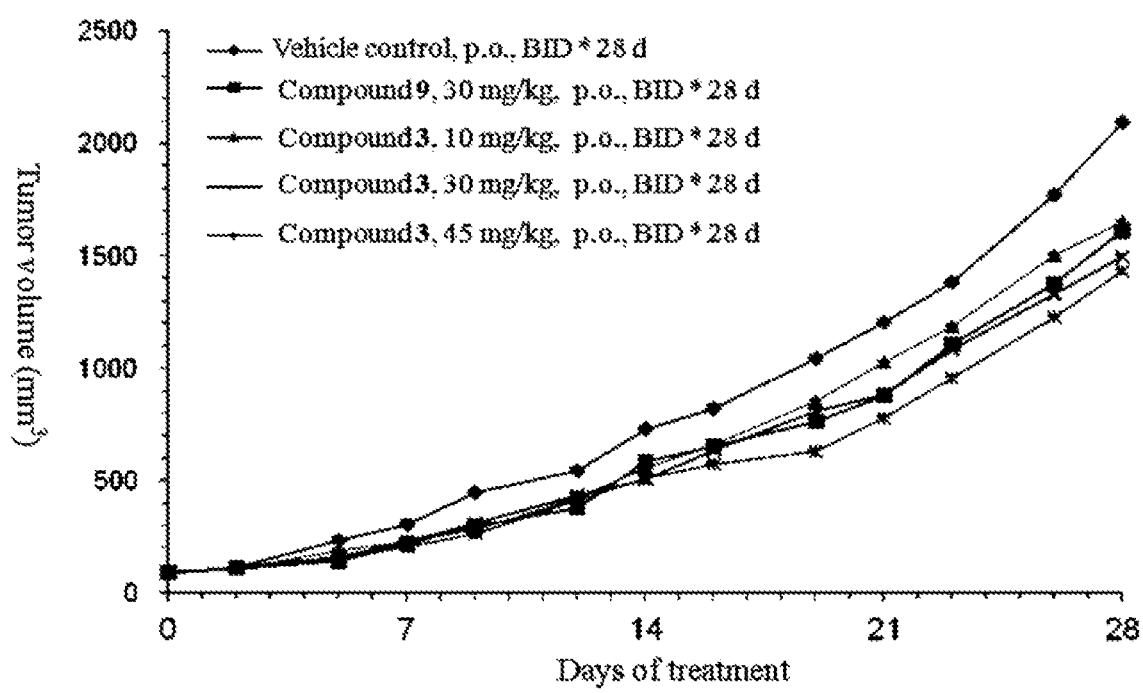
FIG. 8 is a graph showing the antitumor effect of Compounds 3 and 9 in a resistant WSU-DLCL2 SCID mouse model.
Figure 9:
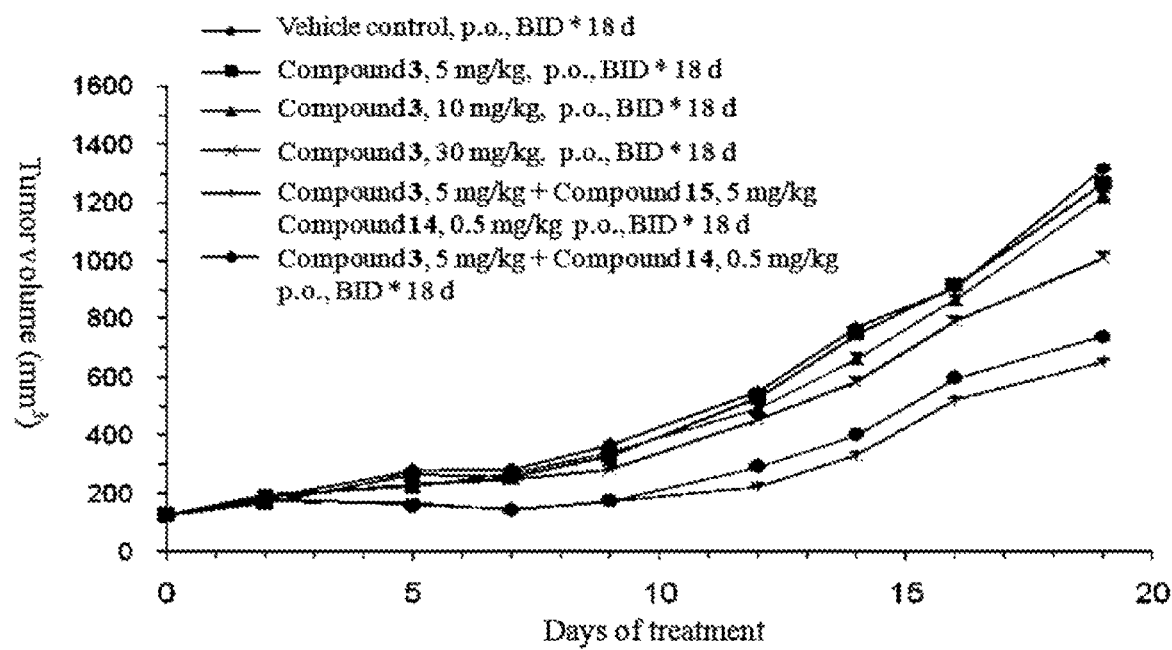
FIG. 9 is a graph showing the antitumor effect of Compounds 3, 14, and 15, and their combination in the resistant WSU-DLCL2 SCID mouse model.

As shown in FIG. 8, the efficacy of Compound 3 in WSU-DLCL2 non-Hodgkin's lymphoma mice model is in line with the efficacy of Ibrutinib, an FDA-approved BTK inhibitor. As shown in FIG. 9, the combination of a BTK inhibitor (e.g., Compound 3), an mTOR kinase inhibitor (e.g., Compound 14), and an IMiD (e.g., Compound 15) at a total of 21 mg/kg/day for all three drugs combined were able to reduce tumor growth in WSU-DLCL2 mice model. In comparison, EZH2 inhibitor EPZ-6438, which is currently undergoing clinical trial, achieved a similar effect against the WSU-DLCL tumor only by gavage to mice at a very high dose of 480 mg/kg/day (see Knutson et al., Mol. Cancer Ther., 2014, 13:842-854, FIG. 4A).

Figure 10:
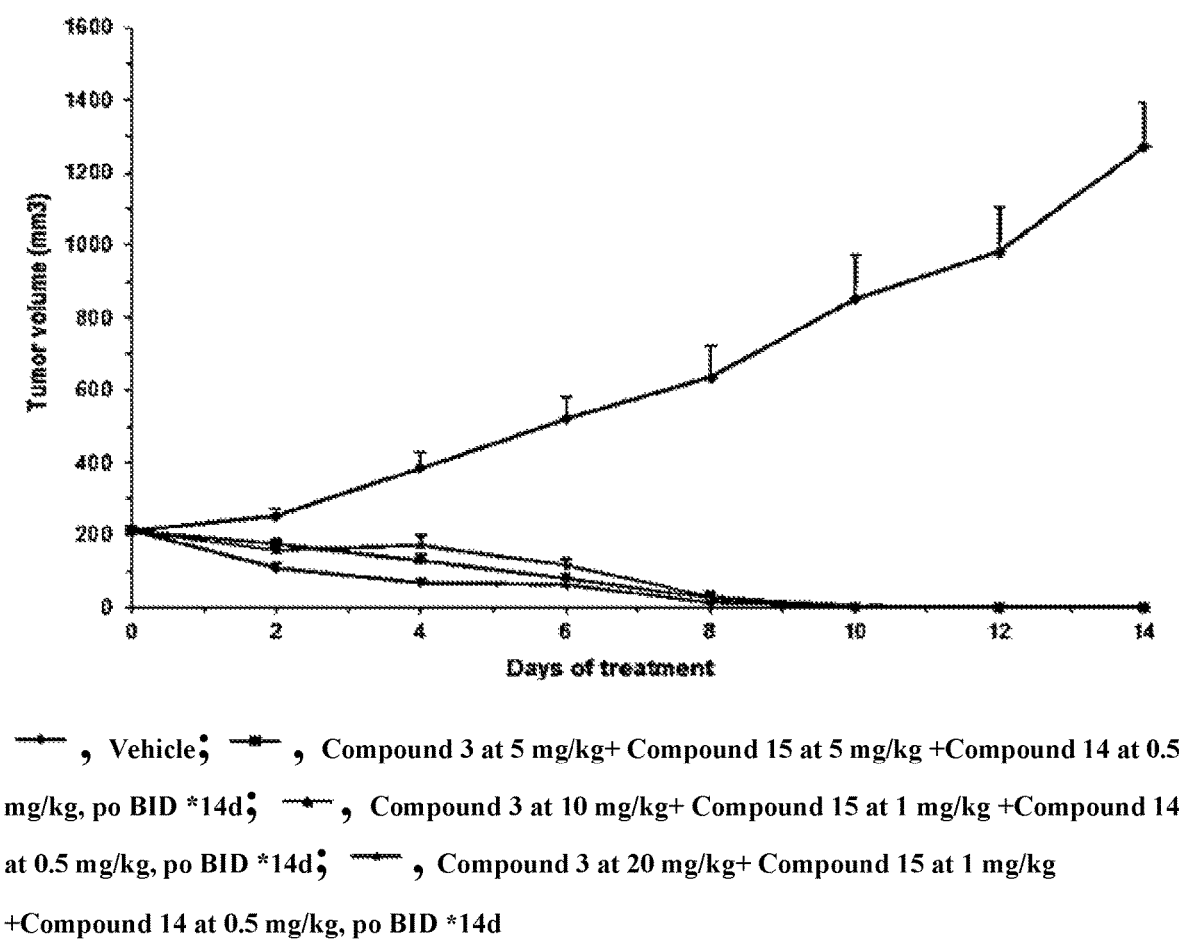
FIG. 10 is a graph showing the antitumor effect of triple combination of Compounds 3, 14, and 15 at different dose combinations in the TMD-8 lymphoma xenograft SCID mouse model.

Moreover, FIG. 10 demonstrates that the efficacy of the triple combination therapy against TMD-8 diffuse large B-cell lymphoma remains substantially consistent at various doses of the individual ingredients. Furthermore, FIG. 11 demonstrates that the efficacy of the triple combination therapy against DoHH2 follicular lymphoma is not limited to Compound 3 but applicable to other BTK inhibitors (e.g., Ibrutinib) as well.

Figure 13:
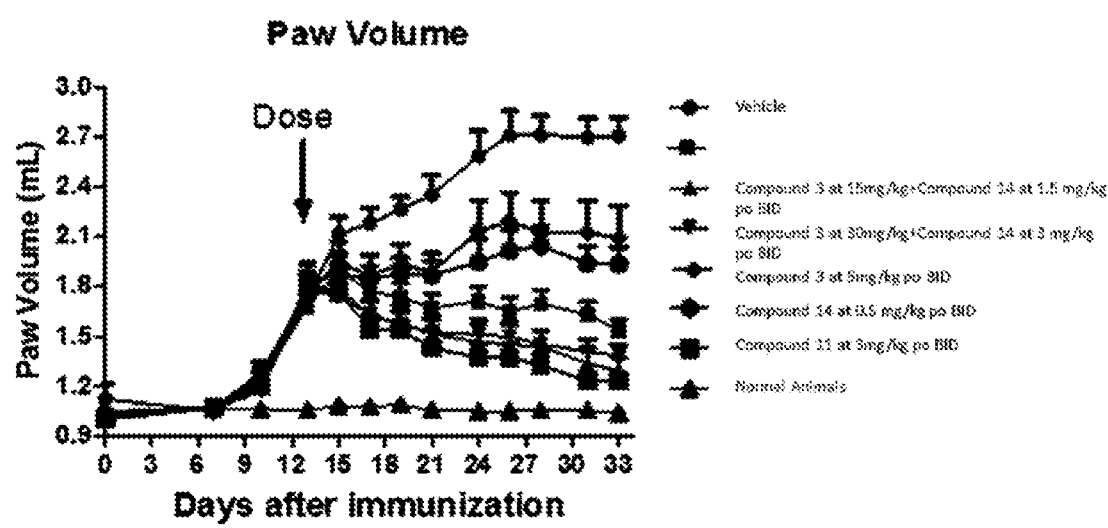
FIG. 13 is a graph showing the paw volume of the test animals in the Adjuvant-Induced Arthritis (AIA) study. Data are shown as mean±SEM.
Figure 14:
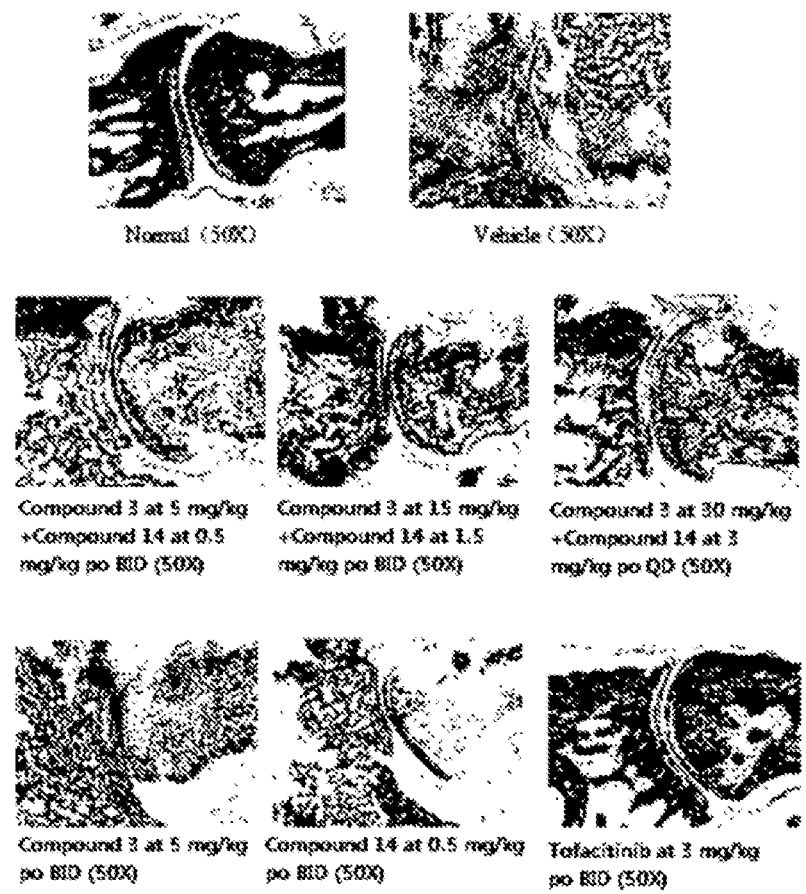
FIG. 14 is a panel of representative photographic images of H&E staining from each group of the AIA Study.

As shown in FIG. 13, the combination of a BTK inhibitor (e.g., Compound 3) and an mTOR kinase inhibitor (e.g., Compound 14) at various doses synergistically reduced the paw volume of AA rats model, exhibiting efficacies similar to the positive control (Tofactinib). Such treatment effects are absent from rats treated with Compound 3 alone or Compound 14 alone.

Figure 15:
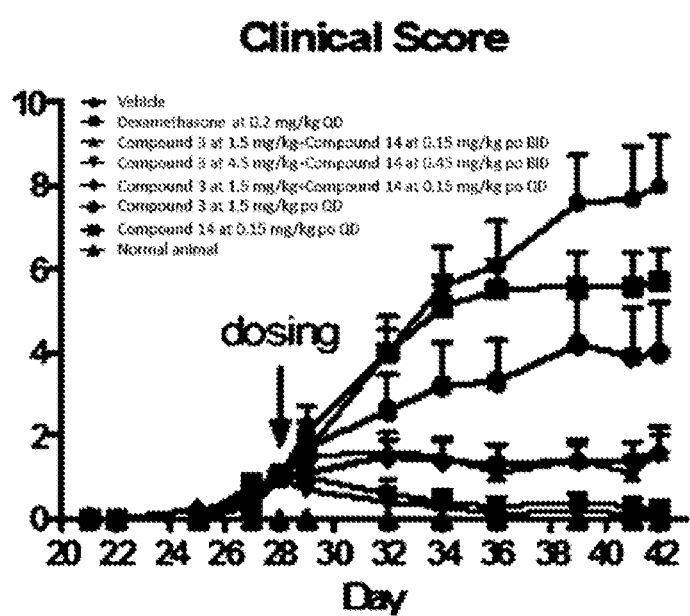
FIG. 15 is a graph showing the Clinical Score of the Collagen-Induced Arthritis (CIA) Study. Data are shown as mean±SEM.
Figure 16:
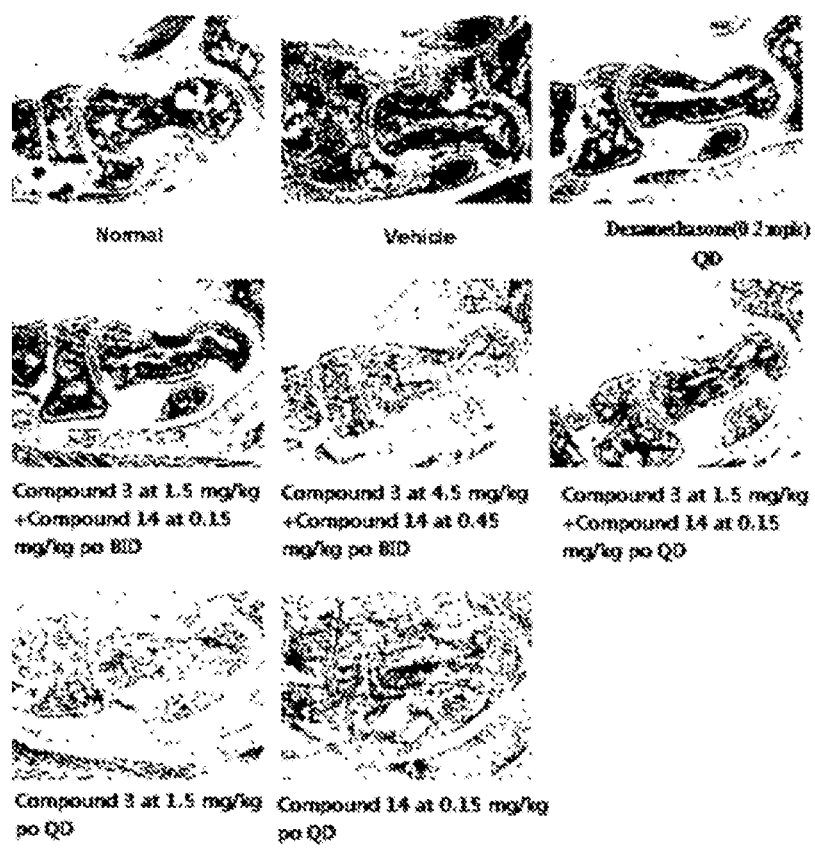
FIG. 16 is a panel of representative photographic images of H&E staining from each group (40×) of the CIA Study.

As shown in FIG. 15, the combination of a BTK inhibitor (e.g., Compound 3) and an mTOR kinase inhibitor (e.g., Compound 14) at various doses synergistically reduced the clinical score of CIA mice model, exhibiting efficacies similar to the positive control (Dexamethasone). Such treatment effects are absent from mice treated with Compound 3 alone or Compound 14 alone.

Additional data of the BTK Compounds are shown in the tables below. Table 13 below demonstrates that low dose combination is synergistic against tumor cells and has shown synthetic lethality. At much lower dose than each single agent, the triple combination of Compounds 3, 14, and 15 resulted in completed tumor regression in 9 days while the double combination of Compounds 3 and 14 required 15 days. Single agent was much less effective or causing tumor to rebound when the administration of such agent is stopped. No tumor rebound was seen with the triple combination after tumor regression even when the administration of the triple combination is switched to the vehicle.

TABLE 13

Antitumor effect of Single-drug and combination therapy

Figure 1B:
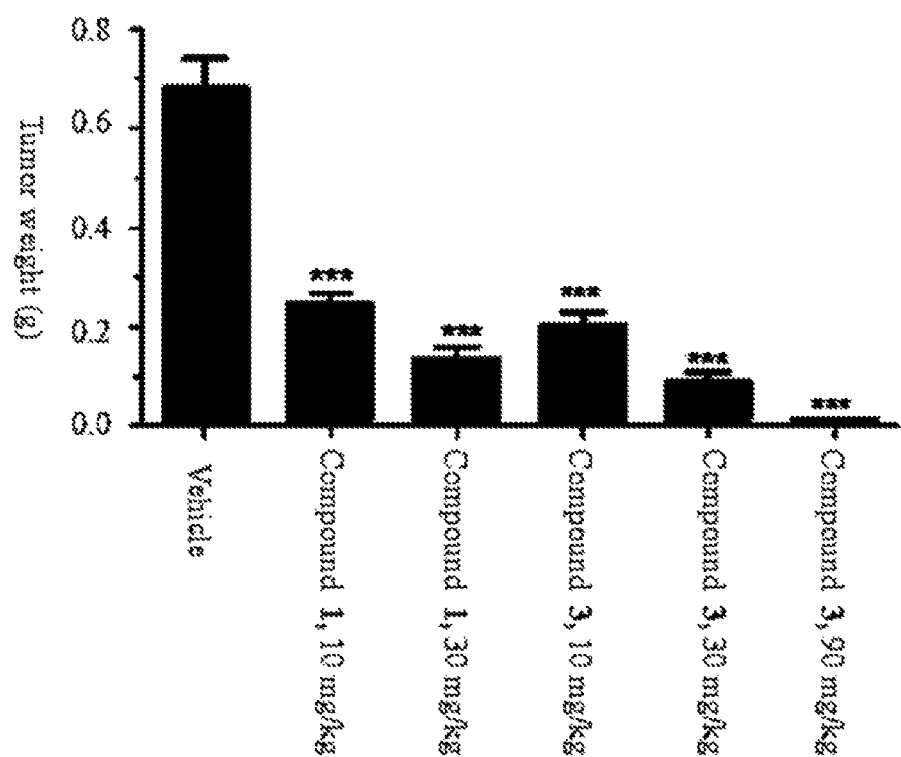
FIG. 1B is a graph showing the antitumor effect of Compounds 1 and 3 on tumor weight in the TMD-8 lymphoma xenograft SCID mouse model.

| Corresponding FIG. | Dose | Compound (mg/kg) | Antitumor effect (%) |
|---|---|---|---|
| FIG.-1 | Oral, BID, 14 days | Vehicle control | — |
| | | 1 (10 mg/kg) | 56 |
| | | 1 (30 mg/kg) | 77 |
| | | 3 (10 mg/kg) | 64 |
| | | 3 (30 mg/kg) | 82 |
| | | 3 (90 mg/kg) | 93 |
| FIG.-2 | Oral, BID, 14 days | Vehicle control | — |
| | | 3 (10 mg/kg) | 63 |
| | | 3 (30 mg/kg) | 89 |
| | | 15 (30 mg/kg) | 24 |
| | | 3 (10 mg/kg) 15 (30 mg/kg) | 95 |
| FIG.-3 | Oral, BID, 21 days | Vehicle control | — |
| | | 3 (5 mg/kg) | 90 |
| | | 3 (10 mg/kg) | 96 |
| | | 15 (10 mg/kg) | −8 |
| | | 8 (10 mg/kg) | 26 |
| | | 3 (5 mg/kg) 15 (10 mg/kg) | 82 |
| | | 3 (10 mg/kg) 15 (10 mg/kg) | 89 |
| | | 3 (5 mg/kg) 8 (10 mg/kg) | 95 |
| | | 3 (10 mg/kg) 8 (10 mg/kg) | 98 |
| | | 3 (5 mg/kg) 15 (10 mg/kg) 8 (10 mg/kg) | 94 |
| | | 3 (10 mg/kg) 15 (10 mg/kg) 8 (10 mg/kg) | 94 |
| | | 15 (10 mg/kg) 8 (10 mg/kg) | 86 |
| FIG.-4 | Oral, BID, 21 days | Vehicle control | — |
| | | 3 (10 mg/kg) | 77 |
| | | 16 (10 mg/kg) | 16 |
| | | 16 (30 mg/kg) | 42 |
| | | 14 (1 mg/kg) | 97 (Tumor rebounded at day 17.) |
| | | 14 (3 mg/kg) | 99 (Tumor rebounded at day 19.) |
| | | 3 (10 mg/kg) 14 (1 mg/kg) | 100 (Tumor didn't rebound from day 15.) |
| | | 3 (10 mg/kg) 14 (3 mg/kg) | 100 (Tumor didn't rebound from day 15.) |
| | | 3 (10 mg/kg) 16 (10 mg/kg) | 72 |
| | | 3 (10 mg/kg) 16 (30 mg/kg) | 80 |

TABLE 13-continued

Antitumor effect of Single-drug and combination therapy

Figure 11:
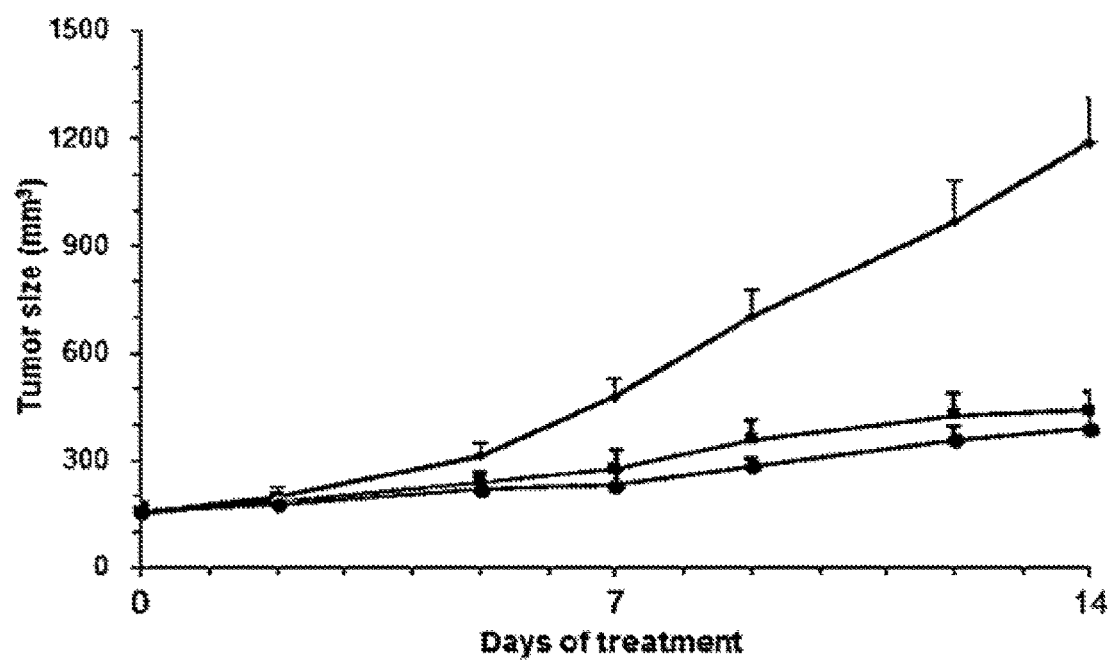
FIG. 11 is a graph showing the antitumor effect of triple combinations of Compound 3 or 9 with Compounds 14 and 15 in the DoHH2 mouse model.

| Corresponding FIG. | Dose | Compound (mg/kg) | Antitumor effect (%) |
|---|---|---|---|
| FIG.-5 | Oral, BID, 21 days | Vehicle control | — |
| | | 3 (5 mg/kg) | 33 |
| | | 3 (5 mg/kg)<br>15 (5 mg/kg)<br>14 (0.5 mg/kg) | 100 (Tumor disappeared completely at day 9 and didn't rebound.) |
| FIG.-10 | Oral, BID, 14 days | Vehicle control | — |
| | | 3 (5 mg/kg)<br>15 (5 mg/kg)<br>14 (0.5 mg/kg) | 100 (Tumor disappeared completely at day 10 and didn't rebound.) |
| | | 3 (10 mg/kg)<br>15 (1 mg/kg)<br>14 (0.5 mg/kg) | 100 (Tumor disappeared completely at day 10 and didn't rebound.) |
| | | 3 (20 mg/kg)<br>15 (1 mg/kg)<br>14 (0.5 mg/kg) | 100 (Tumor disappeared completely at day 10 and didn't rebound.) |
| FIG.-7 | Oral, BID, 21 days | Vehicle control | — |
| | | 3 (5 mg/kg) | 15.9 |
| | | 3 (5 mg/kg)<br>15 (5 mg/kg)<br>14 (0.5 mg/kg) | 80.3 |
| FIG.-6 | Oral, BID, 21 days | Vehicle control | — |
| | | 3 (5 mg/kg) | 28.8 |
| | | 3 (10 mg/kg) | 20.1 |
| | | 3 (30 mg/kg) | 35.6 |
| | | 3 (5 mg/kg)<br>14 (0.5 mg/kg) | 58.3 |
| | | 3 (5 mg/kg)<br>15 (5 mg/kg)<br>14 (0.5 mg/kg) | 79.4 |
| FIG.-8 | Oral, BID, 28 days | Vehicle control | — |
| | | 9 (30 mg/kg) | 24 |
| | | 3 (10 mg/kg) | 22 |
| | | 3 (30 mg/kg) | 30 |
| | | 3 (45 mg/kg) | 32 |
| FIG.-9 | Oral, BID, 18 days | Vehicle control | — |
| | | 3 (5 mg/kg) | 4 |
| | | 3 (10 mg/kg) | 7 |
| | | 3 (30 mg/kg) | 23 |
| | | 3 (5 mg/kg)<br>14 (0.5 mg/kg) | 44 |
| | | 3 (5 mg/kg)<br>15 (5 mg/kg)<br>14 (0.5 mg/kg) | 50 |
| FIG.-11 | Oral, BID, 14 days | Vehicle control | — |
| | | 3 (5 mg/kg)<br>15 (5 mg/kg)<br>14 (0.5 mg/kg) | 63 |
| | | 9 (4.3 mg/kg)<br>15 (5 mg/kg)<br>14 (0.5 mg/kg) | 67 |
| FIG.-12 | Oral, BID, 14 days | Vehicle control | — |
| | | 3 (5 mg/kg) | 75 |
| | | 12 (5 mg/kg) | 12 |
| | | 8 (10 mg/kg) | 48 |
| | | 3 (5 mg/kg)<br>12 (5 mg/kg) | 86 |
| | | 8 (10 mg/kg)<br>12 (5 mg/kg) | 37 |
| | | 12 (5 mg/kg)<br>14 (0.5 mg/kg) | 77 |
| | | 3 (5 mg/kg)<br>12 (5 mg/kg)<br>14 (0.5 mg/kg) | 100 |
| | | 3 (5 mg/kg)<br>12 (5 mg/kg)<br>8 (10 mg/kg) | 89 |

Table 14 demonstrates that the lose dose combination is safe without any significant body weight changes between all treated and control groups.

TABLE 14

Animal weight for Mar. 14, 2015 and Sep. 14, 2015 combination therapy

| Weight (g) | Day | 0 | 2 | 5 | 7 | 9 | 12 | 14 |
|---|---|---|---|---|---|---|---|---|
| Vehicle control | Mean | 22.9 | 22.4 | 22.8 | 23.0 | 23.7 | 23.5 | 23.6 |
| | SEM | 0.5 | 0.5 | 0.6 | 0.5 | 0.6 | 0.5 | 0.6 |
| 3 (5 mg/kg)<br>15 (5 mg/kg)<br>14 (0.5 mg/kg) | Mean | 21.9 | 21.6 | 22.8 | 22.5 | 22.6 | 22.5 | 22.3 |
| | SEM | 0.4 | 0.4 | 0.3 | 0.4 | 0.5 | 0.5 | 0.6 |
| 9 (4.3 mg/kg)<br>15 (5 mg/kg)<br>14 (0.5 mg/kg) | Mean | 22.2 | 21.7 | 22.7 | 22.9 | 23.1 | 22.7 | 22.6 |
| | SEM | 0.5 | 0.5 | 0.6 | 0.5 | 0.4 | 0.4 | 0.6 |

Table 14 demonstrates that the lose dose combination at various doses of each agent is safe without any significant body weight changes between all treated and control groups.

TABLE 15

Animal weight for Mar. 14, 2015 combination therapy

| Weight (g) | Day | 0 | 2 | 5 | 7 | 9 | 12 | 14 |
|---|---|---|---|---|---|---|---|---|
| Vehicle control | Mean | 21.2 | 21.1 | 21.1 | 21.4 | 21.5 | 21.8 | 21.9 |
| | SEM | 0.5 | 0.4 | 0.4 | 0.5 | 0.4 | 0.5 | 0.5 |
| 3 (5 mg/kg)<br>15 (5 mg/kg)<br>14 (0.5 mg/kg) | Mean | 22.1 | 21.8 | 21.8 | 21.8 | 21.7 | 22.3 | 21.7 |
| | SEM | 0.8 | 0.7 | 0.8 | 0.7 | 0.8 | 0.8 | 0.7 |
| 3 (10 mg/kg)<br>15 (1 mg/kg)<br>14 (0.5 mg/kg) | Mean | 21.6 | 21.5 | 21.8 | 22.2 | 22.4 | 22.4 | 22.1 |
| | SEM | 0.5 | 0.6 | 0.6 | 0.7 | 0.7 | 0.6 | 0.7 |
| 3 (20 mg/kg)<br>15 (1 mg/kg)<br>14 (0.5 mg/kg) | Mean | 21.4 | 21.0 | 21.1 | 21.3 | 21.4 | 21.3 | 21.4 |
| | SEM | 0.6 | 0.5 | 0.5 | 0.6 | 0.6 | 0.5 | 0.6 |

Table 16 below shows that not all triple combinations have superior synergistic effects, further evidencing that the synergistic effects with the triple combinations of BTK/mTOR/IMiD and BTK/mTOR/Bcl-2 are unexpected. Both in vitro and in vivo synergistic effects suppressing cancer cells have been achieved with these two triple combinations.

TABLE 16

Lack of inhibition on tumor cell viability for triple combination of JAK1 inhibition with BTK/IMid, IMiD/PI3K and IMid/mTOR

| Comp.@Conc. | Inh % | 10 @1 uM | 10 @0.01 uM | 10 @0.01 uM |
|---|---|---|---|---|
| 15 @0.1 uM +<br>3 @0.1 uM | AVG<br>SD | 24.40<br>5.84 | −6.35<br>5.66 | −0.77<br>18.61 |
| 15 @0.1 uM +<br>8 @0.1 uM | AVG<br>SD | 16.26<br>2.14 | 2.31<br>1.28 | −6.21<br>4.86 |
| 15 @0.1 uM +<br>14 @0.1 uM | AVG<br>SD | −0.86<br>6.5 | 0.98<br>5.87 | −2.4<br>1.06 |

Tables 17-20 below show that double combination is more effective than single agent alone in autoimmune animal models.

TABLE 17

Paw volume of the animals during the AA study

| Paw volume (mL) | Day | 0 | 17 | 26 | 28 | 31 | 33 |
|---|---|---|---|---|---|---|---|
| Normal | Mean | 1.00 | 1.08 | 1.05 | 1.05 | 1.05 | 1.04 |
| | SEM | 0.03 | 0.02 | 0.01 | 0.02 | 0.02 | 0.02 |
| Vehicle control | Mean | 1.12 | 2.18 | 2.71 | 2.71 | 2.69 | 2.70 |
| | SEM | 0.09 | 0.09 | 0.15 | 0.11 | 0.11 | 0.11 |

TABLE 17-continued

Paw volume of the animals during the AA study

| Paw volume (mL) | Day | 0 | 17 | 26 | 28 | 31 | 33 |
|---|---|---|---|---|---|---|---|
| 3 (5 mg/kg) 14 (0.5 mg/kg) | Mean | 1.03 | 1.77* | 1.65*** | 1.69*** | 1.63*** | 1.53*** |
|  | SEM | 0.02 | 0.07 | 0.08 | 0.08 | 0.08 | 0.07 |
| 3 (15 mg/kg) 14 (1.5 mg/kg) | Mean | 1.01 | 1.62*** | 1.45*** | 1.44*** | 1.34*** | 1.29*** |
|  | SEM | 0.02 | 0.10 | 0.11 | 0.10 | 0.09 | 0.08 |
| 3 (30 mg/kg) 14 (3 mg/kg) | Mean | 1.01 | 1.63*** | 1.50*** | 1.45*** | 1.41*** | 1.38*** |
|  | SEM | 0.01 | 0.08 | 0.09 | 0.08 | 0.08 | 0.07 |
| 3 (5 mg/kg) | Mean | 1.04 | 1.87 ns | 2.29** | 2.12*** | 2.12*** | 2.09*** |
|  | SEM | 0.01 | 0.12 | 0.14 | 0.19 | 0.19 | 0.20 |
| 14 (0.5 mg/kg) | Mean | 1.02 | 1.84 ns | 2.01*** | 2.04*** | 1.94*** | 1.93*** |
|  | SEM | 0.01 | 0.08 | 0.13 | 0.12 | 0.11 | 0.10 |
| 11 (3 mg/kg) | Mean | 1.00 | 1.54*** | 1.37*** | 1.33*** | 1.23*** | 1.23*** |
|  | SEM | 0.02 | 0.08 | 0.08 | 0.07 | 0.05 | 0.05 |

*p < 0.05,
**p < 0.01,
***p < 0.001

TABLE 18

Pathological score of the animals during the AA study

| Group | Pathological score (Mean ± SEM) | | | | |
|---|---|---|---|---|---|
|  | Inflammatory cell infiltration | Pannus growth | Cartilage injury | Bone resorption | Total |
| Normal | 0.0 ± 0.00 | 0.0 ± 0.00 | 0.0 ± 0.00 | 0.0 ± 0.00 | 0.0 ± 0.00 |
| Vehicle control | 4 ± 0.00 | 4 ± 0.00 | 3.8 ± 0.13 | 3.7 ± 0.15 | 15.5 ± 0.27 |
| 3 (5 mg/kg) 14 (0.5 mg/kg) | 3.5 ± 0.22 | 2.8 ± 0.25 | 2.6 ± 0.27 | 2.8 ± 0.29 | 11.7 ± 0.96 |
| 3 (15 mg/kg) 14 (1.5 mg/kg) | 2.9 ± 0.31 | 1.6 ± 0.22 | 1.1 ± 0.28 | 2.2 ± 0.49 | 7.8 ± 1.21*** |
| 3 (30 mg/kg) 14 (3 mg/kg) | 2.6 ± 0.37 | 2.2 ± 0.44 | 1.7 ± 0.40 | 2.4 ± 0.40 | 8.9 ± 1.55*** |
| 3 (5 mg/kg) 14 (0.5 mg/kg) | 3.5 ± 0.34 | 3.2 ± 0.53 | 2.8 ± 0.51 | 3.0 ± 0.45 | 12.5 ± 1.78 |
|  | 3.9 ± 0.10 | 3.7 ± 0.21 | 3.5 ± 0.27 | 3.5 ± 0.17 | 14.6 ± 0.54 |
| 11 (3 mg/kg) | 1.9 ± 0.18 | 0.4 ± 0.22 | 0.2 ± 0.20 | 0.5 ± 0.22 | 3.0 ± 0.73*** |

***p < 0.001, v.s. Vehicle, Kruskal-Wallis test, Dunn's post-hoc test

TABLE 19

Clinical Score after twenty-first days after the first immunization during the CIA Study

| Clinical Score | day | 21 | 32 | 39 | 42 |
|---|---|---|---|---|---|
| Normal | Mean | 0.00 | 0.00 | 0.00 | 0.00 |
|  | SEM | 0.00 | 0.00 | 0.00 | 0.00 |
| Vehicle control | Mean | 0.00 | 4.00 | 7.6 | 8.00 |
|  | SEM | 0.00 | 0.86 | 1.14 | 1.20 |
| Dexamethasone (0.2 mg/kg) | Mean | 0.00 | 0.60*** | 0.40*** | 0.20*** |
|  | SEM | 0.00 | 0.34 | 0.22 | 0.20 |
| 3 (1.5 mg/kg) 14 (0.15 mg/kg) BID | Mean | 0.00 | 1.60* | 1.40*** | 1.60*** |
|  | SEM | 0.00 | 0.45 | 0.37 | 0.40 |
| 3 (4.5 mg/kg) 14 (0.45 mg/kg) BID | Mean | 0.00 | 0.40*** | 0.2*** | 0.10*** |
|  | SEM | 0.00 | 0.16 | 0.13 | 0.10 |
| 3 (1.5 mg/kg) 14 (0.15 mg/kg) QD | Mean | 0.00 | 1.50** | 1.40*** | 1.60*** |
|  | SEM | 0.00 | 0.40 | 0.50 | 0.58 |
| 3 (1.5 mg/kg) QD | Mean | 0.00 | 2.60 | 4.20*** | 4.00*** |
|  | SEM | 0.00 | 0.86 | 1.14 | 1.22 |
| 14 (0.15 mg/kg) QD | Mean | 0.00 | 4.00 | 5.60 | 5.70* |
|  | SEM | 0.00 | 0.54 | 0.82 | 0.80 |

*p < 0.05,
**p < 0.01,
***p < 0.001, v.s. Vehicle, Two-way ANOVA, Bonferrni's post-hoc test

TABLE 20

Pathological score of the animals during the CIA study

| Group | | Inflammatory cell infiltration | Pannus growth | Cartilage injury | Bone resorption | Total |
|---|---|---|---|---|---|---|
| Vehicle control | Left hind paw | 1.60 ± 0.65 | 1.30 ± 0.56 | 1.40 ± 0.58 | 1.00 ± 0.42 | 15.50 ± 2.30 |
| | Right hind paw | 2.80 ± 0.61 | 2.40 ± 0.54 | 2.50 ± 0.56 | 2.50 ± 0.56 | |
| Dexamethasone (0.2 mg/kg) QD | Left hind paw | 0.00 ± 0.00 | 0.00 ± 0.00 | 0.00 ± 0.00 | 0.00 ± 0.00 | 0.00 ± 0.00 *** |
| | Right hind paw | 0.00 ± 0.00 | 0.00 ± 0.00 | 0.00 ± 0.00 | 0.00 ± 0.00 | |
| 3 (1.5 mg/kg) 14 (0.15 mg/kg) BID | Left hind paw | 0.50 ± 0.22 | 0.20 ± 0.20 | 0.20 ± 0.20 | 0.10 ± 0.10 | 1.50 ± 0.78 *** |
| | Right hind paw | 0.20 ± 0.20 | 0.10 ± 0.10 | 0.10 ± 0.10 | 0.10 ± 0.10 | |
| 3 (4.5 mg/kg) 14 (0.45 mg/kg) BID | Left hind paw | 0.00 ± 0.00 | 0.00 ± 0.00 | 0.00 ± 0.00 | 0.00 ± 0.00 | 0.00 ± 0.00 *** |
| | Right hind paw | 0.00 ± 0.00 | 0.00 ± 0.00 | 0.00 ± 0.00 | 0.00 ± 0.00 | |
| 3 (1.5 mg/kg) 14 (0.15 mg/kg) QD | Left hind paw | 0.20 ± 0.20 | 0.20 ± 0.20 | 0.20 ± 0.20 | 0.20 ± 0.20 | 0.80 ± 0.80 *** |
| | Right hind paw | 0.00 ± 0.00 | 0.00 ± 0.00 | 0.00 ± 0.00 | 0.00 ± 0.00 | |
| 3 (1.5 mg/kg) QD | Left hind paw | 1.00 ± 0.47 | 0.80 ± 0.47 | 0.80 ± 0.47 | 0.60 ± 0.13 | 3.90 ± 1.80 *** |
| | Right hind paw | 0.20 ± 0.20 | 0.20 ± 0.20 | 0.20 ± 0.20 | 0.10 ± 0.10 | |
| 14 (0.15 mg/kg) QD | Left hind paw | 2.10 ± 0.64 | 2.00 ± 0.67 | 2.00 ± 0.67 | 1.80 ± 0.61 | 15.90 ± 4.50 |
| | Right hind paw | 2.00 ± 0.67 | 2.00 ± 0.67 | 2.00 ± 0.67 | 2.00 ± 0.67 | |
| Normal | Left hind paw | 0.00 ± 0.00 | 0.00 ± 0.00 | 0.00 ± 0.00 | 0.00 ± 0.00 | 0.00 ± 0.00 |
| | Right hind paw | 0.00 ± 0.00 | 0.00 ± 0.00 | 0.00 ± 0.00 | 0.00 ± 0.00 | |

*** $p < 0.001$, v.s. Vehicle, Kruskal-Wallis test, Dunn's post-hoc test

Table 21 below shows the structures of some of the compounds useful in the present invention.

TABLE 21

| Entry | Compound Code | Name | Structure |
|---|---|---|---|
| 1 | ACP-196 | Acalabrutinib | 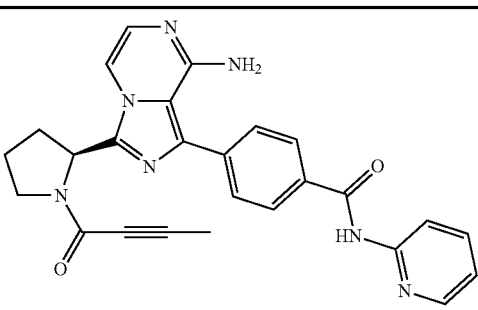 |
| 2 | AVL-292 (CC-292) | | 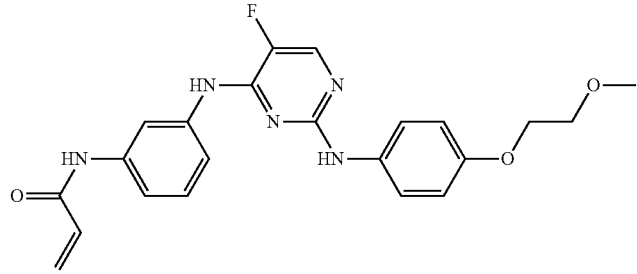 [SMILES: C=CC(=O)Nc1cccc(Nc2nc(Nc3ccc(OCCOC)cc3)ncc2F)c1] |

TABLE 21-continued
| Entry | Compound Code | Name | Structure |
|---|---|---|---|
| 3 | ONO-4059 | | 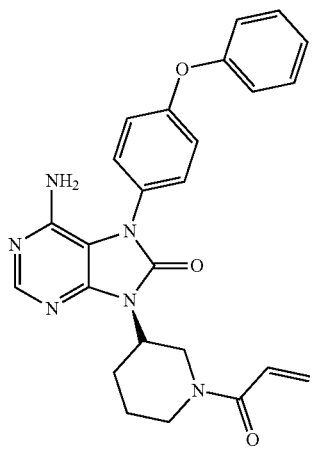 |
| 4 | HM71224 | Olmutinib | 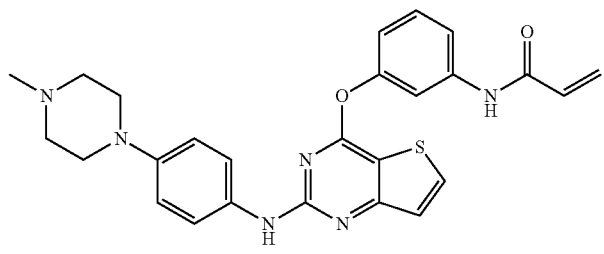 [SMILES: C=CC(=O)Nc1cccc(Oc2nc(Nc3ccc(N4CCN(C)CC4)cc3)nc3ccsc23)c1] |
| 5 | RN486 | | 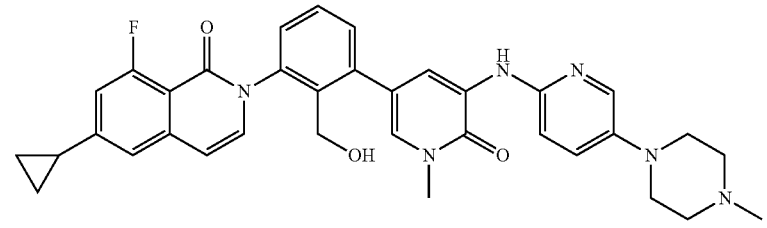 [SMILES: CN1CCN(c2ccc(Nc3cc(-c4cccc(-n5ccc6cc(C7CC7)cc(F)c6c5=O)c4CO)cn(C)c3=O)nc2)CC1] |
| 6 | CNX-774 | | 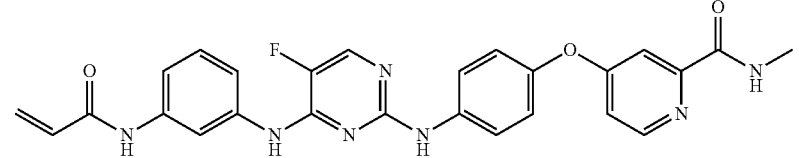 [SMILES: C=CC(=O)Nc1cccc(Nc2nc(Nc3ccc(Oc4ccnc(C(=O)NC)c4)cc3)ncc2F)c1] |
| 7 | XL388 | | 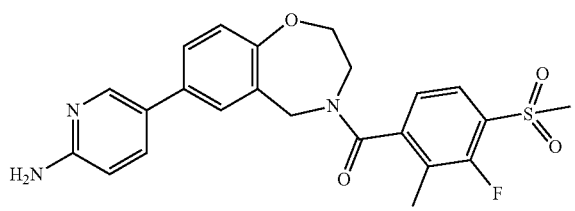 [SMILES: Cc1c(C(=O)N2CCOc3ccc(-c4ccc(N)nc4)cc3C2)ccc(S(C)(=O)=O)c1F] |

TABLE 21-continued
| Entry | Compound Code | Name | Structure |
|---|---|---|---|
| 8 | GDC-0349 | | 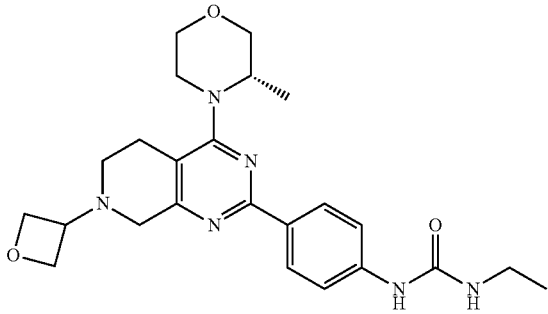 [SMILES: CCNC(=O)Nc1ccc(-c2nc3c(c(N4CCOC[C@@H]4C)n2)CCN(C2COC2)C3)cc1] |
| 9 | AZD2014 | Vistusertib | 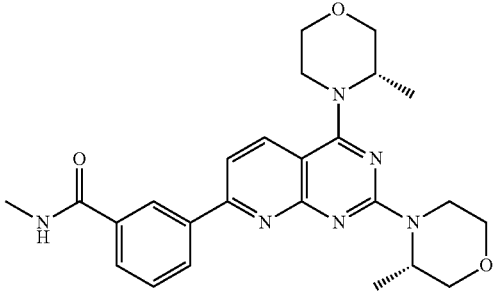 [SMILES: CNC(=O)c1cccc(-c2ccc3c(N4CCOC[C@@H]4C)nc(N4CCOC[C@@H]4C)nc3n2)c1] |
| 10 | AZD8055 | | 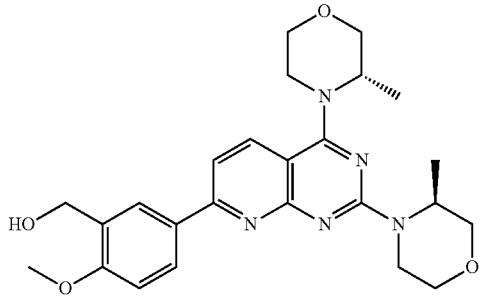 [SMILES: COc1ccc(-c2ccc3c(N4CCOC[C@@H]4C)nc(N4CCOC[C@@H]4C)nc3n2)cc1CO] |
| 11 | MLN0128 | Sapanisertib | 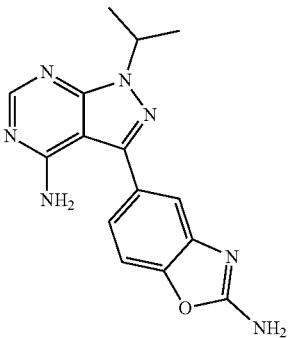 [SMILES: CC(C)n1nc(-c2ccc3oc(N)nc3c2)c2c(N)ncnc21] |
| 12 | CC-122 | | 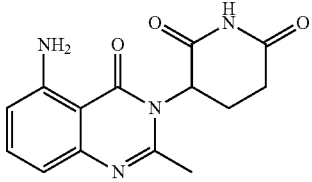 [SMILES: Cc1nc2cccc(N)c2c(=O)n1C1CCC(=O)NC1=O] |

TABLE 21-continued
| Entry | Compound Code | Name | Structure |
|---|---|---|---|
| 13 | CC-220 | | 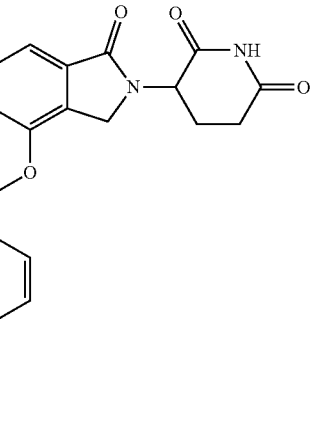 |
| 14 | PF-05212384 | Gedatolisib | 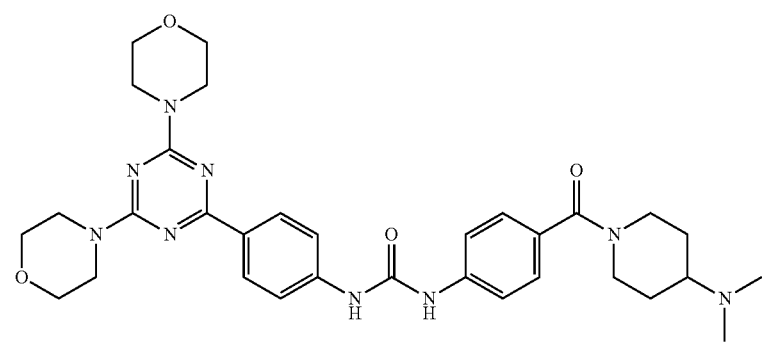 [SMILES: CN(C)C1CCN(C(=O)c2ccc(NC(=O)Nc3ccc(-c4nc(N5CCOCC5)nc(N5CCOCC5)n4)cc3)cc2)CC1] |
| 15 | GDC-0980 | Apitolisib | 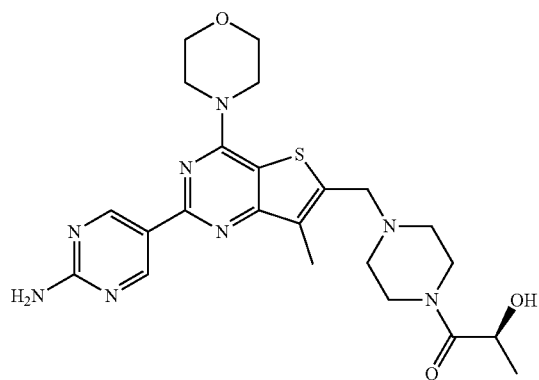 [SMILES: Cc1c(CN2CCN(C(=O)[C@H](C)O)CC2)sc2c(N3CCOCC3)nc(-c3cnc(N)nc3)nc12] |
| 16 | GSK2126458 | | 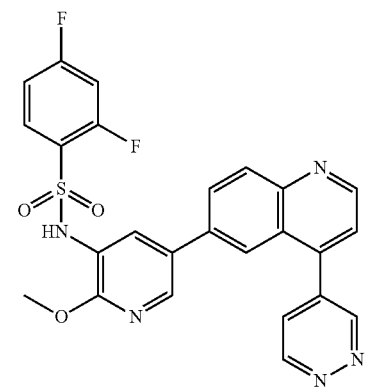 [SMILES: COc1ncc(-c2ccc3nccc(-c4ccnnc4)c3c2)cc1NS(=O)(=O)c1ccc(F)cc1F] |

TABLE 21-continued
| Entry | Compound Code | Name | Structure |
|---|---|---|---|
| 17 | BEZ235 | | 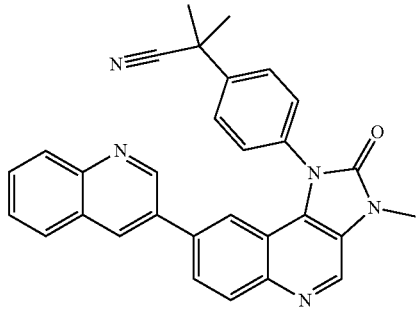 [SMILES: Cn1c(=O)n(-c2ccc(C(C)(C)C#N)cc2)c2c3cc(-c4cnc5ccccc5c4)ccc3ncc21] |
| 18 | IPI-145 | Duvelisib | 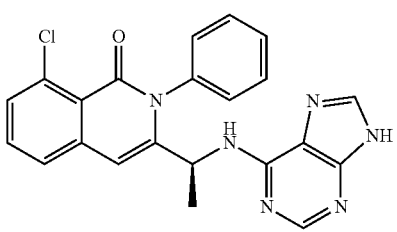 [SMILES: C[C@H](Nc1ncnc2[nH]cnc12)c1cc2cccc(Cl)c2c(=O)n1-c1ccccc1] |
| 19 | CAL-101 | Idelalisib | 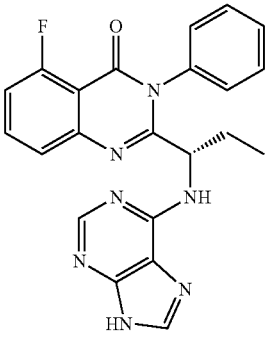 [SMILES: CC[C@H](Nc1ncnc2[nH]cnc12)c1nc2cccc(F)c2c(=O)n1-c1ccccc1] |
| 20 | ABT-199 | Venetoclax | 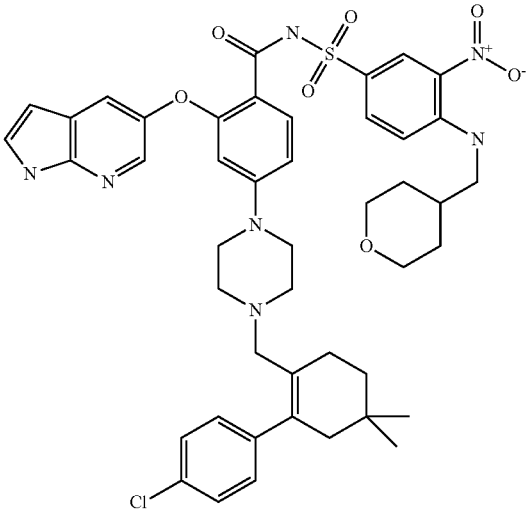 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] |

TABLE 21-continued

| Entry | Compound Code | Name | Structure |
|---|---|---|---|
| 21 | BI-97C1 | sabutoclax | 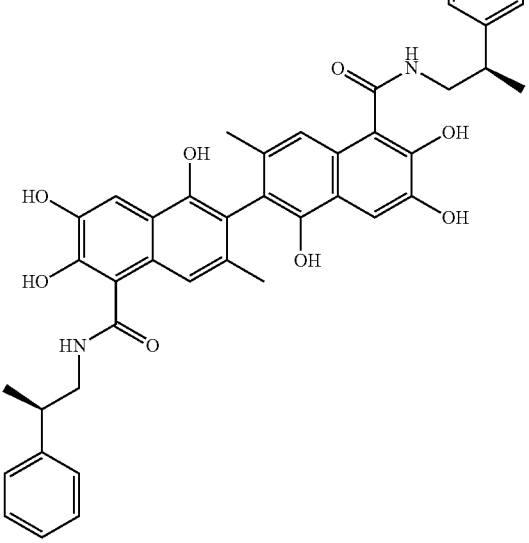 |
| 22 | OTS964 | | 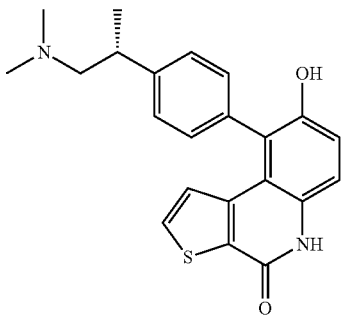 [SMILES: C[C@@H](CN(C)C)c1ccc(-c2c(O)ccc3[nH]c(=O)c4sccc4c23)cc1] |
| 23 | CH5424802 | Alectinib | 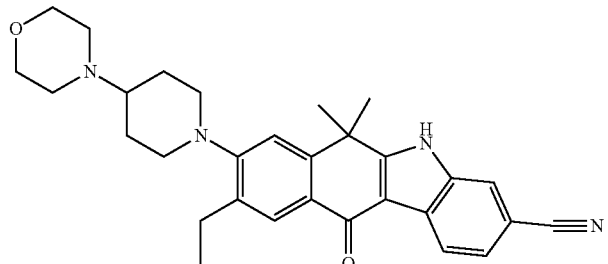 |

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art.

Throughout this specification and embodiments, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

What is claimed is:

1. A pharmaceutical composition comprising
   a Bruton tyrosine kinase (BTK) inhibitor, wherein the BTK inhibitor is Compound 3 as shown in Table 1, or an enantiomer, a diastereomer, a pharmaceutically acceptable salt, or a prodrug thereof,
   a mammalian target of rapamycin (mTOR) kinase inhibitor, wherein the mTOR kinase inhibitor is everolimus or rapamycin, or a pharmaceutically acceptable salt thereof, and
   a pharmaceutically acceptable carrier.

2. The pharmaceutical composition of claim 1, further comprising an immunomodulatory drug (IMiD), wherein the IMiD is pomalidomide or a pharmaceutically acceptable salt thereof.

3. The pharmaceutical composition of claim 1, further comprising a Bcl-2 inhibitor, wherein the Bcl-2 inhibitor is venetoclax or a pharmaceutically acceptable salt thereof.

* * * * *